United States Patent
Abe et al.

(10) Patent No.: US 10,463,647 B2
(45) Date of Patent: Nov. 5, 2019

(54) ERYTHROPOIETIN EXPRESSION PROMOTER

(71) Applicant: TOHOKU UNIVERSITY, Miyagi (JP)

(72) Inventors: Takaaki Abe, Miyagi (JP); Teiji Tominaga, Miyagi (JP); Kenichiro Hayashi, Okayama (JP); Hitoshi Osaka, Tochigi (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 16/017,520

(22) Filed: Jun. 25, 2018

(65) Prior Publication Data

US 2018/0353475 A1 Dec. 13, 2018

Related U.S. Application Data

(62) Division of application No. 14/646,640, filed as application No. PCT/JP2013/006916 on Nov. 25, 2013, now Pat. No. 10,004,718.

(30) Foreign Application Priority Data

Nov. 26, 2012 (JP) .................................. 2012-258027

(51) Int. Cl.
| | |
|---|---|
| *C07D 401/06* | (2006.01) |
| *A61K 31/405* | (2006.01) |
| *C07D 209/20* | (2006.01) |
| *C07D 209/18* | (2006.01) |
| *A61K 31/192* | (2006.01) |
| *A61K 31/454* | (2006.01) |

(52) U.S. Cl.
CPC .......... *A61K 31/405* (2013.01); *A61K 31/192* (2013.01); *A61K 31/454* (2013.01); *C07D 209/18* (2013.01); *C07D 209/20* (2013.01); *C07D 401/06* (2013.01)

(58) Field of Classification Search
CPC .................................................. C07D 401/06
See application file for complete search history.

(56) References Cited

U.S. PATENT DOCUMENTS

| | | | |
|---|---|---|---|
| 2003/0195212 | A1 | 10/2003 | Lundstedt et al. |
| 2004/0259875 | A1 | 12/2004 | Yura et al. |
| 2007/0184091 | A1 | 8/2007 | Gillessen et al. |
| 2008/0194553 | A1 | 8/2008 | Gillessen et al. |
| 2011/0077267 | A1 | 3/2011 | Mitani et al. |
| 2011/0230524 | A1 | 9/2011 | Ivashchenko et al. |

FOREIGN PATENT DOCUMENTS

| | | |
|---|---|---|
| CN | 1938018 A | 3/2007 |
| JP | 2003/520850 A | 7/2003 |
| JP | 2005/501873 A | 1/2005 |
| JP | 2007/507213 A | 3/2007 |
| JP | 2011/190206 A | 9/2011 |
| JP | 2012/082181 A | 4/2012 |
| JP | 2012/144571 A | 8/2012 |
| WO | WO 2010/075263 | 7/2010 |

OTHER PUBLICATIONS

Taborsky, et al. Document No. 61:51251, retrieved from STN, entered in STN on Apr. 22, 2001.*
Schwyzer, et al. Document No. 53:121556, retrieved from STN, entered in STN on Apr. 22, 2001.*
Koo, et al. Document No. 53:94743, retrieved from STN, entered in STN on Apr. 22, 2001.*
Upjohn Co. Document No. 50, 89506, retrieved from STN, entered in STN on Apr. 22, 2001.*
Stoll, et al. Document No. 50:27880, retrieved from STN; entered in STN on Apr. 22, 2001.*
Speeter, et al. Document No. 49:78071, retrieved from STN; entered in STN on Apr. 22, 2001.*
Rydon, et al. Document No. 4648578, retrieved from STN; entered in STN on Apr. 22, 2001.*

(Continued)

*Primary Examiner* — Shawquia Jackson
(74) *Attorney, Agent, or Firm* — Margaret B Brivanlou; Kristine Waddell; King & Spalding LLP

(57) ABSTRACT

The present invention provides an erythropoietin expression-enhancing agent that can cancel the suppression of erythropoietin production or promote erythropoietin production, and a therapeutic or preventive drug for anemia, a liver function-improving agent, an ischemic injury-improving agent, a renal protective agent, and an insulin secretagogue comprising the erythropoietin expression-enhancing agent. The erythropoietin expression-enhancing agent of the present invention comprises one or more compounds selected from the group consisting of compounds represented by the following general formulas (I), (II), and (III) and pharmaceutically acceptable salts thereof when $R^3$ is OH.

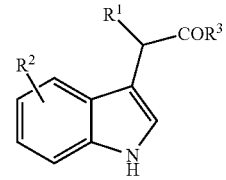

(I)

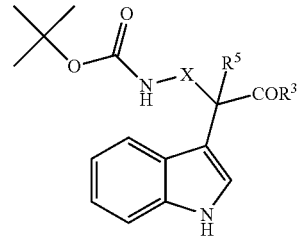

(II)

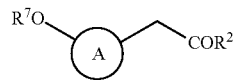

(III)

2 Claims, 11 Drawing Sheets

(56) References Cited

OTHER PUBLICATIONS

Hayashi, et al. Document No. 156:332918, retrieved from STN; entered in STN on Jan. 11, 2012.*
Notification of Transmittal of English Translation of International Preliminary Report on Patentability (Chapter II), dated Jul. 2, 2015, and the English Translation of the International Preliminary Report on Patentability (Chapter II) received from the International Bureau for International PCT Application No. PCT/JP2013/006916, total 8 pages.
Hayashi et al., "Rational Design of an Auxin Antagonist of the $SCF^{TIR1}$ Auxin Receptor Complex," ACS Chem. Biol., 7, pp. 590-598, 2012.
Li et al., "Exogenous Growth Hormone Attenuates Cognitive Deficits Inducted by Intermittent Hypoxia in Rats," Neuroscience, vol. 196, pp. 237-250, 2011.
Masuda et al., "Insulin-like Growth Factors and Insulin Stimulate Erythropoietin Production in Primary Cultured Astrocytes," Brain Research, vol. 746, pp. 63-70, 1997.
Tsuda et al., "Alkoxy-Auxins are Selective Inhibitors of Auxin Transport Mediated by PIN, ABCB, and AUX1 Transporters," Journal of Biological Chemistry, vol. 286, No. 3, pp. 2354-2364, Jan. 2011.
Tohoku University et al., Supplementary European Search Report for European Patent Application No. 13857636, Jul. 20, 2016, 10 pages.
Matsuhashi et al., "Mitochonic Acid 5 (MA-5) Facilitates ATP Synthase Oligomerization and Cell Survival in Various Mitochondrial Diseases," retrieved from http://www.ebiomedicine.com/action/showFullTextImages?pii=S2352-3964%2817%2930214-1, published online on May 13, 2017, 13 pages.

Moteki et al., "Hearing Loss Caused by a P2RX2 mutation identified in a MELAS family with a coexisting mitochondrial 3243AG mutation," Ann Otol Rhinol Laryngol., 124, pp. 177s-183s, 2015.
Rodriguez et al., "Beneficial Effects of Creatine, $CoQ_{10}$, and Lipoic Acid in Mitochondrial Disorders," Muscle & Nerve, pp. 235-242, 2007.
Shepherd, "Measurement of ATP Production in Mitochondrial Disorders," J. Inherit. Metab. Dis. (2006) 29: 86-91.
Suzuki et al., "Mitochonic Acid 5 (MA-5), a Derivative of the Plant Hormone Indole-3-Acetic Acid, Improves Survival of Fibroblasts from Patients with Mitochondrial Diseases," Tohoku J. Exp. Med., 2015, 236, 225-232.
English Translation of Abstract of JP 2011/190206 (Yasumitsu et al.), entitled "New Indole Derivative and Drug Use Thereof", published Sep. 29, 2011.
English Translation of Abstract of JpP2012/082181 (Abe et al.), entitled "Endogenous Erythropoietin Expression-Enhancer and Organic Ion Transporter Expression-Enhancer," published Apr. 26, 2012.
Lowy, P.H. et al., "Stimulation by Serotonin of Erythropoietin-Dependent Erythropoiesis in Mice", *British Journal of Haematology*, vol. 19, pp. 711-718, 1970.
Masuda S. et al., "Insulin-like Growth Factors and Insulin Stimulate Erythropoietin Production in Primary Cultured Astrocytes", Brain Research, vol. 746, pp. 63-70, 1997.
Mitochondrial disease treatments (online). Retrieved from the internet on Dec. 14, 2016, URL; http://www.umdf.org/what-is-mitochondrial-disease/treatments-therapies/.
Mitochondrial disease (online). Retrieved from the internet on Dec. 14, 2016, URL; http//www.medicinenet.com/mitochondrial_disease/article.htm.

* cited by examiner

[Figure 1]
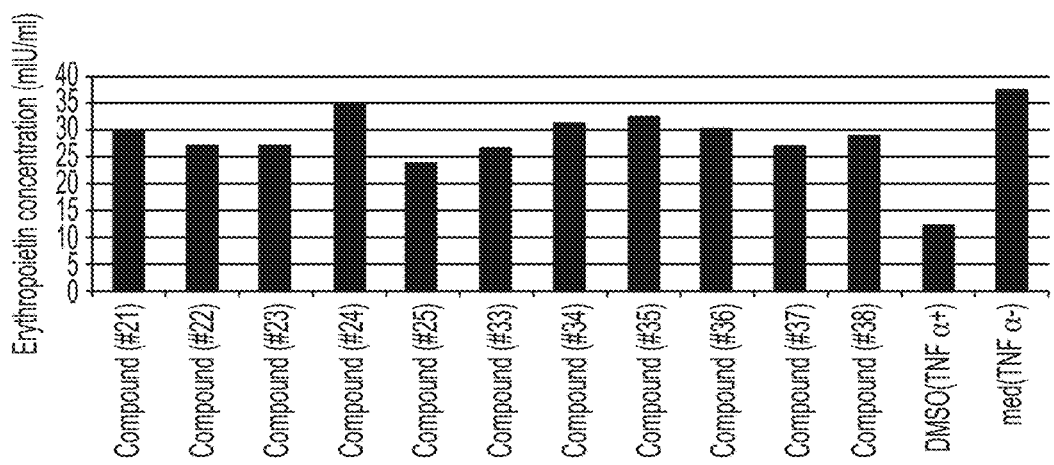
[Figure 2]
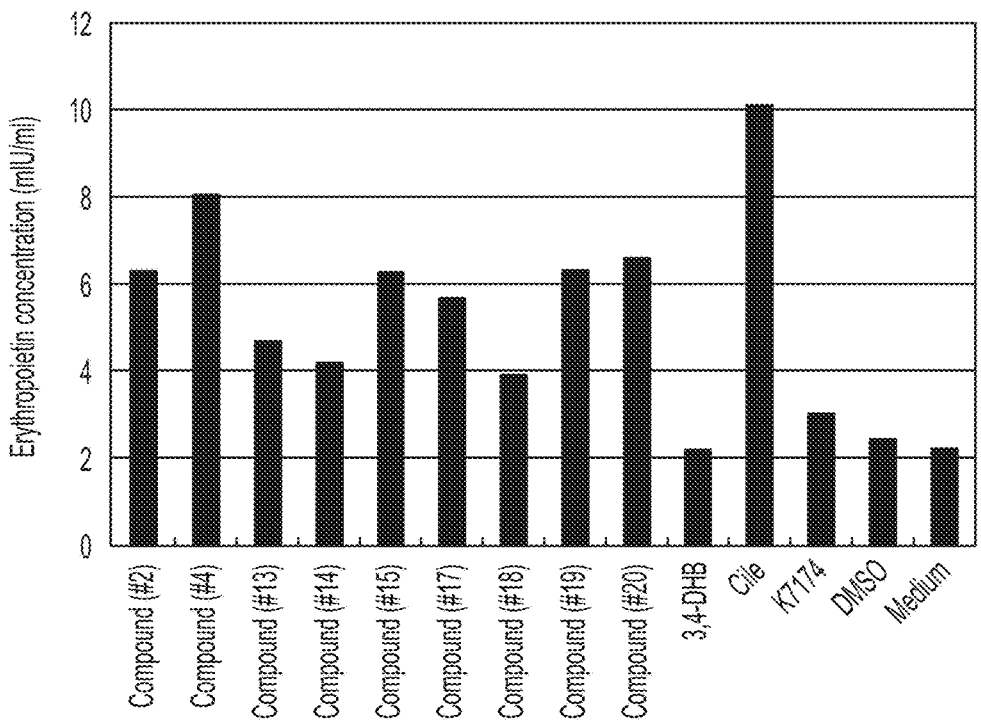

[Figure 3]
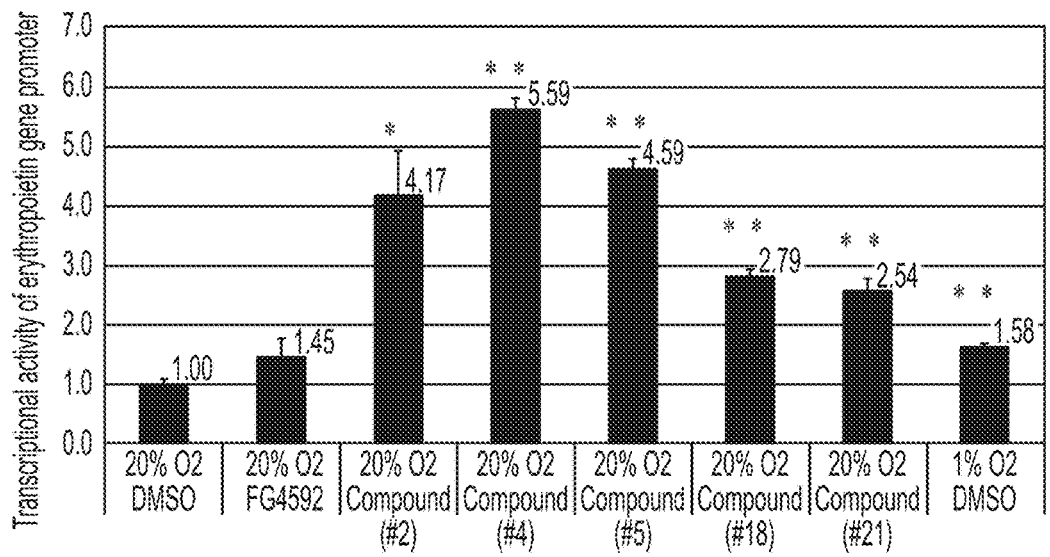
[Figure 4]
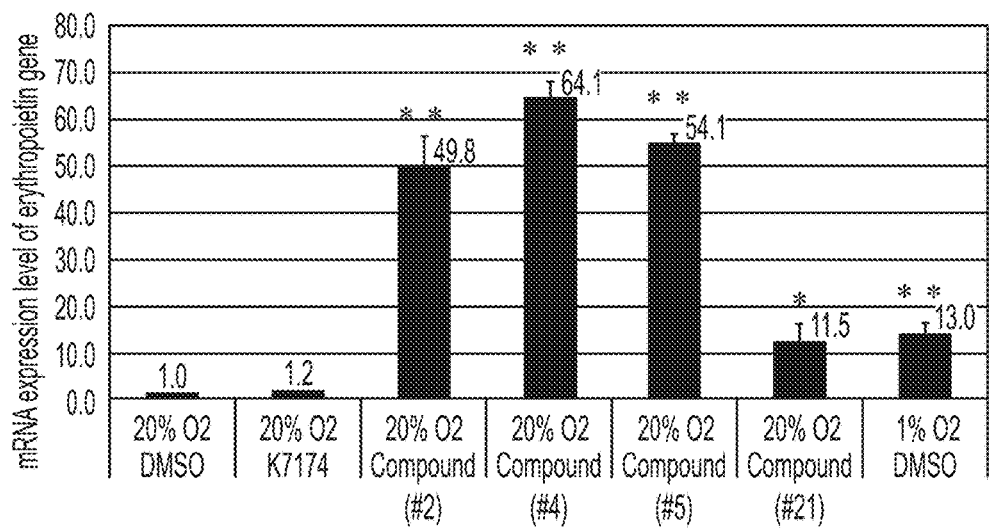

[Figure 5]
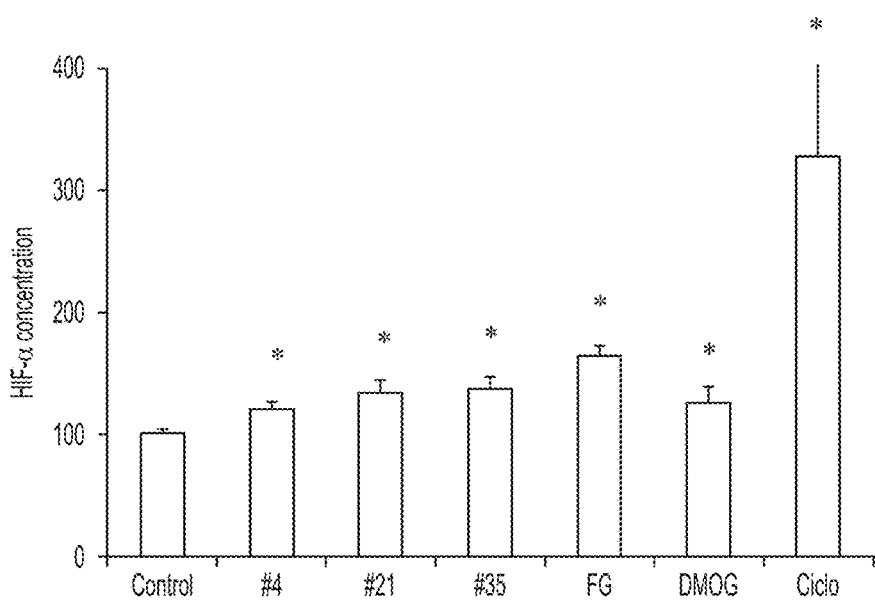
[Figure 6]
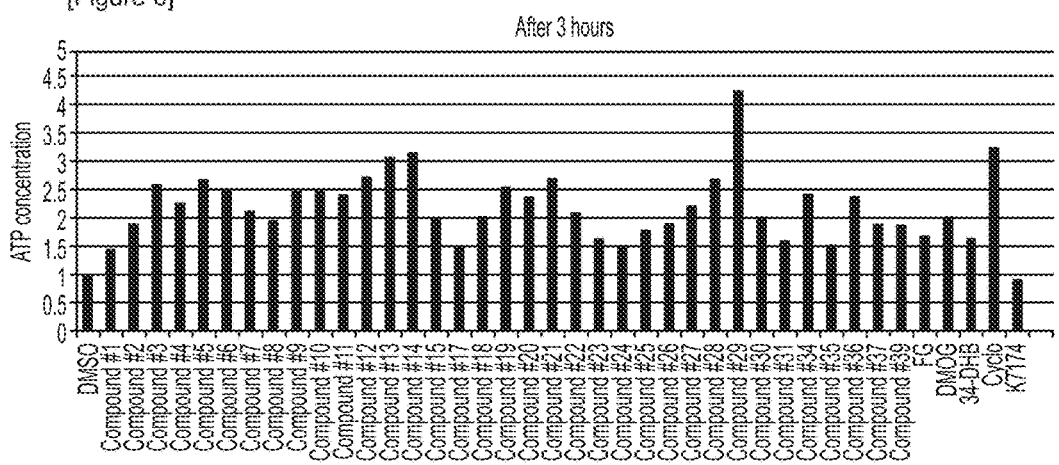

[Figure 7]
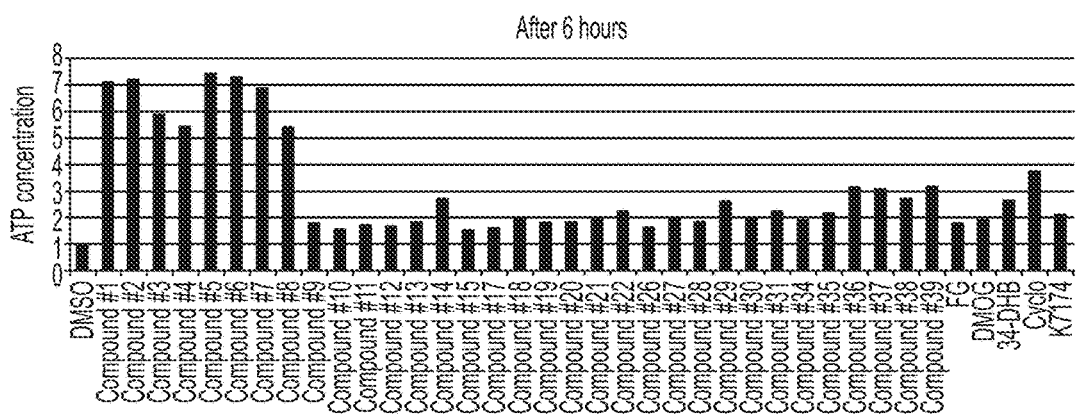
[Figure 8]
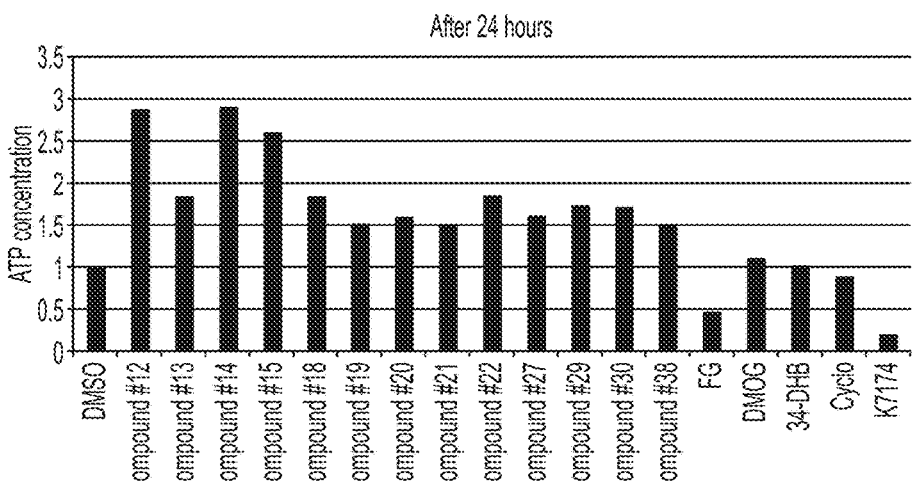

[Figure 9]
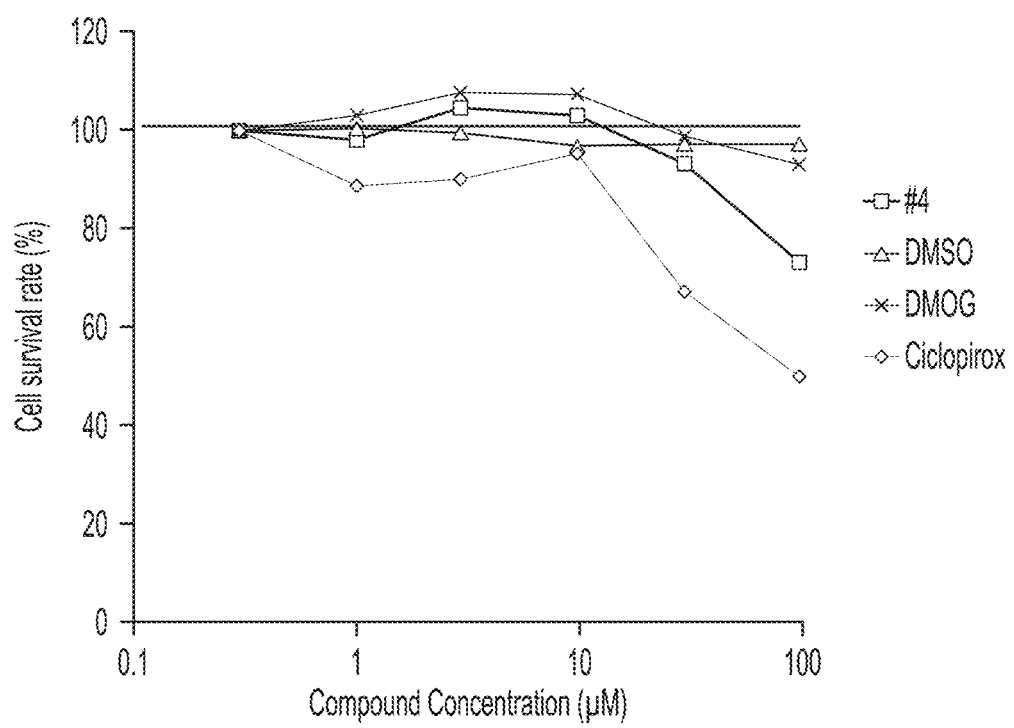

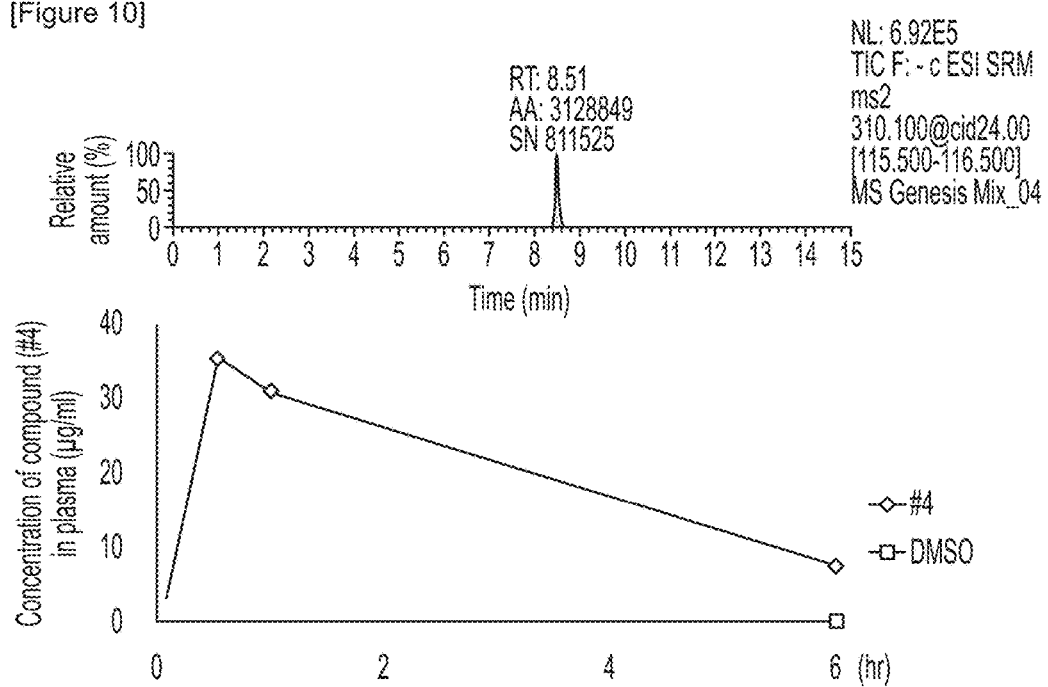
[Figure 10]

[Figure 11A]
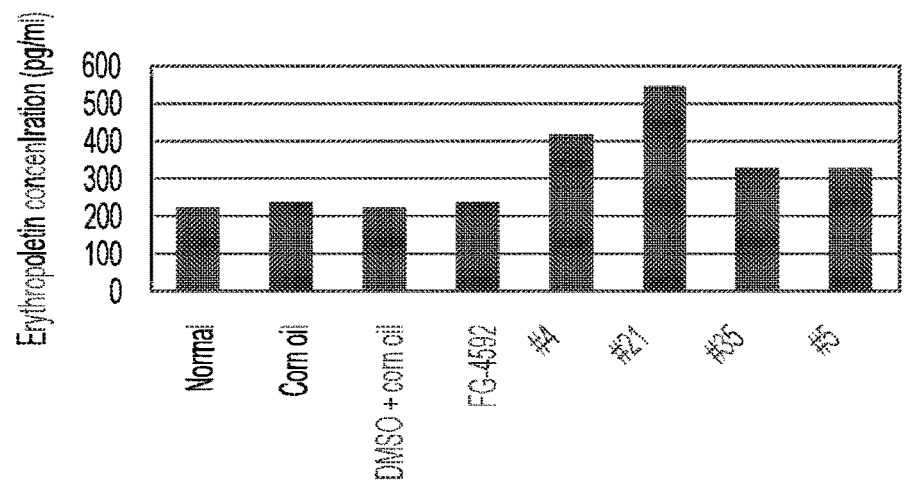
[Figure 11B]
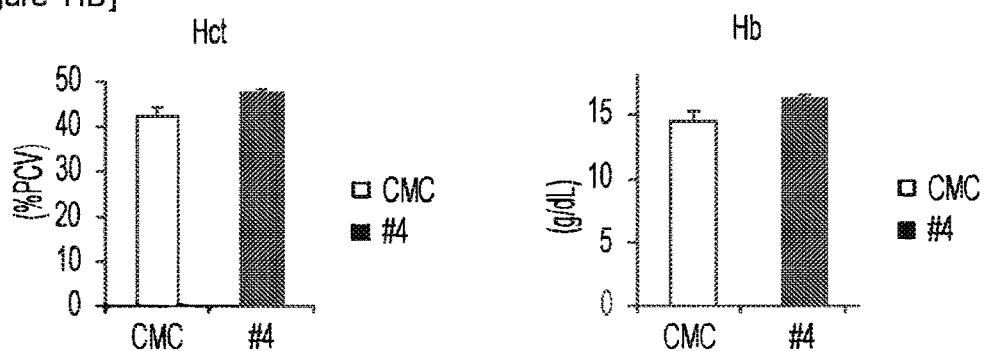

[Figure 12]
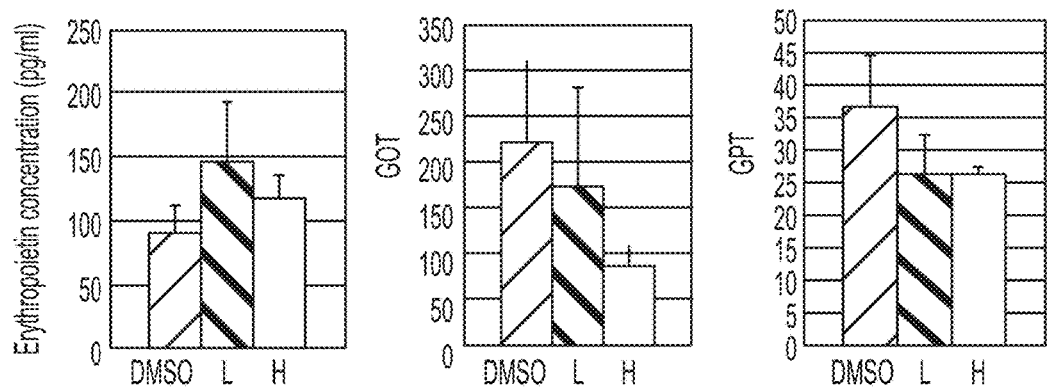
[Figure 13]
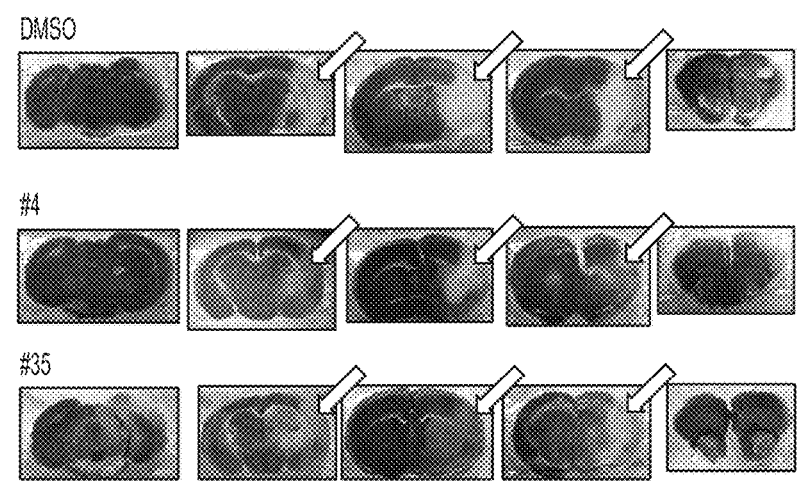

[Figure 14]
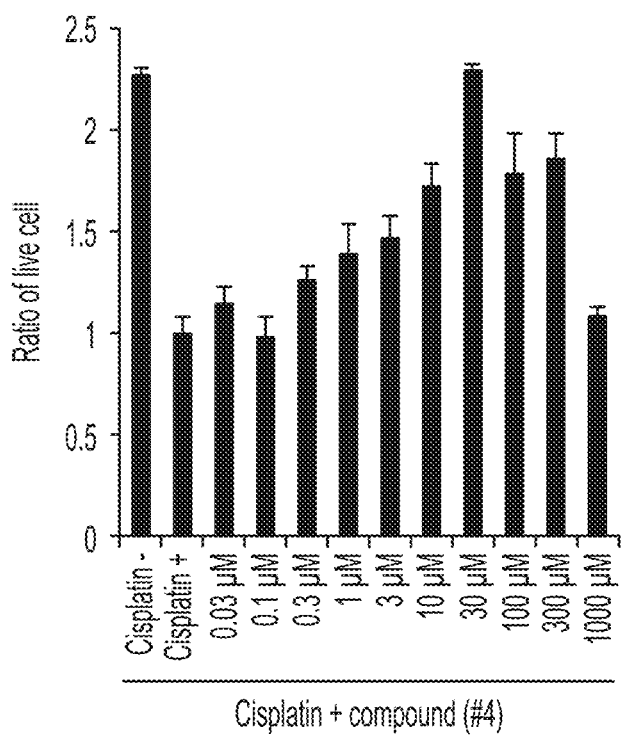

[Figure 15]
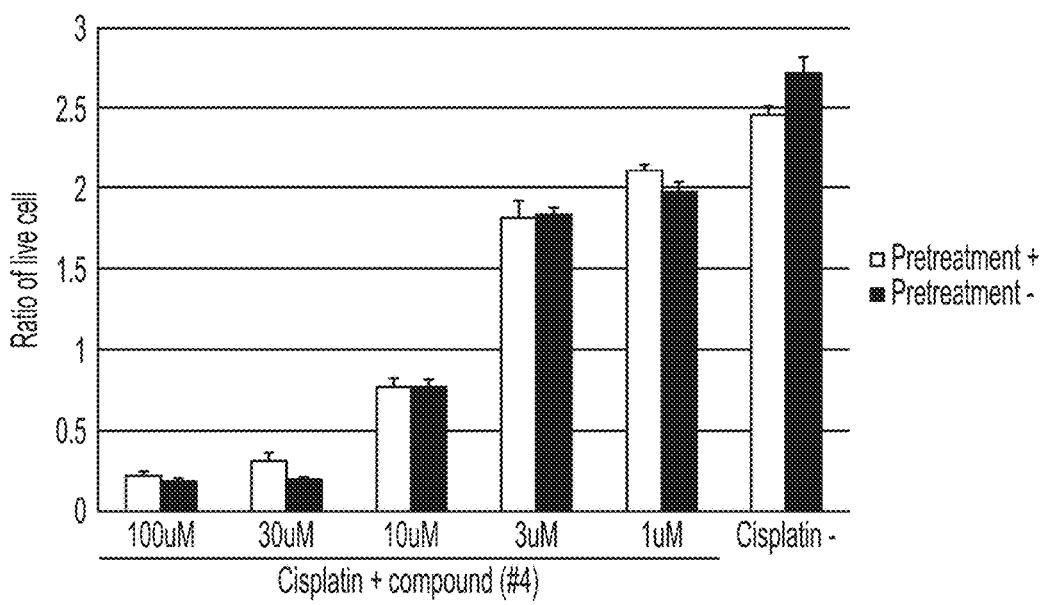
[Figure 16]
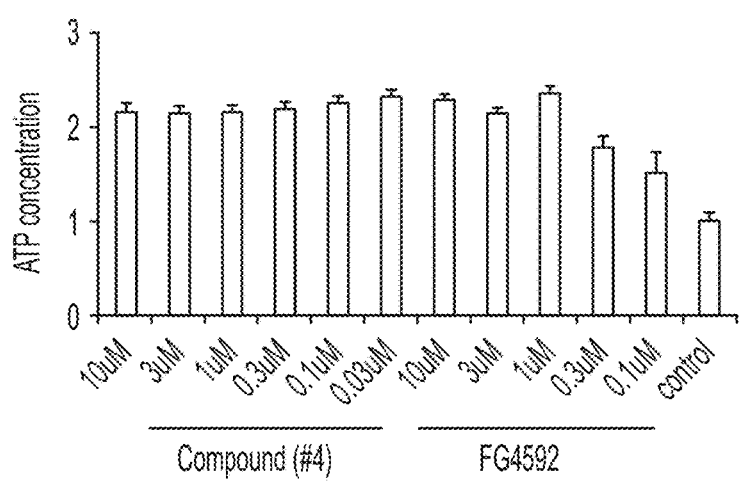

[Figure 17]
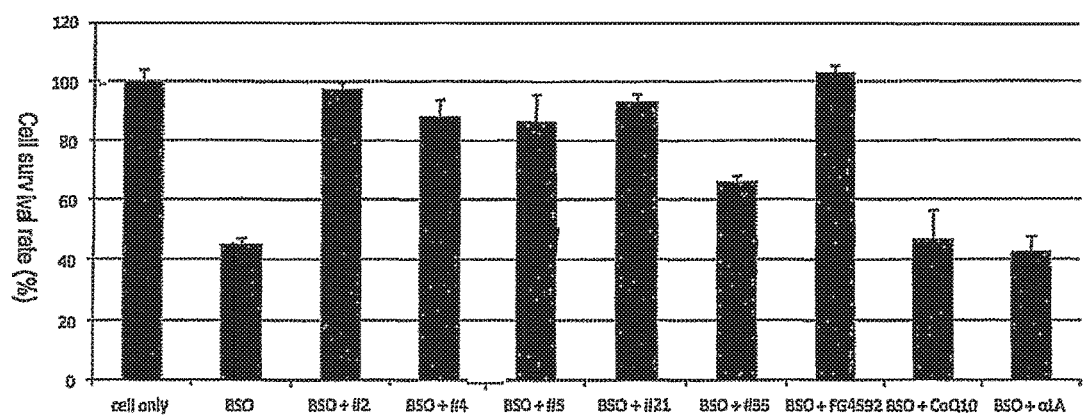

ERYTHROPOIETIN EXPRESSION PROMOTER

TECHNICAL FIELD

The present invention relates to an erythropoietin expression-enhancing agent and a therapeutic or preventive drug for anemia, a liver function-improving agent, an ischemic injury-improving agent, a renal protective agent, an insulin secretagogue, and the like comprising the erythropoietin expression-enhancing agent.

BACKGROUND ART

Erythropoietin (EPO) is a glycoprotein (hormone) that stimulates the induction of differentiation of erythroid stem cells and promotes the production of erythrocytes. Approximately 90% thereof is produced in the kidney.

Hypoxia inducible factor (HIF) is known as a factor promoting the transcription of the erythropoietin gene. HIF is a protein consisting of a heterodimer having an oxygen-regulated subunit α (HIF-α) and a constitutively expressed subunit β (HIF-β). On the other hand, GATA factors such as GATA2 and GATA3 are known as factors suppressing the transcription of the erythropoietin gene. The GATA factors are proteins binding to a GATA sequence located upstream of the erythropoietin gene. In the presence of normal oxygen, proline hydroxylase (PHD) hydroxylates proline of HIF-α, which is then degraded by ubiquitination through binding to von Hippel-Lindau (VHL). In this state, GATA3 therefore works predominantly to suppress the transcription of the erythropoietin gene. Under hypoxia, oxygen, which serves as a substrate of PHD, is insufficient. HIF-α is therefore neither hydroxylated by PHD nor degraded. In this state, HIF therefore works predominantly to promote the transcription of the erythropoietin gene.

It is known that the transcription of the erythropoietin gene is suppressed in chronic inflammations such as collagen diseases (chronic rheumatoid arthritis, systemic lupus erythematosus, etc.) and chronic infections (tuberculosis, infective endocarditis, hepatic abscess, etc.). Specifically, inflammatory cytokines such as interleukin-1β (IL1β) and tumor necrosis factor-α (TNFα) are released due to the chronic inflammations. The inflammatory cytokines thus released directly suppress erythrocyte production, while increasing the binding activity of the GATA factors, which bind to the upstream region of the erythropoietin gene, and thereby suppressing erythropoietin production. As a result, erythrocyte production is reduced so that symptoms of anemia are manifested. Also, it is known that erythropoietin production is similarly reduced in diseases such as chronic renal failure and hypothyroidism. Replacement therapy based on the administration of genetically recombinant human erythropoietin is usually used for treating anemia in such diseases or improving the symptoms of the diseases. Unfortunately, erythropoietin preparations, however, are expensive and require frequent doses of injection.

Recently, triazolopyridine compounds having a PHD inhibitory effect and the induction of erythropoietin production by these triazolopyridine compounds have been reported (patent document 1).

The present inventors have also reported that: indoxyl sulfate (IS), one of uremic toxins, promotes the expression of GATA3; and the adsorption and elimination of IS using active carbon (Kremezin) enhance the expression of endogenous erythropoietin (patent document 2).

PRIOR ART DOCUMENTS

Patent Documents

Patent Document 1: Japanese unexamined Patent Application Publication No. 2012-144571

Patent Document 2: Japanese unexamined Patent Application Publication No. 2012-82181

SUMMARY OF THE INVENTION

Object to be Solved by the Invention

An object of the present invention is [1] to provide an erythropoietin expression-enhancing agent that can cancel the suppression of erythropoietin production or promote erythropoietin production, and a therapeutic or preventive drug for anemia, a liver function-improving agent, an ischemic injury-improving agent, a renal protective agent, an insulin secretagogue, and a therapeutic agent for a mitochondrial disease comprising the erythropoietin expression-enhancing agent. Another object of the present invention is [2] to provide an ATP production-promoting agent that can promote ATP production.

Means to Solve the Object

The present inventors are continuing diligent studies to attain the object [1]. In the process, the present inventors have focused attention on the similarities between the mechanism where indole-3-acetic acid (IAA) or 1-naphthaleneacetic acid (or 1-naphthylacetic acid; NAA), which is a phytohormone called auxin, induces the ubiquitination of a transcriptional repressor AUX/IAA of an auxin-responsive gene so that AUX/IAA is degraded to thereby cancel or promote the expression of the auxin-responsive gene by a transcriptional activator ARF (auxin gene expression control mechanism) and the mechanism where a transcriptional repressor GATA3 of the erythropoietin gene is ubiquitinated so that GATA3 is degraded to thereby cancel or promote the expression of the erythropoietin gene by a transcriptional activator HIF (erythropoietin gene expression control mechanism). On the assumption that a compound that cancels or promotes the expression of the erythropoietin gene is present among indoleacetic acid derivatives or naphthylacetic acid derivatives, the present inventors have selected and synthesized 41 types of compounds from among the indoleacetic acid derivatives or the naphthylacetic acid derivatives on the basis of their long years of experience or hunch, and studied an effect of enhancing erythropoietin expression, i.e., an effect of canceling the suppression of erythropoietin production by TNFα, an effect of promoting erythropoietin production, or an effect of promoting the transcriptional activity of an erythropoietin gene promoter, by use of these compounds. As a result, 11 types of compounds (compounds #21 to 25 and 33 to 38 mentioned later in Examples) have been found to have an effect of canceling the suppression of erythropoietin production by TNFα. Also 9 types of compounds (compounds #2, 4, 13 to 15, and 17 to 20 mentioned later in Examples) have been confirmed to have a high effect of promoting erythropoietin production. Furthermore, 5 types of compounds (compounds #2, 4, 5, 18, and 21 mentioned later in Examples) have been confirmed to have a high effect of promoting the transcriptional activity of an erythropoietin gene promoter. As a result of further conducting detailed analysis using compound #4 having a particularly high effect of enhancing erythropoietin expression, the compound #4 has also been found to further have an effect of improving liver functions, an effect of improving cerebral ischemic injury, a renal protective effect, and an effect of promoting insulin secretion. Moreover, 5 types of compounds (compounds #2, 4, 5, 21, and 35 mentioned later in Examples) have also been found to be able to suppress cell death caused by oxidative stress in mitochondrial disease patients. The present invention has been completed on the basis of these findings.

Erythropoietin is known to have a protective effect against ischemic injury in organs such as the kidney and the brain. It is also known that ATP concentration is lowered at a cerebral ischemic site. In the process of diligent studies to attain the object [2], the present inventors have hypothesized that under the mechanism where erythropoietin exerts its protective effect against ischemic organ injury, intracellular ATP concentration is elevated, and conducted studies by screening for ATP production-promoting agents using the 41 types of compounds used in the screening for erythropoietin expression-enhancing agents. As a result, 36 types of compounds (compounds #1 to 15, 17 to 31, and 34 to 39 mentioned later in Examples) have been found to have a high effect of promoting ATP production. The present invention has been completed on the basis of these findings.

Specifically, the present invention relates to (1) an erythropoietin expression-enhancing agent comprising one or more compounds selected from the group consisting of a compound represented by the following formula (I):

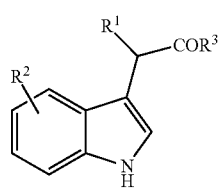

(I)

[wherein $R^1$ represents a benzoylmethyl group whose benzene ring is unsubstituted or substituted by an alkyl group having 1 to 7 carbon atoms, an alkoxyl group having 1 to 7 carbon atoms, fluorine, and/or chlorine, an unsubstituted or fluorine-substituted linear or branched alkyl group having 4 to 6 carbon atoms, or phenyl group- or cyclopentyl group-substituted methylene or ethylene, wherein the phenyl group is optionally further substituted by one or more phenyl groups, $R^2$ substituted positions 4, 5, 6, and/or 7 of indole and is selected from the group consisting of hydrogen, an alkyl group having 1 to 4 carbon atoms, an alkoxyl group having 1 to 7 carbon atoms, fluorine, and chlorine, $R^3$ represents any one group selected from OH, $OR^4$, $NHR^4$, and $NR^4R^5$, and $R^4$ and $R^5$ are the same or different and each represents a substituted or unsubstituted alkyl group having 1 to 4 carbon atoms],
the following formula (II):

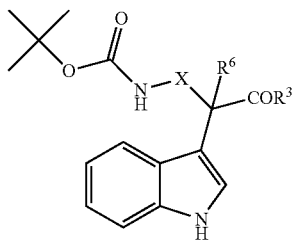

(II)

[wherein $R^6$ represents hydrogen or a methyl group, X represents an alkylene group having 4 to 6 carbon atoms or an ether group having 4 carbon atoms, $R^3$ represents any one group selected from OH, $OR^4$, $NHR^4$, and $NR^4R^5$, and $R^4$ and $R^5$ are the same or different and each represents a substituted or unsubstituted alkyl group having 1 to 4 carbon atoms], and the following formula (III):

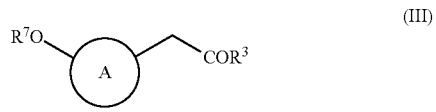

(III)

[wherein A represents indole or naphthalene, and when A is indole, positions 3 and 5 of the indole are each substituted by an acetic acid group and $R^7O$, and when A is naphthalene, positions 1 and 7 of the naphthalene are each substituted by an acetic acid group and $R^7O$, $R^7$ represents an alkyl group having 1 to 5 carbon atoms or a benzyl group, wherein the benzene ring of the benzyl group is optionally substituted by one or more alkyl groups having 1 to 3 carbon atoms or alkoxyl groups having 1 to 3 carbon atoms, $R^3$ represents any one group selected from OH, $OR^4$, $NHR^4$, and $NR^4R^5$, and $R^4$ and $R^5$ are the same or different and each represents a substituted or unsubstituted alkyl group having 1 to 4 carbon atoms], and
a pharmaceutically acceptable salt thereof when $R^3$ is OH (hereinafter, these compounds and salts are also collectively referred to as "compound group 1 of the present invention").

The present invention also relates to (2) the erythropoietin expression-enhancing agent according to (1), wherein the agent has an effect of canceling the suppression of erythropoietin expression by an inflammatory cytokine and/or an effect of promoting erythropoietin expression, (3) the erythropoietin expression-enhancing agent according to (2), wherein the inflammatory cytokine is TNFα, and (4) the erythropoietin expression-enhancing agent according to any one of (1) to (3), wherein the compound is a compound represented by the following formula (I-1), (I-2), or (III-1) (compounds #4, 21, and 35, respectively, mentioned later in Examples) or a pharmaceutically acceptable salt thereof:

Formula (I-1):

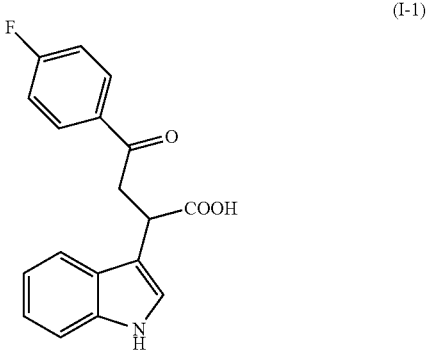 [SMILES: O=C(CC(C(=O)O)c1c[nH]c2ccccc12)c1ccc(F)cc1]

(I-1)

Formula (I-2):

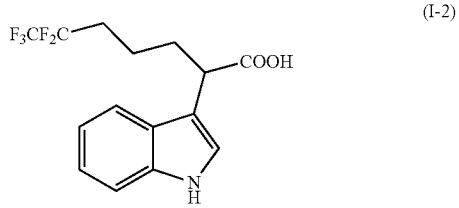

(I-2)

Formula (III-1):

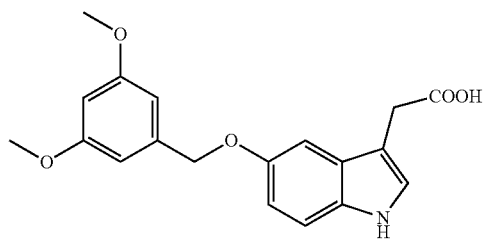

The present invention further relates to (5) a therapeutic or preventive drug for anemia comprising the erythropoietin expression-enhancing agent according to any one of (1) to (4).

The present invention further relates to (6) a liver function-improving agent comprising the erythropoietin expression-enhancing agent according to any one of (1) to (4).

The present invention further relates to (7) an ischemic injury-improving agent comprising the erythropoietin expression-enhancing agent according to any one of (1) to (4).

The present invention further relates to (8) a renal protective agent comprising the erythropoietin expression-enhancing agent according to any one of (1) to (4).

The present invention further relates to (9) an insulin secretagogue comprising the erythropoietin expression-enhancing agent according to any one of (1) to (4).

The present invention further relates to (10) a therapeutic agent for a mitochondrial disease comprising one or more compounds selected from compound group 1 of the present invention, and (11) the therapeutic agent for a mitochondrial disease according to (10), wherein the compound is a compound represented by the following formula (I-1), (I-1'''), (I-1''''), (I-2), or (III-1) or a pharmaceutically acceptable salt thereof:

Formula (I-1) (compound #4 mentioned later in Examples):

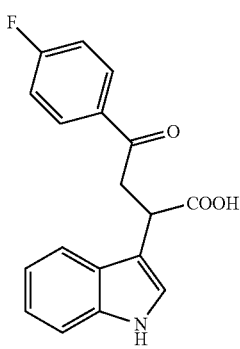

Formula (I-1''') (compound #2 mentioned later in Examples):

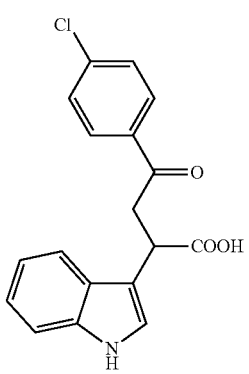

Formula (I-1'''') (compound #5 mentioned later in Examples):

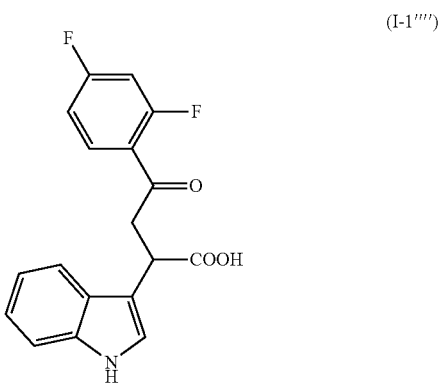 [SMILES: O=C(CC(C(=O)O)c1c[nH]c2ccccc12)c1ccc(F)cc1F]

Formula (I-2) (compound #21 mentioned later in Examples):

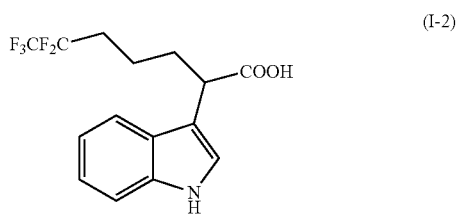

Formula (III-1) (compound #35 mentioned later in Examples):

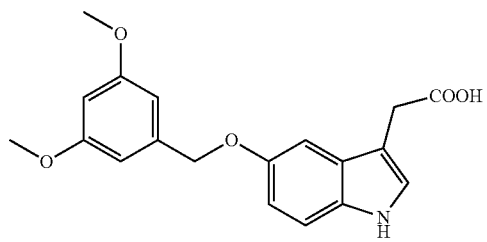

The present invention relates to (12) a compound represented by the following formula (I-1'), (I-1''), (I-2), (I-2'), (I-2''), (I-2'''), (I-3), (I-3'), (II-2), (III-1), or (IV-1) or a pharmaceutically acceptable salt thereof:

Formula (I-1') (compound #1 mentioned later in Examples):

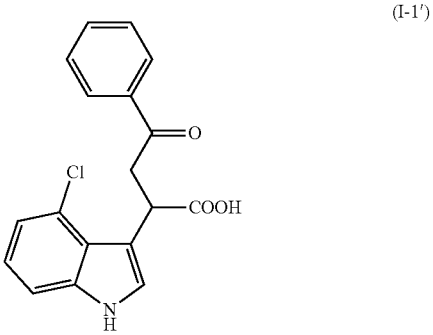 [SMILES: O=C(CC(C(=O)O)c1c[nH]c2cccc(Cl)c12)c1ccccc1]

Formula (I-1") (compound #7 mentioned later in Examples):

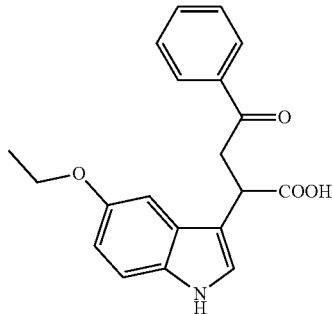

Formula (I-2) (compound #21 mentioned later in Examples):

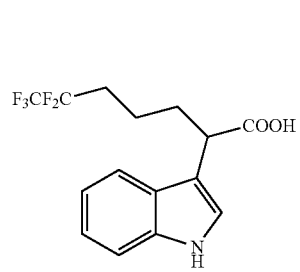

Formula (I-2') (compound #17 mentioned later in Examples):

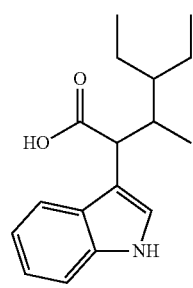

Formula (I-2") (compound #18 mentioned later in Examples):

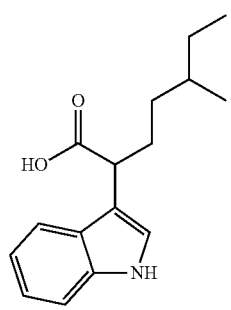

Formula (I-2''') (compound #19 mentioned later in Examples):

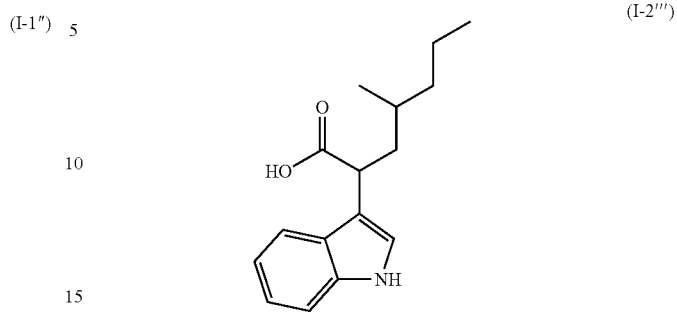

Formula (I-3) (compound #22 mentioned later in Examples):

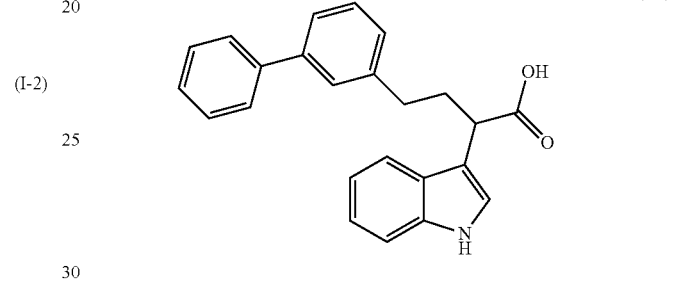

Formula (I-3') (compound #9 mentioned later in Examples):

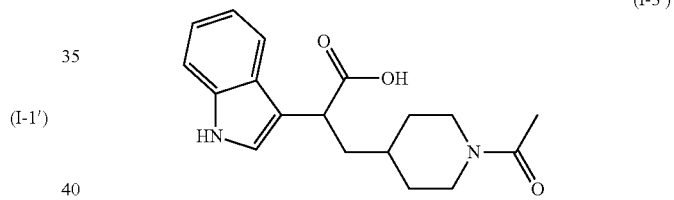

Formula (II-2) (compound #13 mentioned later in Examples):

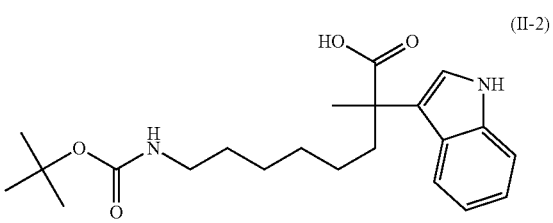 [SMILES: CC(C)(C)OC(=O)NCCCCCCC(C)(C(=O)O)c1c[nH]c2ccccc12]

Formula (III-1) (compound #35 mentioned later in Examples):

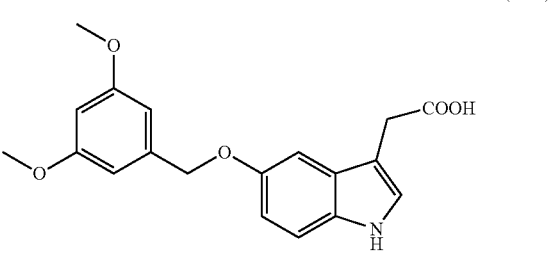

Formula (IV-1) (compound #30 mentioned later in Examples):

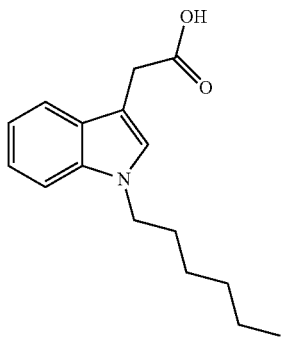

(IV-1)

An alternative embodiment of the present invention relates to, for example, a method for treating a disease such as anemia caused by reduced erythropoietin expression or reduced erythropoietin reactivity, comprising administering the erythropoietin expression-enhancing agent of the present invention to a patient in need of enhancement in erythropoietin expression, compound group 1 of the present invention for use as an erythropoietin expression-enhancing agent, and use of compound group 1 of the present invention for producing the erythropoietin expression-enhancing agent of the present invention.

An alternative embodiment of the present invention relates to, for example, a method for treating deterioration in liver function or liver dysfunction, comprising administering the erythropoietin expression-enhancing agent of the present invention to a patient in need of improvement in liver functions, compound group 1 of the present invention for use as a liver function-improving agent comprising the erythropoietin expression-enhancing agent of the present invention, and use of compound group 1 of the present invention for producing a liver function-improving agent comprising the erythropoietin expression-enhancing agent of the present invention.

An alternative embodiment of the present invention relates to, for example, a method for treating or preventing ischemic injury, comprising administering the erythropoietin expression-enhancing agent of the present invention to a patient in need of improvement in (suppression of) ischemic injury, compound group 1 of the present invention for use as an ischemic injury-improving agent comprising the erythropoietin expression-enhancing agent of the present invention, and use of compound group of the present invention for producing an ischemic injury-improving agent comprising the erythropoietin expression-enhancing agent of the present invention.

An alternative embodiment of the present invention relates to, for example, a method for treating or preventing renal damage, comprising administering the erythropoietin expression-enhancing agent of the present invention to a patient in need of protection of renal functions, compound group 1 of the present invention for use as a renal protective agent comprising the erythropoietin expression-enhancing agent of the present invention, and use of compound group 1 of the present invention for producing a renal protective agent comprising the erythropoietin expression-enhancing agent of the present invention.

An alternative embodiment of the present invention relates to, for example, a method for treating a disease caused by reduced insulin secretion or reduced insulin sensitivity, comprising administering the erythropoietin expression-enhancing agent of the present invention to a patient in need of promotion of insulin secretion, compound group 1 of the present invention for use as an insulin secretagogue comprising the erythropoietin expression-enhancing agent of the present invention, and use of compound group 1 of the present invention for producing an insulin secretagogue comprising the erythropoietin expression-enhancing agent of the present invention.

An alternative embodiment of the present invention relates to, for example, a method for treating a mitochondrial disease, comprising administering the therapeutic agent for a mitochondrial disease of the present invention to a patient in need of treatment of the mitochondrial disease, compound group 1 of the present invention for use as the therapeutic agent for a mitochondrial disease of the present invention, and use of compound group 1 of the present invention for producing the therapeutic agent for a mitochondrial disease of the present invention.

An alternative embodiment of the present invention relates to, for example, [1] an ATP expression-promoting agent comprising one or more compounds selected from the group consisting of compounds represented by the following formula (i):

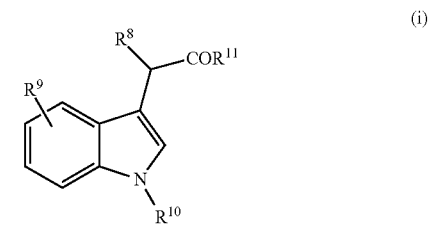

(i)

[wherein $R^8$ represents a benzoylmethyl group whose benzene ring is unsubstituted or substituted by an alkyl group having 1 to 7 carbon atoms, an alkoxyl group having 1 to 7 carbon atoms, fluorine, and/or chlorine, an unsubstituted or fluorine-substituted linear or branched alkyl group having 4 to 6 carbon atoms, or 4-N-acetylpiperidinyl group-, phenyl group-, or cyclopentyl group-substituted methylene or ethylene, wherein the phenyl group is optionally further substituted by one or more phenyl groups, $R^9$ is selected from the group consisting of hydrogen, an alkyl group having 1 to 4 carbon atoms, an alkoxyl group having 1 to 4 carbon atoms, fluorine, and chlorine, $R^{10}$ represents hydrogen or a linear or branched alkyl group having 1 to 3 carbon atoms, $R^{11}$ represents any one group selected from OH, $OR^{12}$, $NHR^{12}$, and $NR^{12}R^{13}$, and $R^{12}$ and $R^{13}$ are the same or different and each represents a substituted or unsubstituted alkyl group having 1 to 4 carbon atoms],
the following formula (ii):

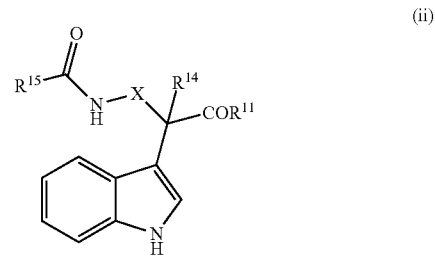

(ii)

[wherein R[14] represents hydrogen or a methyl group, X represents an alkylene group having 4 to 6 carbon atoms or an ether group having 4 carbon atoms, R[15] represents a tert-butoxy group or a 2-N-acetylpyrrolidinyloxy group, R[11] represents any one group selected from OH, OR[12], NHR[12], and NR[12]R[13], and R[12] and R[13] are the same or different and each represents a substituted or unsubstituted alkyl group having 1 to 4 carbon atoms], the following formula (iii):

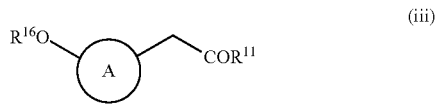

(iii)

[wherein A represents indole or naphthalene, and when A is indole, positions 3 and 5 of the indole are each substituted by an acetic acid group and R[16]O, and when A is naphthalene, positions 1 and 7 of the naphthalene are each substituted by an acetic acid group and R[16]O, R[16] represents a linear or branched alkyl group having 1 to 7 carbon atoms or a benzyl group, wherein the benzene ring of the benzyl group is optionally substituted by one or more alkyl groups having 1 to 3 carbon atoms or alkoxyl groups having 1 to 3 carbon atoms, R[11] represents any one group selected from OH, OR[12], NHR[12], and NR[12]R[13], and R[12] and R[13] are the same or different and each represents a substituted or unsubstituted alkyl group having 1 to 4 carbon atoms], the following formula (iv):

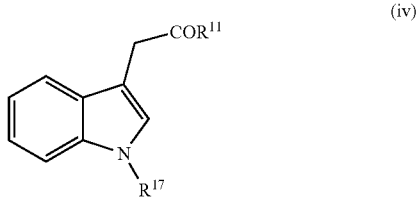

(iv)

[wherein R[17] represents a linear alkyl group having 1 to 7 carbon atoms, R[11] represents any one group selected from OH, OR[12], NHR[12], and NR[12]R[13], and R[12] and R[13] are the same or different and each represents a substituted or unsubstituted alkyl group having 1 to 4 carbon atoms], the following formula (v):

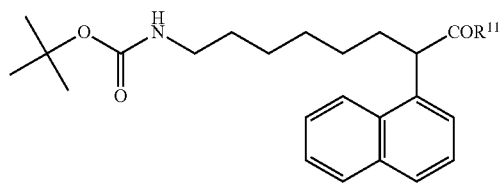

(v)

[wherein R[11] represents any one group selected from OH, OR[12], NHR[12], and NR[12]R[13], and R[12] and R[13] are the same or different and each represents a substituted or unsubstituted alkyl group having 1 to 4 carbon atoms], and the following (vi) (compound #3 mentioned later in Examples):

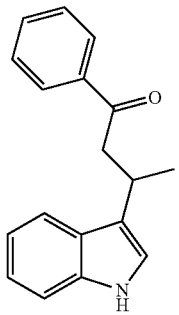

(vi)

and a pharmaceutically acceptable salt thereof when R[11] is OH (hereinafter, these compounds and salts are also collectively referred to as "compound group 2 of the present invention").

An alternative embodiment of the present invention relates to, for example, a method for treating a disease caused by reduced ATP production, comprising administering the ATP production-promoting agent of the present invention to a patient in need of ATP production, compound group 2 of the present invention for use as the ATP production-promoting agent, and use of compound group 2 of the present invention for producing the ATP production-promoting agent.

Effect of the Invention

The erythropoietin expression-enhancing agent of the present invention can cancel the suppression of the amount of erythropoietin produced by living tissues of the kidney, the liver, or the like or enhance the amount of erythropoietin produced by such living tissues, and can treat or prevent anemia associated with a disease caused by reduced erythropoietin production or reduced erythropoietin reactivity. In addition, the erythropoietin expression-enhancing agent of the present invention can improve deterioration in liver function, improve ischemic injury, improve renal damage, and promote insulin secretion. The therapeutic agent for a mitochondrial disease of the present invention can also suppress cell death caused by oxidative stress in patients with a mitochondrial disease such as Leigh syndrome and treat the mitochondrial disease. Furthermore, the ATP production-promoting agent according to an alternative embodiment of the present invention can enhance the amount of ATP produced by living tissues of the kidney, the liver, or the like and treat or prevent a disease caused by reduced ATP production, such as hyperammonemia.

BRIEF DESCRIPTION OF DRAWINGS

FIG. 1 is a diagram showing that in an erythropoietin-producing human liver cell line Hep3B, the compounds #21 to 25 and 33 to 38 of the present invention cancel the suppression of erythropoietin production by TNFα.

FIG. 2 is a diagram showing that in a Hep3B cell line, the compounds #2, 4, 13 to 15, and 17 to 20 of the present invention enhance the amount of erythropoietin produced.

FIG. 3 is a diagram showing that in a Hep3B cell line, the compounds #2, 4, 5, 18, and 21 of the present invention promote the transcriptional activity of an erythropoietin gene promoter. The ordinate depicts a relative ratio with the results about "20% O2/DMSO" (transcriptional activity of the erythropoietin gene promoter) defined as 1.

FIG. 4 is a diagram showing that in a Hep3B cell line, the compounds #2, 4, 5, and 21 of the present invention enhance the mRNA expression of the erythropoietin gene. The ordinate depicts a relative ratio with the results about "20% O2/DMSO" (mRNA expression level of the erythropoietin gene) defined as 1.

FIG. 5 is a diagram showing that in a Hep3B cell line, the compounds #4, 21, and 35 of the present invention enhance the amount of HIF-α produced. The ordinate depicts a relative ratio with the results about "Control" (HIF-α concentration) defined as 100.

FIG. 6 is a diagram showing that in a Hep3B cell line, the compounds #1 to 15, 17 to 31, and 34 to 38 enhance the amount of ATP produced. The ordinate depicts a relative ratio with the results about "DMSO" (ATP concentration) defined as 1.

FIG. 7 is a diagram showing that in a Hep3B cell line, the compounds #1 to 15, 17 to 22, 26 to 31, and 34 to 39 enhance the amount of ATP produced. The ordinate depicts a relative ratio with the results about "DMSO" (ATP concentration) defined as 1.

FIG. 8 is a diagram showing that in a Hep3B cell line, the compounds #12 to 15, 18 to 22, 27, 29, 30, and 38 enhance the amount of ATP produced. The ordinate depicts a relative ratio with the results about "DMSO" (ATP concentration) defined as 1.

FIG. 9 is a diagram showing results of examining cytotoxicity by the addition of the compound #4 of the present invention to a Hep3B cell line. In the diagram, "#4" represents the compound #4. The ordinate depicts a relative ratio with the cell survival rate at the concentration 0.5 µM of each compound (compound #4, dimethyloxalylglycine (DMOG), and ciclopirox) defined as 100.

FIG. 10 is a diagram showing that in mice, the compound #4 of the present invention is absorbed into the body. The upper column of FIG. 10 shows results of detecting the compound #4 in plasma separated using an analytical column, as an MS spectral peak by LC/MS/MS. The lower column of FIG. 10 is a diagram showing results of calculating the concentration of the compound #4 in the plasma from this peak.

FIG. 11A is a diagram showing that in mice, the compounds #4, 5, 21, and 35 of the present invention enhance the amount of erythropoietin produced.

FIG. 11B is a diagram showing that in mice, the compound #4 of the present invention increases erythrocyte concentration in blood. The left diagram shows results of measuring a volume ratio of blood cell components in blood to the whole blood (% PCV [packed cell volume]), i.e., a hematocrit (Hct) value (mean±standard deviation, [n=3]). The right diagram shows results of measuring hemoglobin concentration (g/dL) in blood (mean±standard deviation, [n=3]). In the diagram, "#4" represents a compound #4 administration group, and "CMC" represents a CMC (carboxymethylcellulose) administration group as a control.

FIG. 12 is a diagram showing that in mice, the compound #4 of the present invention improves liver functions. In the diagram, "DMSO" represents a DMSO administration group, "L" represents a low-concentration (5 µg/ml) compound (#4) administration group, and "H" represents a high-concentration (15 µg/ml) compound (#4) administration group. In the ordinate, "GOT" and "GPT" each represents a unit of activity (Karmen unit [KU]).

FIG. 13 is a diagram showing that in mice, the compounds #4 and 35 of the present invention improve cerebral ischemic injury. The photographs show a DMSO administration group, a compound #4 administration group, and a compound #35 administration group in order from top to bottom. For each group, coronal sections of the cerebrum (5 sections) were stained with 2,3,5-triphenyltetrazolium chloride (TTC), and their photographs are shown. In the diagram, the arrow represents a cerebral infarction site.

FIG. 14 is a diagram showing that in a human kidney-derived cell line HK-2, the compound #4 of the present invention cancels the nephrotoxicity of a drug such as cisplatin. The ordinate depicts a relative ratio with the results about "Cisplatin+" (ratio of live cells) defined as 1.

FIG. 15 is a diagram showing that in a human kidney-derived cell line HK-2, the preincubation of the compound #4 of the present invention enhances its effect of canceling the nephrotoxicity of a drug such as cisplatin. The ordinate depicts a measurement value of absorbance at OD 450 mm. In the diagram, the right graph for each sample represents "Pretreatment-", and the left graph represents "Pretreatment+".

FIG. 16 is a diagram showing that in a rat islet of Langerhans-derived cell line ISN-1e, the compound #4 of the present invention enhances the amount of ATP produced (stimulates insulin secretion). The ordinate depicts a relative ratio with the results about "DMSO" (ATP concentration) defined as 1.

FIG. 17 is a diagram showing results of analyzing a cell survival rate of Leigh syndrome patient-derived skin fibroblast cells (Leigh cells) treated with a glutathione synthesis inhibitor BSO (L-buthionine sulphoximine) and then cultured in the presence of the compounds #2, 4, 5, 21, and 35. The ordinate depicts a relative ratio with the cell survival rate of control Leigh cells cultured in the absence of the compound and BSO defined as 100.

MODE OF CARRYING OUT THE INVENTION

The erythropoietin expression-enhancing agent of the present invention has an effect of enhancing the expression (production) of erythropoietin in erythropoietin-secreting tissues of the kidney, the liver, or the like. The effect of enhancing erythropoietin expression is preferably an effect of canceling the suppression of erythropoietin expression by an inflammatory cytokine or an effect of promoting erythropoietin expression. In this context, the promotion of erythropoietin expression refers to the promotion (increase) of the transcription of the erythropoietin gene into mRNA or the expression of the erythropoietin protein at least under normal oxygen (18 to 22% $O_2$) conditions. The suppression of erythropoietin expression by an inflammatory cytokine typically means that erythropoietin production is promoted under hypoxia (0 to 10% $O_2$) conditions, but this promoting effect is suppressed by the action of the inflammatory cytokine. The effects of the erythropoietin expression-enhancing agent of the present invention can cancel the suppression of the promoting effect and enhance (increase) the transcription of the erythropoietin gene into mRNA or the expression of the erythropoietin protein.

Examples of the mechanism of action of canceling the suppression of erythropoietin expression or promoting erythropoietin expression as mentioned above can include a mechanism of action where erythropoietin expression is enhanced by canceling the suppression of erythropoietin production as a result of, for example, suppressing the expression of GATA factors such as GATA2 and GATA3 or inhibiting the binding of the GATA factors to a GATA sequence present in the erythropoietin gene, and a mechanism of action where erythropoietin expression is enhanced by promoting the transcriptional activity of an erythropoietin gene promoter as a result of, for example, inhibiting the degradation of HIF-α or promoting HIF production.

The inflammatory cytokine is not particularly limited as long as the inflammatory cytokine has an effect of suppressing erythropoietin expression. Specific examples thereof can include interleukin-1 (IL1), IL6, IL8, IL12, IL18, tumor necrosis factor-α (TNFα), and interferon-γ (IFNγ). Among them, TNFα is preferred.

The therapeutic agent for a mitochondrial disease of the present invention has an effect of suppressing cell death caused by oxidative stress in mitochondrial disease patients and as such, is particularly preferably an oxidative stress-suppressing agent for a mitochondrial disease. The mitochondrial disease can be any symptom caused by reduction in mitochondrial functions such as ATP production, apoptosis regulation, and regulation of intracellular concentration of calcium ions or iron due to gene mutation or the like in cellular nuclear DNA or mitochondrial DNA. Specific examples thereof can include CPEO (chronic progressive external ophthalmoplegia), MELAS (mitochondrial encephalomyopathy, lactic acidosis, and stroke-like episodes), MERRF (myoclonus epilepsy with ragged-red fibers), Leigh syndrome (subacute necrotizing encephalomyelopathy), Leber's disease, Pearson's disease, and Friedreich's ataxia (FRDA). Among them, Leigh syndrome is preferred.

The ATP production-promoting agent of an alternative embodiment has an effect of promoting (enhancing) ATP production (expression) in living tissues of the kidney, the liver, or the like. The effect of promoting ATP production includes an effect of promoting (enhancing) the production (expression) of, for example, an enzyme acting in the glycolytic system, such as triose phosphate isomerase, enolase, phosphoglucomutase, or hexokinase, or an enzyme acting in the electron transport system, such as ATP synthase, cytochrome c oxidase, or flavoprotein.

The erythropoietin expression-enhancing agent or the therapeutic agent for a mitochondrial disease of the present invention is not particularly limited as long as the agent contains one or more compounds selected from compound group 1 of the present invention as active ingredients. Hereinafter, each compound included in the compound group 1 of the present invention will be described in detail.

In one aspect of the present invention, $R^1$ in the formula (I) is a benzoylmethyl group whose benzene ring is unsubstituted or substituted by an alkyl group having 1 to carbon atoms, an alkoxyl group having 1 to 4 carbon atoms, fluorine, and/or chlorine. The benzene ring of this benzoylmethyl group is optionally substituted. Examples of the substituted benzoylmethyl group can include a benzoylmethyl group having 1 to 5 alkyl groups having 1 to 7 carbon atoms, 1 to 5 alkoxyl groups having 1 to 7 carbon atoms, 1 to 5 fluorine atoms, or 1 to 5 chlorine atoms on the benzene ring or having 1 to 5 substituents in total of an alkyl group having 1 to 4 carbon atoms, an alkoxyl group having 1 to 4 carbon atoms, a fluorine atom, and a chlorine atom on the benzene ring. In this context, examples of the alkyl group having 1 to 7 carbon atoms can include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4,4-dimethylpentyl group, and a 1-propylbutyl group.

Examples of the alkoxyl group having 1 to 7 carbon atoms can include a methoxy group, an ethoxy group, a propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, and a 1-propylbutoxy group.

In an alternative aspect of the present invention, $R^1$ in the formula (I) is an unsubstituted or fluorine-substituted linear or branched alkyl group having 4 to 6 carbon atoms. Examples of the unsubstituted or fluorine-substituted linear or branched alkyl group having 4 to 6 carbon atoms can include a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, and fluorinated forms thereof. The unsubstituted or fluorine-substituted linear or branched alkyl group having 4 to 6 carbon atoms is preferably a 1-ethylbutyl group, a 2-ethylbutyl group, a 1-methylpentyl group, a 2-methylpentyl group, a 3-methylpentyl group, a 4-methylpentyl group, a 5-methylpentyl group, a 3,3,4,4,4-pentafluorobutyl group, a 4,4,5,5,5-pentafluoropentyl group, or a 5,5,6,6,6-pentafluorohexyl group, more preferably a 2-ethylbutyl group, a 2-methylpentyl group, a 3-methylpentyl group, or a 4,4,5,5,5-pentafluoropentyl group, most preferably a 4,4,5,5,5-pentafluoropentyl group.

In an alternative aspect of the present invention, $R^1$ in the formula (I) is phenyl group- or cyclopentyl group-substituted methylene or ethylene. The phenyl group is optionally further substituted by one or more phenyl groups. The phenyl group- or cyclopentyl group-substituted methylene or ethylene is a benzyl group, a 2-phenethyl group, a cyclopentylmethyl group, or a 2-cyclopentylethyl group. Examples of the benzyl group or the 2-phenethyl group substituted by one or more phenyl groups can include a 3-phenylbenzyl group, a 4-phenylbenzyl group, a 3,5-diphenylbenzyl group, a 2-(1,1'-biphenyl-3-yl)-ethyl group, a 2-(1,1'-biphenyl-4-yl)-ethyl group, and a 2-(3,5-diphenylphenyl)-ethyl group. Preferred examples of $R^1$ in the formula (I) can include a 2-phenethyl group, a cyclopentylmethyl group, a 2-cyclopentylethyl group, and a 2-(1,1'-biphenyl-3-yl)-ethyl group.

$R^2$ in the formula (I) is a group that optionally substitutes positions 4, 5, 6, and/or 7 of the indole skeleton. One or more $R^2$ can be added to each replaceable position. Examples of $R^2$ can include an alkyl group having 1 to 4 carbon atoms, an alkoxyl group having 1 to 7 carbon atoms, fluorine, and chlorine. Examples of the alkyl group having 1 to 4 carbon atoms can include a methyl group, an ethyl group, a propyl group, an isopropyl group, a n-butyl group, an isobutyl group, a sec-butyl group, and a tert-butyl group. Examples of the alkoxyl group having 1 to 7 carbon atoms can include a methoxy group, an ethoxy group, a propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, and a 1-propylbutoxy group. $R^2$ is preferably hydrogen, an ethoxy group, fluorine, or chlorine.

$R^4$ and $R^5$ in the formula (I) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (I) wherein $R^1$ is a 4-difluorobenzoylmethyl group, $R^2$ is hydrogen, and $R^3$ is OH represents compound #4 mentioned later in Examples. The compound represented by the formula (I) wherein $R^1$ is a 4,4,5,5,5-pentafluoropentyl group, $R^2$ is hydrogen, and $R^3$ is OH represents compound #21 mentioned later in Examples. The compound represented by the formula (I) wherein $R^1$ is a 2-cyclopentylethyl group, $R^2$ is hydrogen, and $R^3$ is OH represents compound #24 mentioned later in Examples. In addition to these compounds, specific examples of the compound represented by the formula (I) can include compounds #2, 4, 5, and 20 mentioned later in Examples, compounds #17 to 19 mentioned later in Examples, compounds #22 and 23 mentioned later in Examples, and compound #25 mentioned later in Examples.

X in the formula (II) is a linear alkylene group having 4 to 6 carbon atoms, i.e., butylene —(CH$_2$)$_4$—, pentylene —(CH$_2$)$_5$—, or hexylene —(CH$_2$)$_6$—, or an ether group having 4 carbon atoms. Examples of the ether group having 4 carbon atoms can include a methylene-O-propylene group, an ethylene-O-ethylene group, and a propylene-O-methylene group. X is preferably butylene, hexylene, or an ethylene-O-ethylene group.

$R^4$ and $R^5$ in the formula (II) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (II) wherein X is butylene, $R^6$ is hydrogen, and $R^3$ is OH represents compound #15 mentioned later in Examples. In addition to the compound #15, specific examples of the compound represented by the formula (I) can include compound #13 mentioned later in Examples and compound #14 mentioned later in Examples.

$R^7$ in the formula (III) is an alkyl group having 1 to 5 carbon atoms or a benzyl group. Examples of the linear or branched alkyl group having 1 to 5 carbon atoms can include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, and a 2,2-dimethylpropyl group. The benzene ring of the benzyl group is optionally substituted by one or more alkyl groups having 1 to 3 carbon atoms or alkoxyl groups having 1 to 3 carbon atoms. Examples of the alkyl group having 1 to 3 carbon atoms can include a methyl group, an ethyl group, a n-propyl group, and an isopropyl group. Examples of the alkoxy group having 1 to 3 carbon atoms can include a methoxy group, an ethoxy group, a n-propoxy group, and an isopropoxy group. $R^7$ in the formula (III) is preferably a methyl group, an ethyl group, a propyl group, a n-butyl group, a n-pentyl group, or a 3,5-dimethoxybenzyl group, more preferably a 3,5-dimethoxybenzyl group.

$R^4$ and $R^5$ in the formula (III) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^4$ and $R^5$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2,2,2-trichloromethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (III) wherein A is indole, $R^7$ is a 3,5-dimethoxybenzyl group, and $R^3$ is OH represents compound #35 mentioned later in Examples. In addition to the compound #35, specific examples of the compound represented by the formula (I) can include compounds #36 to 38 mentioned later in Examples and compounds #33 and 34 mentioned later in Examples.

When a compound selected from compound group 1 of the present invention has an asymmetric carbon atom and an axial chirality-related asymmetric point, this compound includes all possible optical isomers. These optical isomers can be used at an arbitrary ratio. For example, a certain optically active compound can be used as an enantiomer, a racemate, or an enantiomer mixture at an arbitrary ratio. A compound containing a plurality of asymmetric points can be used as a diastereomer mixture at an arbitrary ratio.

The pharmaceutically acceptable salts of compound group 1 of the present invention include, for example, metal salts formed from aluminum, calcium, lithium, magnesium, potassium, sodium, and zinc, and organic salts formed from N,N'-dibenzylethylenediamine, chloroprocaine, choline, diethanolamine, ethylenediamine, N-methylglucamine, lysine, procaine, and the like.

Exemplary methods for synthesizing each compound selected from compound group 1 of the present invention will be given below. However, the synthesis methods of the present invention are not limited to these methods, and generally known synthesis methods can be used. Compounds shown below can be obtained from Sigma-Aldrich Corp., Tokyo Chemical Industry Co., Ltd., Wako Pure Chemical Industries, Ltd., Kanto Chemical Co., Inc., etc. As for reaction solvents and reaction temperatures, a reaction is carried out using a solvent and a temperature usually used for the reaction, unless otherwise specified. Each reaction is carried out in an argon or nitrogen atmosphere. Each protective group can be used with reference to Green & Wuts, "PROTECTIVE GROUPS in ORGANIC SYNTHESIS" 3rd ed. John Wiley & Sons, Inc.

The compound represented by the formula (I) can be synthesized from substituted or unsubstituted benzene and substituted or unsubstituted indole as starting materials. First, substituted or unsubstituted benzene and maleic anhydride are used in Friedel-Crafts reaction to synthesize 4-aryl-4-oxo-2-butenoic acid. This Friedel-Crafts reaction is carried out by the action of a catalyst such as Lewis acid, phosphoric acid, or polyphosphoric acid. Aluminum chloride is preferably used as the catalyst. The reaction solvent is preferably a chlorine solvent. Alternatively, the starting material substituted or unsubstituted benzene can also be used as a solvent. The 4-aryl-4-oxo-2-butenoic acid thus obtained and substituted or unsubstituted indole are subjected to Michael reaction to obtain a compound in which the α-position of indoleacetic acid is substituted by a substituted or unsubstituted benzoyloxy group. In this way, the basic skeleton of the compound represented by the formula (I) can be constructed. In this Michael reaction, the carboxyl group of the 4-aryl-4-oxo-2-butenoic acid can or cannot be protected and, usually, does not have to be protected. When this carboxyl group is protected, examples of the protective group used can include methyl ester, tert-butyl ester, 2,2,2-trichloroethyl ester, and tert-butyldimethylsilyl ester. On the other hand, the nitrogen atom of the indole can or cannot be protected. When this nitrogen atom is protected, a benzyl protective group is preferred. An amide protective group is not preferred because of reducing reactivity. Also, the Michael reaction can proceed by the heating of the reaction system and can be carried out using a catalyst such as Lewis acid. After the obtainment of the skeleton of the compound represented by the formula (I), the protective group can be removed, if necessary, to synthesize the compound represented by the formula (I). Then, the carboxylic acid moiety can also be appropriately esterified, amidated, or converted to a pharmaceutically acceptable salt according to the purpose. Specifically, compound #4 mentioned later in Examples can be synthesized from fluorobenzene, maleic anhydride, and indole as shown in the following scheme:

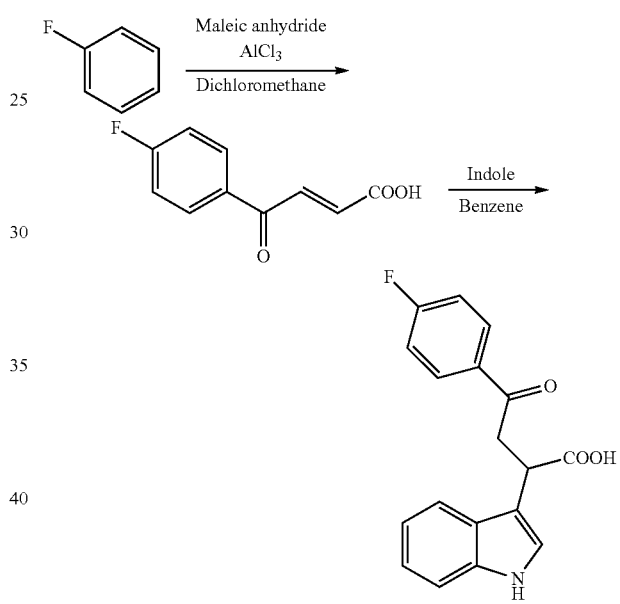

In an alternative aspect, examples of the method for synthesizing the compound represented by the formula (I) can include a synthesis method using an alcohol and a protected form of indoleacetic acid as starting materials. The hydroxy group of the alcohol can be converted to iodine or bromine either directly or through two-step reaction. Examples of the method involving direct conversion can include, but are not limited to, a method of substituting the alcohol by iodine (I.) by the action of triphenylphosphine, imidazole, and iodine ($I_2$), and a method of substituting the alcohol by bromine by the action of triphenylphosphine and carbon tetrabromide. Examples of the synthesis method through a plurality of steps can include a method of derivatizing the alcohol into a sulfonic acid ester such as methanesulfonate, trifluoromethanesulfonate, or toluenesulfonate, followed by reaction with an iodide salt of an alkali metal or a bromide salt of an alkali metal. The halogen form thus obtained can be nucleophilically reacted with enolate at the α-position formed from the protected form of indoleacetic acid to obtain the basic skeleton of the compound represented by the formula (I). Examples of the protective group for the indoleacetic acid include a method of derivatizing the indoleacetic acid into methyl ester, tert-butyl ester, 2,2,2-trichloroethyl ester, or tert-butyldimethylsilyl ester for the protection of the carboxyl group. On the other hand, the amine site of the indoleacetic acid is preferably protected as amide carbonate. Examples of the protective group can include methoxycarbonyl, ethoxycarbonyl, tert-butoxycarbonyl, and benzyloxycarbonyl. The protected form of the indoleacetic acid thus obtained is derivatized into enolate by the action of a base. The formed enolate and the halogen form can be subjected to nucleophilic reaction to obtain the basic skeleton of the compound represented by the formula (I). Examples of the base that can be used in this nucleophilic reaction can include: a carbonate of an alkali metal such as lithium carbonate, sodium carbonate, potassium carbonate, and cesium carbonate; an alkyllithium such as methyllithium, n-butyllithium, sec-butyllithium, and tert-butyllithium; and an alkali metal amide such as lithium diisopropylamide, lithium hexamethyldisilazane, sodium hexamethyldisilazane, and potassium hexamethyldisilazane. The solvent that can be used differs depending on the base used and is preferably an aprotic polar solvent such as N,N-dimethylformamide (DMF) or tetrahydrofuran (THF). The addition of hexamethylphosphoric triamide or the like is effective for promoting the reaction. The protective group can be removed from the protected form thus obtained to obtain the compound of interest. Then, the carboxylic acid moiety can be appropriately esterified, amidated, or converted to a pharmaceutically acceptable salt thereof. Specifically, compound #21 mentioned later in Examples can be synthesized with 4,4,5,5,5-pentafluoropentanol and 1-methoxycarbonyl-3-indoleacetic acid methyl ester as starting materials as shown in the following scheme:

The aforementioned method for synthesizing the compound represented by the formula (I) can also be used for synthesizing the compound represented by the formula (II). Specifically, the compound represented by the formula (II) can be synthesized in the same way as the aforementioned method for synthesizing the compound represented by the formula (I) except that a linear amino alcohol with an amino group protected with tert-butoxycarbonyl or a linear amino alcohol having oxygen in the chain and a protected form of indoleacetic acid in which the α-position is substituted by a methyl group are used as starting materials, instead of the alcohol and the protected form of indoleacetic acid used as starting materials. The linear amino alcohol and the linear amino alcohol having oxygen in the chain can each be converted to tert-butoxycarbonylamide by a standard method. Usually, di-tert-butyl carbonate is used. Those skilled in the art readily understand that the protected form of indoleacetic acid in which the α-position is substituted by a methyl group is an intermediate obtained using methyl iodide as the halogen form in the method for synthesizing the compound represented by the formula (I). The starting materials thus prepared can be used in the same way as the method for synthesizing the compound represented by the formula (I) to synthesize the compound represented by the formula (II). Specifically, compound #15 mentioned later in Examples can be synthesized as 4-aminobutanol and 1-methoxycarbonyl-3-indoleacetic acid methyl ester as starting materials as shown in the following scheme:

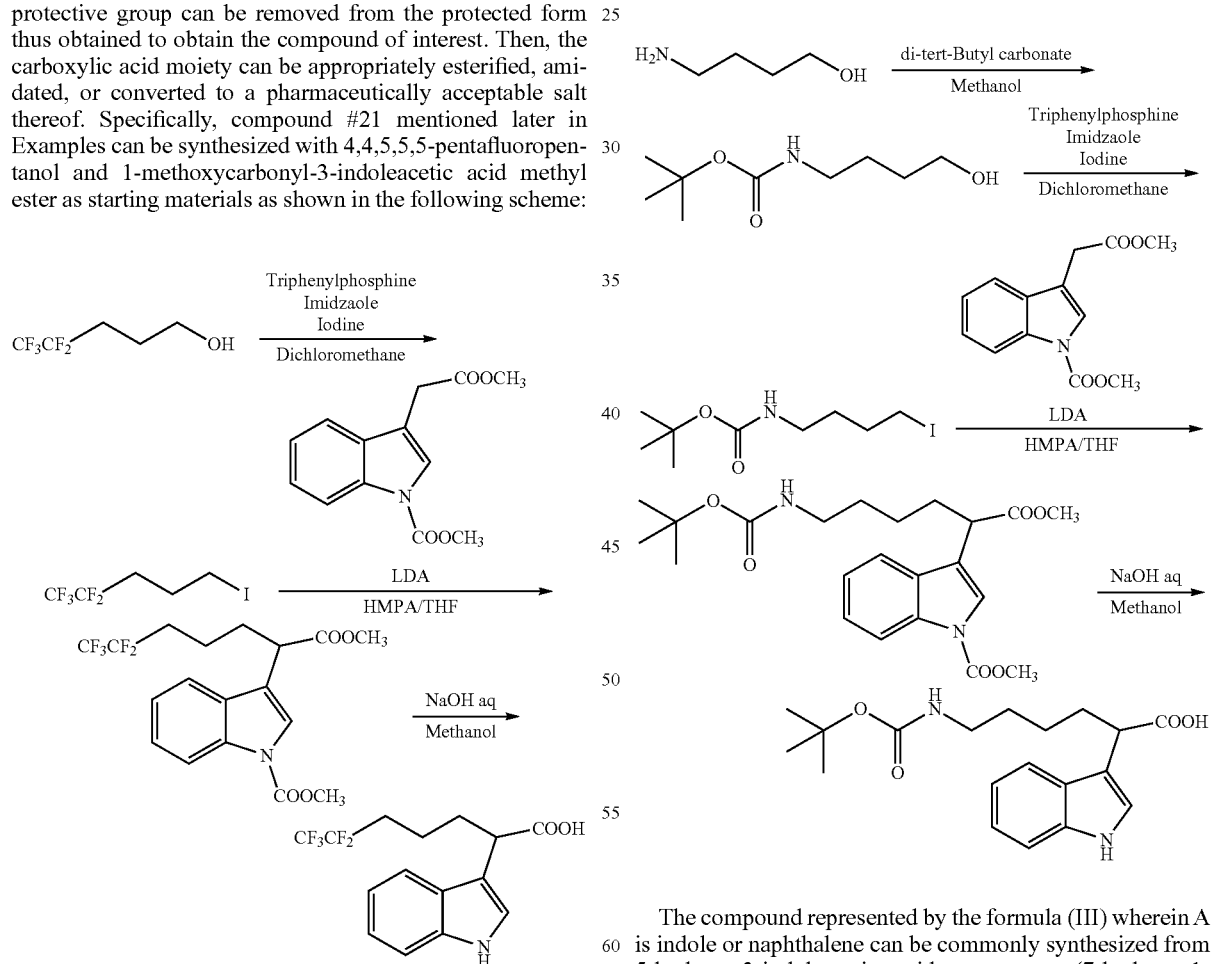

The compound represented by the formula (III) wherein A is indole or naphthalene can be commonly synthesized from 5-hydroxy-3-indoleacetic acid ester or α-(7-hydroxy-1-naphthalenyl)-acetic acid ester as a starting material. The 5-hydroxy-3-indoleacetic acid ester and the α-(7-hydroxy-1-naphthalenyl)-acetic acid ester can be obtained by the esterification of corresponding carboxylic acids. The 5-hydroxy-3-indoleacetic acid and the α-(7-hydroxy-1-naphthalenyl)-acetic acid have three active protons and two active protons, respectively, which present problems associated with reaction selectivity. For this reason, the alcohol moieties of these compounds are protected, and the protective group can be removed after the esterification to obtain the starting material. Alternatively, α-(7-hydroxy-1-naphthalenyl)-acetic acid ethyl ester can also be synthesized according to a method described in E. Tsuda et. al., "Alkoxy-auxins are selective inhibitors of auxin transport mediated by PIN, ABCB, and AUX1 transporters" Journal of Biological Chemistry, 286 (3), 2354-2364; 2011. In addition, a method for synthesizing the 5-hydroxy-3-indoleacetic acid ester can involve synthesizing an ester with an alcohol used as a solvent with favorable selectivity through a reaction under acidic conditions in a dried alcohol. Examples of conditions for the esterification reaction can include commercially available hydrochloric acid/methanol and a method of blowing dried hydrochloric acid into a dehydrated alcohol. A method of adding dropwise acid chloride to a preliminarily dried alcohol to generate an acid in the system is preferred. Then, the carboxylic acid moiety can be appropriately esterified, amidated, or converted to a pharmaceutically acceptable salt thereof. The starting material thus prepared can be reacted with alkyl iodide or alkyl bromide to construct the basic skeleton of the compound represented by the formula (III). Examples of the base used in this reaction of the 5-hydroxy-3-indoleacetic acid ester or the 7-hydroxy-1-naphthalenylacetic acid ester with alkyl iodide or alkyl bromide include sodium hydride and a carbonate of an alkali metal such as lithium carbonate, sodium carbonate, potassium carbonate, and cesium carbonate. The reaction solvent is preferably an aprotic polar solvent such as DMF or THF. After the obtainment of the skeleton of the compound represented by the formula (III), the protective group can be removed, if necessary, to synthesize the compound represented by the formula (III). Then, the carboxylic acid moiety can also be appropriately esterified, amidated, or converted to a pharmaceutically acceptable salt according to the purpose. Specifically, compound #34 mentioned later in Examples can be synthesized with 1-iodobutane and α-(7-hydroxy-1-naphthalenyl)-acetic acid ethyl ester as starting materials as shown in the following scheme:

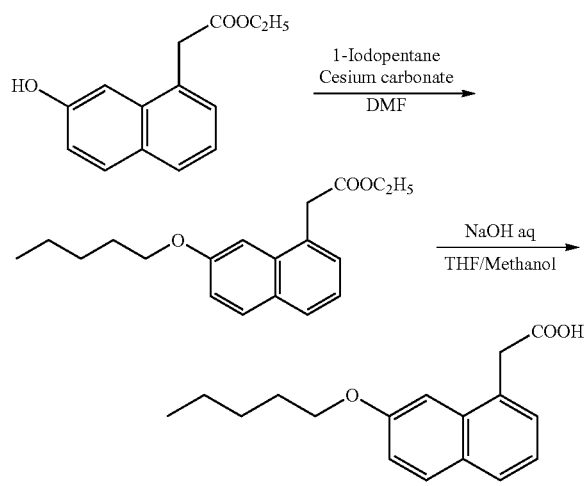

Similarly, compound #35 mentioned later in Examples can be synthesized by using 3,5-dimethoxybenzyl bromide and 7-hydroxy-3-indoleacetic acid as starting materials.

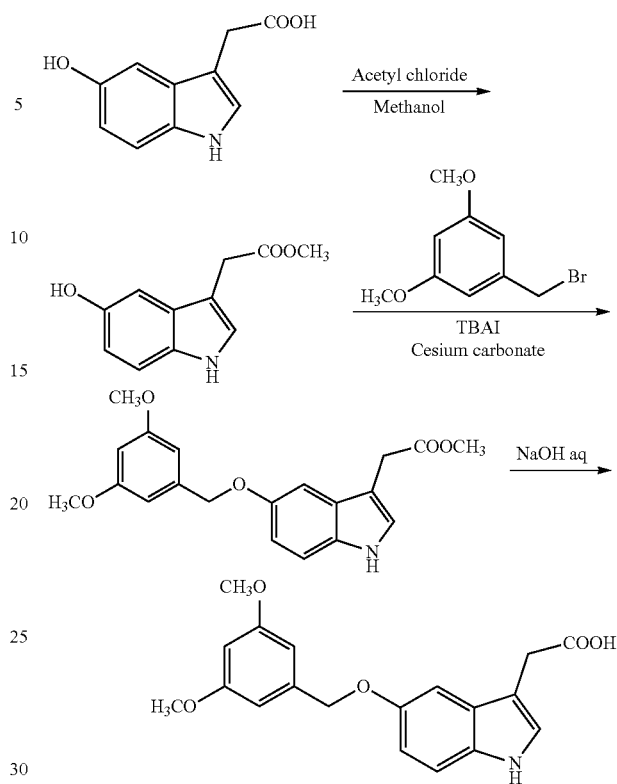

Of the compounds included in the compound group 1 of the present invention, specific examples of a compound having the effect of enhancing the expression (production) of erythropoietin can include 21 types of compounds (compounds mentioned later in Examples [#2, 4, 5, 13 to 15, to 25, and 33 to 38]). Among them, examples of a compound having the effect of canceling the suppression of erythropoietin expression by an inflammatory cytokine can include 11 types of compounds (#21 to 25 and 33 to 38). Examples of a compound having the effect of promoting erythropoietin expression can include 11 types of compounds (#2, 4, 5, 13 to 15, and 17 to 21]). Among them, preferred examples thereof can include 3 types of compounds (#4, 21, and 35).

The compound group 1 of the present invention as the therapeutic agent for a mitochondrial disease of the present invention is preferably 5 types of compounds specifically shown in Examples of the present specification to be effective (compounds [#2, 4, 5, 21, and 35]).

The ATP production-promoting agent of an alternative embodiment is not particularly limited as long as the agent contains one or more compounds selected from compound group 2 of the present invention as active ingredients. Hereinafter, each compound included in the compound group 2 of the present invention will be described in detail.

$R^8$ in the formula (i) is a benzoylmethyl group whose benzene ring is unsubstituted or substituted by an alkyl group having 1 to 7 carbon atoms, an alkoxyl group having 1 to 7 carbon atoms, fluorine, and/or chlorine. The benzene ring of this benzoylmethyl group is optionally substituted. Examples of the substituted benzoylmethyl group can include a benzoylmethyl group having 1 to 5 alkyl groups having 1 to 7 carbon atoms, 1 to 5 alkoxyl groups having 1 to 7 carbon atoms, 1 to 5 fluorine atoms, or 1 to 5 chlorine atoms on the benzene ring or having 1 to 5 substituents in total of an alkyl group having 1 to 4 carbon atoms, an alkoxyl group having 1 to 4 carbon atoms, a fluorine atom, and a chlorine atom on the benzene ring. In this context, examples of the alkyl group having 1 to 7 carbon atoms can include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4,4-dimethylpentyl group, and a 1-propylbutyl group.

Examples of the alkoxyl group having 1 to 7 carbon atoms can include a methoxy group, an ethoxy group, a propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, and a 1-propylbutoxy group.

In an alternative aspect of the present invention, $R^8$ in the formula (i) is an unsubstituted or fluorine-substituted linear or branched alkyl group having 4 to 6 carbon atoms. Examples of the unsubstituted or fluorine-substituted linear or branched alkyl group having 4 to 6 carbon atoms can include a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, and fluorinated forms thereof. The unsubstituted or fluorine-substituted linear or branched alkyl group having 4 to 6 carbon atoms is preferably a 1-ethylbutyl group, a 2-ethylbutyl group, a 1-methylpentyl group, a 2-methylpentyl group, a 3-methylpentyl group, a 4-methylpentyl group, a 5-methylpentyl group, a 3,3,4,4,4-pentafluorobutyl group, a 4,4,5,5,5-pentafluoropentyl group, or a 5,5,6,6,6-pentafluorohexyl group, more preferably a 2-ethylbutyl group, a 2-methylpentyl group, a 3-methylpentyl group, or a 4,4,5,5,5-pentafluoropentyl group.

In an alternative aspect of the present invention, $R^8$ in the formula (i) is 4-N-acetylpiperidinyl group-, phenyl group-, or cyclopentyl group-substituted methylene or ethylene. The phenyl group is optionally further substituted by one or more phenyl groups. The 4-N-acetylpiperidinyl group-, phenyl group-, or cyclopentyl group-substituted methylene or ethylene is a 4-N-acetylpiperidinylmethyl group, a 2-(4-N-acetylpiperidinyl)ethyl group, a benzyl group, a 2-phenethyl group, a cyclopentylmethyl group, or a 2-cyclopentylethyl group. Examples of the benzyl group or the 2-phenethyl group substituted by one or more phenyl groups can include a 3-phenylbenzyl group, a 4-phenylbenzyl group, a 3,5-diphenylbenzyl group, a 2-(1,1'-biphenyl-3-yl)-ethyl group, a 2-(1,1'-biphenyl-4-yl)-ethyl group, and a 2-(3,5-diphenylphenyl)-ethyl group. Preferred examples of $R^8$ in the formula (i) can include a 4-N-acetylpiperidinylmethyl group, a 2-(4-N-acetylpiperidinyl)ethyl group, a 2-phenylethyl group, a 2-(1,1'-biphenyl-3-yl)-ethyl group, a cyclopentylmethyl group, and a 2-cyclopentylethyl group.

$R^9$ in the formula (i) is a group that optionally substitutes positions 4, 5, 6, and/or 7 of the indole skeleton. One or more $R^2$ can be added to each substitution position. Examples of $R^2$ can include an alkyl group having 1 to 4 carbon atoms, an alkoxyl group having 1 to 7 carbon atoms, fluorine, and chlorine. Examples of the alkyl group having 1 to 4 carbon atoms can include a methyl group, an ethyl group, a propyl group, an isopropyl group, a n-butyl group, an isobutyl group, a sec-butyl group, and a tert-butyl group. Examples of the alkoxyl group having 1 to 7 carbon atoms can include a methoxy group, an ethoxy group, a propoxy group, an isopropoxy group, a n-butoxy group, an isobutoxy group, a sec-butoxy group, a tert-butoxy group, a n-pentoxy group, a 1-methylbutoxy group, a 2-methylbutoxy group, a 3-methylbutoxy group, a 1-ethylpropoxy group, a 1,1-dimethylpropoxy group, a 1,2-dimethylpropoxy group, a 2,2-dimethylpropoxyl group, a n-hexyloxy group, a 1-methylpentyloxy group, a 2-methylpentyloxy group, a 3-methylpentyloxy group, a 4-methylpentyloxy group, a 1,1-dimethylbutoxy group, a 1,2-dimethylbutoxy group, a 1,3-dimethylbutoxy group, a 2,2-dimethylbutoxy group, a 2,3-dimethylbutoxy group, a 3,3-dimethylbutoxy group, a 1,1,2-trimethylpropoxy group, a 1-ethylbutoxy group, a 2-ethylbutoxy group, a 1-ethyl-1-methylpropoxy group, a 1-ethyl-2-methylpropoxy group, a n-heptyloxy group, a 1-methylhexyloxy group, a 2-methylhexyloxy group, a 3-methylhexyloxy group, a 4-methylhexyloxy group, a 5-methylhexyloxy group, a 1-ethylpentyloxy group, a 2-ethylpentyloxy group, a 3-ethylpentyloxy group, a 4,4-dimethylpentyloxy group, and a 1-propylbutoxy group. $R^9$ is preferably hydrogen, an ethoxy group, fluorine, or chlorine.

$R^{10}$ in the formula (i) is hydrogen or a linear or branched alkyl group having 1 to 3 carbon atoms. Specific examples of such $R^{10}$ can include hydrogen as well as a methyl group, an ethyl group, a n-propyl group, and an isopropyl group. Among them, preferred examples thereof can include hydrogen and a propyl group.

$R^{12}$ and $R^{13}$ in the formula (i) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^{12}$ and $R^{13}$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (i) wherein $R^8$ is a 2,4-dimethylbenzoylmethyl group, $R^9$ is chlorine that substitutes position 5 of indole, $R^{10}$ is a n-propyl group, and $R^{11}$ is OH represents compound #6 mentioned later in Examples. The compound represented by the formula (i) wherein $R^8$ is a 4,4,5,5,5-pentafluoropentyl group, $R^9$ is hydrogen, $R^{10}$ is hydrogen, and $R^{11}$ is OH represents compound #21 mentioned later in Examples. The compound represented by the formula (i) wherein $R^8$ is a 2-(4-N-acetylpiperidinyl)ethyl group, $R^9$ is hydrogen, $R^{10}$ is hydrogen, and $R^{11}$ is OH represents compound #8 mentioned later in Examples. In addition to these compounds, specific examples of the compound represented by the formula (i) can include compounds #1, 2, 4, 5 to 7, and 20 mentioned later in Examples, compounds #17 to 19 mentioned later in Examples, compounds #22 and 23 mentioned later in Examples, compounds #24 and 25 mentioned later in Examples, and compound #9 mentioned later in Examples.

X in the formula (ii) is a linear alkylene group having 4 to 6 carbon atoms, i.e., butylene —$(CH_2)_4$—, pentylene-$(CH_2)_5$—, or hexylene-$(CH_2)_6$—, or an ether group having 4 carbon atoms. Examples of the ether group having 4 carbon atoms can include a methylene-O-propylene group, an ethylene-O-ethylene group, and a propylene-O-methylene group. X is preferably butylene —$(CH_2)_4$—, hexylene —$(CH_2)_6$—, or an ethylene-O-ethylene group, more preferably an ethylene-O-ethylene group.

$R^{12}$ and $R^{13}$ in the formula (ii) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^{12}$ and $R^{13}$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (ii) wherein X is an ethylene-O-ethylene group, $R^{14}$ is hydrogen, $R^{15}$ is a tert-butoxy group, and $R^{11}$ is OH represents compound #14 mentioned later in Examples. In addition to the compound #14, specific examples of the compound represented by the formula (ii) can include compounds #10 and 11 mentioned later in Examples, compound #13 mentioned later in Examples, and compound #15 mentioned later in Examples.

$R^{16}$ in the formula (iii) is a linear or branched alkyl group having 1 to 7 carbon atoms or a benzyl group. Examples of the linear or branched alkyl group having 1 to 7 carbon atoms can include a methyl group, an ethyl group, a propyl group, an isopropyl group, a n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1-ethylbutyl group, a 2-ethylbutyl group, a 1-ethyl-1-methylpropyl group, a 1-ethyl-2-methylpropyl group, a n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4,4-dimethylpentyl group, and a 1-propylbutyl group. The benzene ring of the benzyl group is optionally substituted by one or more alkyl groups having 1 to 3 carbon atoms or alkoxyl groups having 1 to 3 carbon atoms. Examples of the alkyl group having 1 to 3 carbon atoms can include a methyl group, an ethyl group, a n-propyl group, and an isopropyl group. Examples of the alkoxy group having 1 to 3 carbon atoms can include a methoxy group, an ethoxy group, a n-propoxy group, and an isopropoxy group. Of them, a methyl group, an ethyl group, a propyl group, a n-butyl group, a n-pentyl group, and a 3,5-dimethoxybenzyl group are preferred. A 3,5-dimethoxybenzyl group is more preferred.

$R^{12}$ and $R^{13}$ in the formula (iii) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^{12}$ and $R^{13}$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (iii) wherein A is indole, $R^{16}$ is a methyl group, and $R^{11}$ is OH represents compound #36 mentioned later in Examples. In addition to the compound #36, specific examples of the compound represented by the formula (iii) can include compounds #37 to 39 mentioned later in Examples and compounds #34 and #35 mentioned later in Examples.

$R^{17}$ in the formula (iv) is a linear alkyl group having 1 to 7 carbon atoms. Specific examples of the linear alkyl group having 1 to 7 carbon atoms can include a methyl group, an ethyl group, a propyl group, a n-butyl group, a n-pentyl group, a n-hexyl group, and a n-heptyl group.

$R^{12}$ and $R^{13}$ in the formula (iv) or (v) are the same or different and each represents a substituted or unsubstituted alkyl group having 1 to 4 carbon atoms. Examples of the substituted or unsubstituted alkyl group having 1 to 4 carbon atoms can include a methyl group, an ethyl group, a propyl group, an isopropyl group, a n-butyl group, an isobutyl group, a sec-butyl group, a tert-butyl group, pyrrolidine formed by $R^3$ and $R^4$ together with nitrogen, and forms thereof substituted by a methoxy group, a phenyl group, fluorine, and chlorine. The substituted or unsubstituted alkyl group having 1 to 4 carbon atoms is preferably a methyl group, a monochloromethyl group, an ethyl group, a 2-methoxyethyl group, a 2,2,2-trichloroethyl group, a 1-phenylethyl group, a 2-phenylethyl group, a methoxyethyl group, an isopropyl group, a hexafluoroisopropyl group, or pyrrolidine, more preferably a methyl group or an ethyl group.

The compound represented by the formula (iv) wherein $R^{17}$ is a butyl group, and $R^{11}$ is OH represents compound #29 mentioned later in Examples. In addition to the compound #29, specific examples of the compound represented by the formula (iv) can include compounds #26 to 28, 30, and 31 mentioned later in Examples. The compound represented by the formula (v) wherein $R^{11}$ is OH represents compound #12 mentioned later in Examples.

When a compound selected from compound group 2 of the present invention has an asymmetric carbon atom and an axial chirality-related asymmetric point, this compound includes all possible optical isomers. These optical isomers can be used at an arbitrary ratio. For example, a certain optically active compound can be used as an enantiomer, a racemate, or an enantiomer mixture at an arbitrary ratio. A compound, if containing a plurality of asymmetric points, can be used as a diastereomer mixture at an arbitrary ratio.

The pharmaceutically acceptable salts of compound group 2 of the present invention include, for example, metal salts formed from aluminum, calcium, lithium, magnesium, potassium, sodium, and zinc, and organic salts formed from N,N'-dibenzylethylenediamine, chloroprocaine, choline, diethanolamine, ethylenediamine, N-methylglucamine, lysine, procaine, and the like.

Exemplary methods for synthesizing each compound selected from compound group 2 of the present invention will be given below. However, the synthesis methods of the present invention are not limited to these methods, and generally known synthesis methods can be used. Compounds shown below can be obtained from Sigma-Aldrich Corp., Tokyo Chemical Industry Co., Ltd., Wako Pure Chemical Industries, Ltd., Kanto Chemical Co., Inc., etc. As for reaction solvents and reaction temperatures, a reaction is carried out using a solvent and a temperature usually used for the reaction, unless otherwise specified.

Each reaction is usually carried out in an argon or nitrogen atmosphere. Each protective group can be used with reference to Green & Wuts, "PROTECTIVE GROUPS in ORGANIC SYNTHESIS" 3rd ed. John Wiley & Sons, Inc.

The compound represented by the formula (i) can be synthesized from substituted or unsubstituted benzene and substituted or unsubstituted indole as starting materials. First, substituted or unsubstituted benzene and maleic anhydride are used in Friedel-Crafts reaction to synthesize 4-aryl-4-oxo-2-butenoic acid. This Friedel-Crafts reaction is carried out by the action of a catalyst such as Lewis acid, phosphoric acid, or polyphosphoric acid. Aluminum chloride is preferably used as the catalyst. The reaction solvent is preferably a chlorine solvent. Alternatively, the starting material substituted or unsubstituted benzene can also be used as a solvent. The 4-aryl-4-oxo-2-butenoic acid thus obtained and substituted or unsubstituted indole are subjected to Michael reaction to obtain a compound in which the α-position of indoleacetic acid is substituted by a substituted or unsubstituted benzoyloxy group. In this way, the basic skeleton of the compound represented by the formula (i) can be constructed. In this Michael reaction, the carboxyl group of the 4-aryl-4-oxo-2-butenoic acid can or cannot be protected and, usually, does not have to be protected. When this carboxyl group is protected, examples of the protective group used can include methyl ester, tert-butyl ester, 2,2,2-trichloroethyl ester, and tert-butyldimethylsilyl ester. On the other hand, the nitrogen atom of the indole can or cannot be protected. When the compound represented by the formula (i) has a linear or branched alkyl group having 1 to 3 carbon atoms on the nitrogen atom of the indole, the alkyl group is preferably introduced thereto prior to the Michael reaction. The introduction of the alkyl group to the indole is carried out by the action of a base on a corresponding alkyl halide in an aprotic polar solvent such as DMF or THF. The addition of hexamethylenephosphoric triamide or the like can also promote the reaction. In this context, examples of the base that can be used can include: an alkali metal hydride such as sodium hydride; and a metal carbonate such as lithium carbonate, sodium carbonate, potassium carbonate, and cesium carbonate. The Michael reaction can proceed by the heating of the reaction system and can be carried out using a catalyst such as Lewis acid. After the obtainment of the skeleton of the compound represented by the formula (i), the protective group can be removed, if necessary, to synthesize the compound represented by the formula (i). Then, the carboxylic acid moiety can also be appropriately esterified, amidated, or converted to a pharmaceutically acceptable salt according to the purpose. Specifically, compound #6 mentioned later in Examples can be synthesized from m-xylene, maleic anhydride, and N-propylindole as shown in the following scheme:

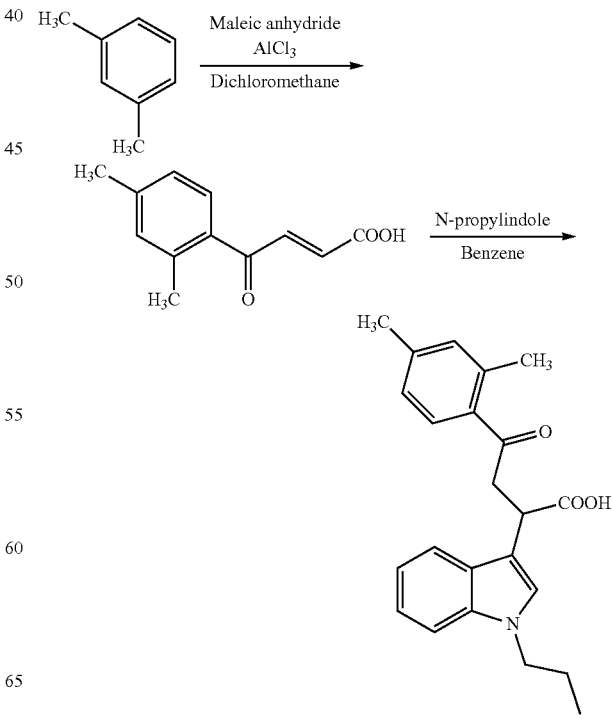

In an alternative aspect, examples of the method for synthesizing the compound represented by the formula (i) can include a synthesis method using an alcohol and a protected form of indoleacetic acid as starting materials. The hydroxy group of the alcohol can be converted to iodine or bromine either directly or through two-step reaction. Examples of the method involving direct conversion can include, but are not limited to, a method of substituting the alcohol by iodine (I.) by the action of triphenylphosphine, imidazole, and iodine ($I_2$), and a method of substituting the alcohol by bromine by the action of triphenylphosphine and carbon tetrabromide. Examples of the synthesis method through a plurality of steps can include a method of derivatizing the alcohol into a sulfonic acid ester such as methanesulfonate, trifluoromethanesulfonate, or toluenesulfonate, followed by reaction with an iodide salt of an alkali metal or a bromide salt of an alkali metal. The halogen form thus obtained can be nucleophilically reacted with enolate at the α-position formed from the protected form of indoleacetic acid to obtain the basic skeleton of the compound represented by the formula (i). Examples of the protective group for the indoleacetic acid can include a method of derivatizing the indoleacetic acid into methyl ester, tert-butyl ester, 2,2,2-trichloroethyl ester, or tert-butyldimethylsilyl ester for the protection of the carboxyl group. On the other hand, the amine site of the indoleacetic acid is preferably protected as amide carbonate. Examples of the protective group can include methoxycarbonyl, ethoxycarbonyl, tert-butoxycarbonyl, and benzyloxycarbonyl. The protected form of the indoleacetic acid thus obtained is derivatized into enolate by the action of a base. The formed enolate and the halogen form can be subjected to nucleophilic reaction to obtain the basic skeleton of the compound represented by the formula (i). Examples of the base that can be used in this nucleophilic reaction can include: a carbonate of an alkali metal such as lithium carbonate, sodium carbonate, potassium carbonate, and cesium carbonate; an alkyllithium such as methyllithium, n-butyllithium, sec-butyllithium, and tert-butyllithium; and an alkali metal amide such as lithium diisopropylamide, lithium hexamethyldisilazane, sodium hexamethyldisilazane, and potassium hexamethyldisilazane. The solvent that can be used differs depending on the base used and is preferably an aprotic polar solvent such as N,N-dimethylformamide (DMF) or tetrahydrofuran (THF). The addition of hexamethylphosphoric triamide or the like is effective for promoting the reaction. The protective group can be removed from the protected form thus obtained to obtain the compound of interest. Then, the carboxylic acid moiety can be appropriately esterified, amidated, or converted to a pharmaceutically acceptable salt thereof. Specifically, compound #8 mentioned later in Examples can be synthesized with 2-(4-piperidinyl)ethanol and 1-methoxycarbonyl-3-indoleacetic acid methyl ester as starting materials as shown in the following scheme:

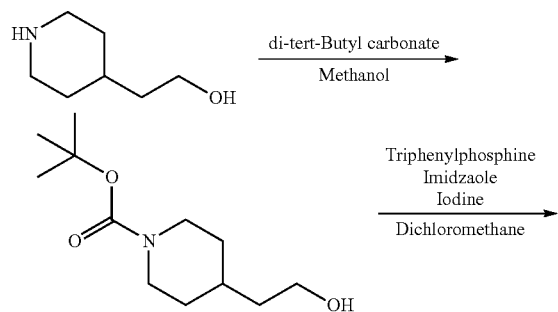

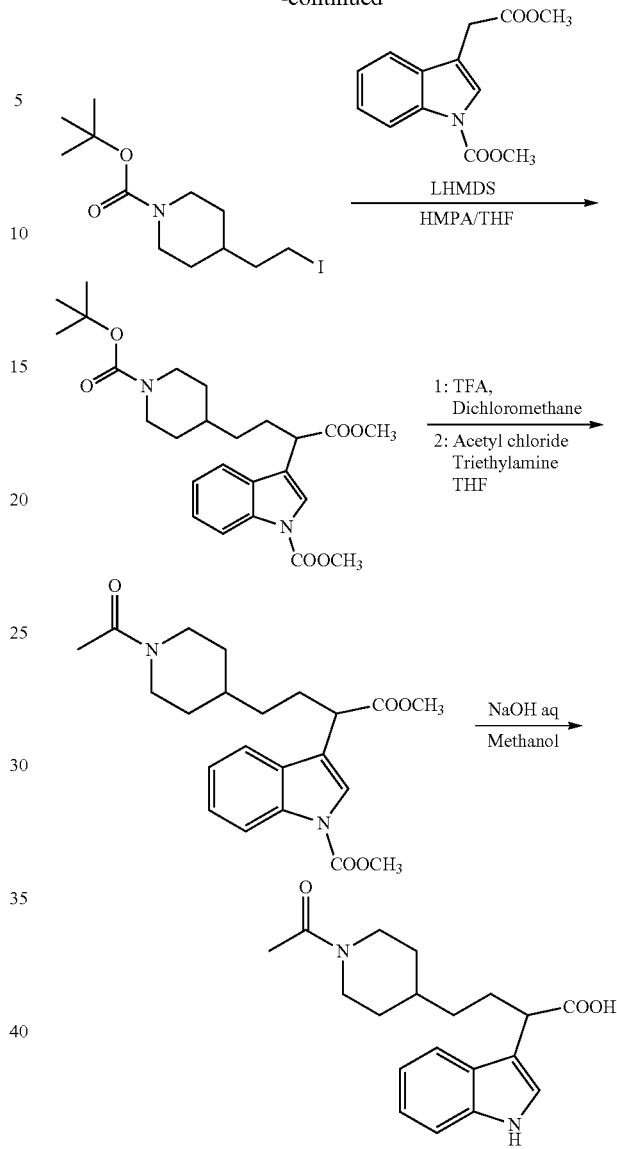

The aforementioned method for synthesizing the compound represented by the formula (i) can also be used in the synthesis of the compound represented by the formula (ii). Specifically, the compound represented by the formula (ii) can be synthesized in the same way as the aforementioned method for synthesizing the compound represented by the formula (i) except that a linear amino alcohol with an amino group protected with tert-butoxycarbonyl or a linear amino alcohol having oxygen in the chain and a protected form of indoleacetic acid in which the α-position is substituted by a methyl group are used as starting materials, instead of the alcohol and the protected form of indoleacetic acid used as starting materials. The linear amino alcohol and the linear amino alcohol having oxygen in the chain can each be converted to tert-butoxycarbonylamide by a standard method. Usually, di-tert-butyl carbonate is used. Those skilled in the art readily understand that the protected form of indoleacetic acid in which the α-position is substituted by a methyl group is an intermediate obtained using methyl iodide as the halogen form in the method for synthesizing the compound represented by the formula (i). The starting materials thus prepared can be used in the same way as the method for synthesizing the compound represented by the formula (i) to achieve the synthesis of the compound represented by the formula (ii). Specifically, compound #14 mentioned later in Examples can be synthesized from 2-(2-aminoethoxy)-ethanol and 1-methoxycarbonyl-3-indoleacetic acid methyl ester as shown in the following scheme:

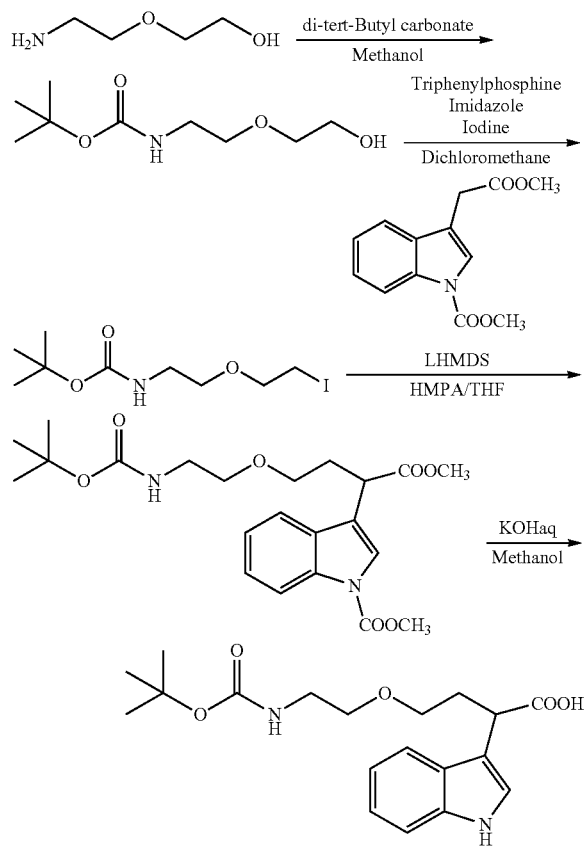

The compound represented by the formula (iii) wherein A is indole or naphthalene can be commonly synthesized from 5-hydroxy-3-indoleacetic acid ester or α-(7-hydroxy-1-naphthalenyl)-acetic acid ester as a starting material. The 5-hydroxy-3-indoleacetic acid ester and the α-(7-hydroxy-1-naphthalenyl)-acetic acid ester can be obtained by the esterification of corresponding carboxylic acids. The 5-hydroxy-3-indoleacetic acid and the α-(7-hydroxy-1-naphthalenyl)-acetic acid have three active protons and two active protons, respectively, which present problems associated with reaction selectivity. For this reason, the alcohol moieties of these compounds are protected, and the protective group can be removed after the esterification to obtain the starting material. Alternatively, α-(7-hydroxy-1-naphthalenyl)-acetic acid ethyl ester can also be synthesized according to a method described in E. Tsuda et. al., "Alkoxy-auxins are selective inhibitors of auxin transport mediated by PIN, ABCB, and AUX1 transporters" Journal of Biological Chemistry, 286 (3), 2354-2364; 2011. In addition, a method for synthesizing the 5-hydroxy-3-indoleacetic acid ester can involve synthesizing an ester with an alcohol used as a solvent with favorable selectivity through a reaction under acidic conditions in a dried alcohol. Examples of conditions for the esterification reaction can include commercially available hydrochloric acid/methanol and a method of blowing dried hydrochloric acid into a dehydrated alcohol. A method of adding dropwise acid chloride to a preliminarily dried alcohol to generate an acid in the system is preferred. Then, the carboxylic acid moiety can be appropriately esterified, amidated, or converted to a pharmaceutically acceptable salt thereof. The starting material thus prepared can be reacted with alkyl iodide or alkyl bromide to construct the basic skeleton of the compound represented by the formula (iii). Examples of the base used in this reaction of the 5-hydroxy-3-indoleacetic acid ester or the 7-hydroxy-1-naphthalenylacetic acid ester with alkyl iodide or alkyl bromide can include sodium hydride and a carbonate of an alkali metal such as lithium carbonate, sodium carbonate, potassium carbonate, and cesium carbonate. The reaction solvent is preferably an aprotic polar solvent such as DMF or THF. After the obtainment of the skeleton of the compound represented by the formula (iii), the protective group can be removed, if necessary, to synthesize the compound represented by the formula (iii). Then, the carboxylic acid moiety can also be appropriately esterified, amidated, or converted to a pharmaceutically acceptable salt according to the purpose. Specifically, compound #36 mentioned later in Examples can be synthesized from iodomethane and -hydroxy-3-indoleacetic acid methyl ester as shown in the following scheme:

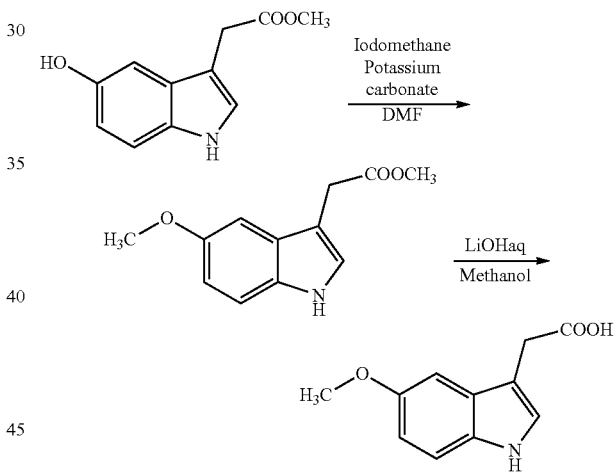

Similarly, compound #34 mentioned later in Examples can be synthesized by using 1-iodobutane and α-(7-hydroxy-1-naphthalenyl)-acetic acid ethyl ester as starting materials.

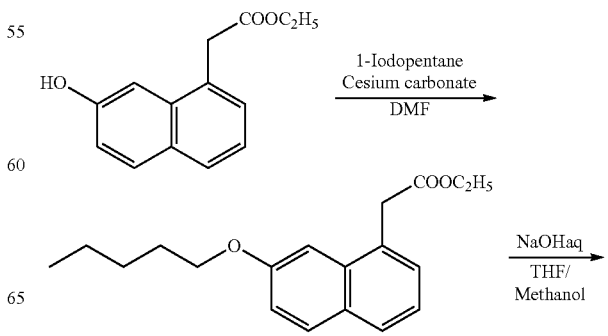

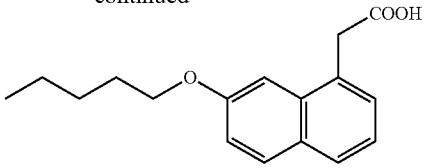

The compound represented by the formula (iv) can be synthesized from indoleacetic acid whose the carboxyl group is protected and an alkyl halide as starting materials. The indoleacetic acid can be protected by derivatization into methyl ester, ethyl ester, tert-butyl ester, 2,2,2-trichloroethyl ester, tert-butyldimethylsilyl ester, or the like. The alkyl halide can be introduced to the protected form of the indoleacetic acid by the action of a base on the alkyl halide in an aprotic polar solvent such as DMF or THF. The addition of hexamethylenephosphoric triamide or the like can also promote the reaction. In this context, examples of the base that can be used can include: an alkali metal hydride such as sodium hydride; and a metal carbonate such as lithium carbonate, sodium carbonate, potassium carbonate, and cesium carbonate. After the introduction of the alkyl group, the protective group can be appropriately removed to synthesize the compound represented by the formula (iv). Then, the carboxylic acid moiety can also be appropriately esterified, amidated, or converted to a pharmaceutically acceptable salt according to the purpose. Specifically, compound #29 mentioned later in Examples can be synthesized from butyl iodide and 3-indoleacetic acid methyl ester as shown in the following scheme:

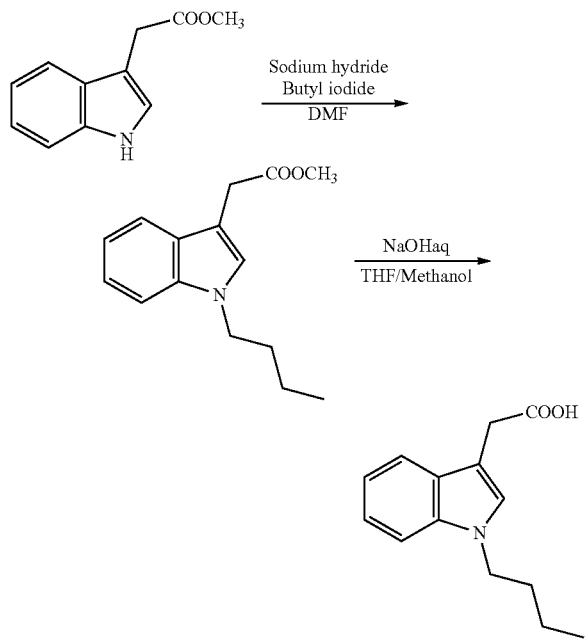

The compound represented by the formula (v) can be synthesized from N-tert-butoxycarbonyl-6-aminohexanol and α-(1-naphthalenyl)-acetic acid ester as starting materials. The N-tert-butoxycarbonyl-6-aminohexanol can be synthesized through the reaction of 6-aminohexanol with di-tert-butyl carbonate in the presence of a base. A hydroxy group of the obtained N-tert-butoxycarbonyl-6-aminohexanol can be converted to iodine or bromine by the method described in the method for synthesizing the compound represented by the formula (I) or the formula (i). This 1-halogenated N-tert-butoxycarbonyl-6-aminohexane can be reacted with enolate formed from α-(1-naphthalenyl)-acetic acid ester in the same way as the method described in the method for synthesizing the compound represented by the formula (I) or the formula (i) to obtain the basic skeleton of the compound represented by the formula (v). The ester site of the obtained compound can be hydrolyzed to synthesize the compound represented by the formula (i). For the method for hydrolyzing the ester, a metal hydroxide such as lithium hydroxide, sodium hydroxide, or potassium hydroxide, or a metal alkoxide such as sodium methoxide or potassium tert-butoxide can be used in a solvent containing an alcohol. If necessary, the reaction rate can also be improved by the addition of an aqueous hydrogen peroxide solution to the reaction system. Then, the carboxylic acid moiety can also be appropriately esterified, amidated, or converted to a pharmaceutically acceptable salt according to the purpose. Specifically, compound #12 can be synthesized from 6-aminohexanol and α-(7-hydroxy-1-naphthalenyl)-acetic acid ethyl ester as shown in the following scheme:

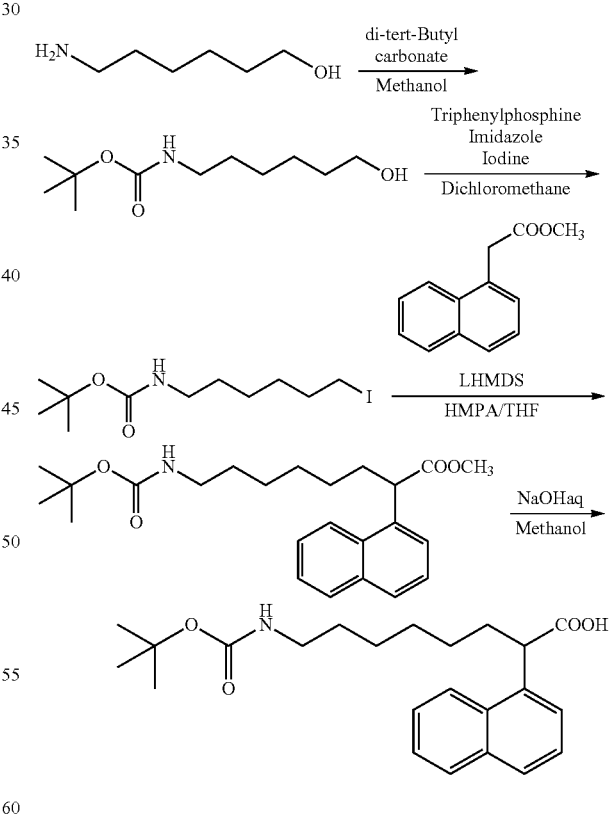

Compound #3 mentioned later in Examples can be synthesized as the compound represented by the formula (vi) from trans-1-phenyl-2-buten-1-one and indole according to a method described in Sayed, G. H. et al, "Synthesis and reactions of some β-aroyl-α-(indol-3-yl)propionic acids" Journal of the Chemical Society of Pakistan, 7 (4), 263-72; 1985 as shown in the following scheme:

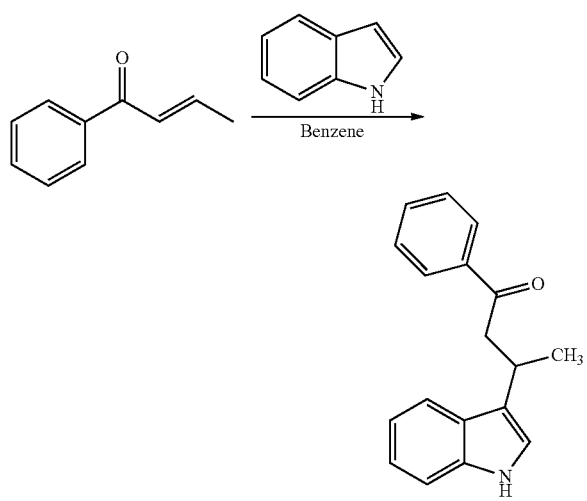

Of the compounds included in the compound group 2 of the present invention, specific examples of a compound having the effect of promoting (enhancing) ATP production (expression) can include 36 types of compounds (compounds mentioned later in Examples [#1 to 15, 17 to 31, and 34 to 39]). Among them, examples of a compound that increases ATP concentration in cells by two or more times the normal level at least in 3 hours can include 23 types of compounds (#3 to 7, 9 to 15, 18 to 22, 27 to 30, 34, and 36). Examples of a compound that increases ATP concentration in cells by five or more times the normal level at least in 6 hours can include 8 types of compounds (#1 to 8). Examples of a compound that increases ATP concentration in cells by 1.5 or more times the normal level at least in 24 hours can include 13 types of compounds (#12 to 15, 18 to 22, 27, 29, 30, and 38).

Examples of the erythropoietin expression-enhancing agent or the therapeutic agent for a mitochondrial disease of the present invention or the ATP production-promoting agent of an alternative embodiment can include the agent further supplemented, if necessary, with pharmaceutically acceptable usual formulation ingredients such as a carrier, a binder, a stabilizer, an excipient, a diluent, a pH buffer, a disintegrant, a tonicity agent, an additive, a coating agent, a solubilizer, a lubricant, a glidant, a solubilization aid, a lubricating agent, a flavoring agent, a sweetener, a solvent, a gelling agent, and a nutrient. Specific examples of such formulation ingredients can include water, saline, animal fat and oil, plant oil, lactose, starch, gelatin, crystalline cellulose, gum, talc, magnesium stearate, hydroxypropylcellulose, polyalkylene glycol, polyvinyl alcohol, and glycerin.

The synthesized compound can be confirmed to have the effect of enhancing erythropoietin expression, by analyzing the mRNA expression of the erythropoietin gene or the expression of the protein (erythropoietin) translated from the mRNA by use of a molecular biological approach known in the art. Specific examples of the method for analyzing the mRNA expression of the erythropoietin gene can include a method such as quantitative RT-PCR (reverse transcription polymerase chain reaction), RT-PCR, and Southern blotting. Specific examples of the method for analyzing the expression of the erythropoietin protein can include a method such as Western blotting, reporter assay using a plasmid having an insert of a reporter gene such as GFP (green fluorescent protein) gene or luciferase gene downstream of an erythropoietin gene promoter, and mass spectrometry.

The synthesized compound can be confirmed to have the effect of promoting ATP production, by use of a commercially available kit, apparatus, and the like that can measure ATP concentration. For example, the ATP concentration can be measured using a commercially available kit such as ADP/ATP-related assay kit series (manufactured by BioAssay Systems) or ATP Assay Reagent of "Cells" (manufactured by Toyo B-Net Co., Ltd.) and a luminometer such as AB-2300 Luminescencer JNR II (manufactured by ATTO Corp.) or GloMa 96 Microplate Luminometer (manufactured by Promega K.K.).

The anemia that can be treated and/or prevented by the therapeutic or preventive drug for anemia of the present invention is not particularly limited as long as the anemia is associated with a disease caused by reduced erythropoietin expression (production) or reduced erythropoietin reactivity. Specific examples thereof can include anemia associated with a disease such as a collagen disease (chronic rheumatoid arthritis, systemic lupus erythematosus, etc.), a chronic infection (tuberculosis, infective endocarditis, hepatic abscess, etc.), an allergic disease (atopic dermatitis, psoriasis, etc.), an autoimmune disease (rheumatism, multiple sclerosis, etc.), a tumor (ovary tumor, melanoma, etc.), chronic renal failure, hypothyroidism, amyotrophic lateral sclerosis (ALS), and the mitochondrial disease mentioned above.

The liver function-improving agent of the present invention has an effect of improving (suppressing) deterioration in liver function (liver dysfunction) caused by excessive consumption of alcohol, viral infection, liver cancer, smoking, stress, or the like.

The ischemic injury-improving agent of the present invention has an effect of improving (suppressing) ischemic injury that occurs in living tissues during ischemia, or ischemic injury that occurs during reperfusion after ischemia (ischemia-reperfusion injury). Examples of such ischemic injury or ischemia-reperfusion injury can include a cardiac disorder (ischemic heart disease, myocardial infarction, etc.), a cerebrovascular disorder (mitochondrial encephalopathy, cerebral thrombosis, cerebral infarction, etc.), a spinal vascular disorder (spinal infarction, etc.), a renal disorder (nephritis, renal failure, etc.), a hepatic disorder (fulminant hepatitis, etc.), a lung disorder (acute lung injury, adult respiratory distress syndrome [ARDS], etc.), and a pancreatic disorder (pancreatitis, etc.).

The renal protective agent of the present invention has an effect of protecting kidney functions by improving (suppressing) kidney damage caused by the adverse reaction of a drug such as cisplatin, streptomycin, 5-FU, indomethacin, chlorothiazide, or phenobarbital, or kidney damage caused by various diseases including chronic renal failure, diabetic nephropathy, glomerulonephritis, immune complex nephritis, acute renal failure, and uremia.

The insulin secretagogue of the present invention has an effect of improving (suppressing) reduced insulin secretion caused by obesity, hyperlipidemia, type 2 diabetes mellitus, hypoglycemia, hypertension, diabetic neuropathy, diabetic nephropathy, diabetic retinopathy, edema, insulin resistance, unstable diabetes, fatty atrophy, insulin allergy, insulinoma, or the like. Use of the insulin secretagogue of the present invention can normally regulate insulin secretion.

The therapeutic or preventive drug for anemia, the liver function-improving agent, the ischemic injury-improving agent, the renal protective agent, or the insulin secretagogue of the present invention is not particularly limited as long as the agent contains the erythropoietin expression-enhancing agent of the present invention. Examples thereof can include the agent further supplemented with pharmaceutically acceptable usual formulation ingredients such as a carrier, a binder, a stabilizer, an excipient, a diluent, a pH buffer, a disintegrant, a tonicity agent, an additive, a coating agent, a solubilizer, a lubricant, a glidant, a solubilization aid, a lubricating agent, a flavoring agent, a sweetener, a solvent, a gelling agent, and a nutrient. Specific examples of such formulation ingredients can include water, saline, animal fat and oil, plant oil, lactose, starch, gelatin, crystalline cellulose, gum, talc, magnesium stearate, hydroxypropylcellulose, polyalkylene glycol, polyvinyl alcohol, and glycerin.

Examples of the administration mode of the erythropoietin expression-enhancing agent, the therapeutic or preventive drug for anemia, the liver function-improving agent, the ischemic injury-improving agent, the renal protective agent, the insulin secretagogue, or the therapeutic agent for a mitochondrial disease of the present invention, or the ATP production-promoting agent of an alternative embodiment can include oral administration based on administration in a dosage form such as powders, granules, a tablet, a capsule, a syrup, or a suspension, and parenteral administration based on injection in a dosage form such as a solution, an emulsion, or a suspension or administration into the nasal cavity in the form of a spray.

Hereinafter, the present invention will be described more specifically with reference to Examples. However, the technical scope of the present invention is not intended to be limited by these examples.

EXAMPLE 1

Synthesis of Compound

Starting materials for synthesis, reaction reagents, etc., for use in methods for synthesizing compounds shown below are general commercially available products. As for reaction solvents and reaction temperatures, a reaction is carried out using a solvent and a temperature usually used for the reaction, unless otherwise specified. Each reaction is carried out in an argon or dried nitrogen atmosphere.

Synthesis of Compound #1

4-Phenyl-2-(4-chloro-1H-indol-3-yl)-4-oxo-butane (compound #1) was synthesized by a method for synthesizing compound #20 mentioned later using 4-chloroindole instead of indole.

Synthesis of Compound #2 and Compound #3

4-(4-Chlorophenyl)-2-(1H-indol-3-yl)-4-oxo-butanoic acid (compound #2) and 3-(1H-indol-3-yl)-1-oxo-1-phenyl-butane (compound #3) were each synthesized according to a method described in Sayed, G. H. et al, "Synthesis and reactions of some β-aroyl-α-(indol-3-yl)propionic acids" Journal of the Chemical Society of Pakistan, 7 (4), 263-72; 1985.

Synthesis of Compound #4

Trans-4-(4-fluorophenyl)-4-oxo-2-butenoic Acid

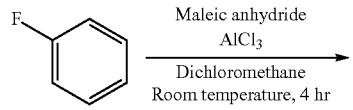

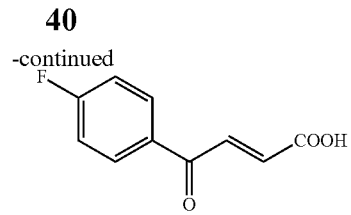

In a 50-mL round-bottomed flask filled with nitrogen, fluorobenzene (0.50 g, 5.21 mmol) was dissolved in dichloromethane (20 mL). To the solution, maleic anhydride (0.51 g, 5.20 mmol) and aluminum chloride (1.40 g, 10.49 mmol) were added, and the mixture was stirred at room temperature for 4 hours. The reaction solution was pH-adjusted to 1 by the addition of 1 N hydrochloric acid (10 mL), followed by extraction with ethyl acetate (40 mL) three times. The organic layer was washed with brine and dried over anhydrous sodium sulfate. The solvent was distilled off under reduced pressure, and then, the residue was purified by recrystallization (benzene) to obtain trans-4-(4-fluorophenyl)-4-oxo-2-butenoic acid (0.57 g, yield: 56%); Melting point: 114.8 to 119.6° C.; $^1$H NMR (CDCl$_3$): δ 8.06 (m, 2H), 7.98 (d, J=15.4 Hz, 1H), 7.21 (m, 2H), 6.90 (d, J=15.4 Hz, 1H); $^{13}$C NMR (CDCl$_3$): δ 187.5, 170.7, 166.3 (d, $J_{C-F}$=255.5 Hz), 138.0, 132.8 (d, $J_{C-F}$=3.2 Hz), 131.7 (d, $J_{C-F}$=9.9 Hz), 131.6, 116.2 (d, $J_{C-F}$=22.1 Hz); IR (neat): 2972, 1705, 1665 cm$^{-1}$; FAB-MS m/z [M+H]$^+$ calcd for 195 ($C_{11}H_{10}O_3$), found 195.

4-(4-Fluorophenyl)-2-(1H-indol-3-yl)-4-oxo-butanoic Acid (Compound #4)

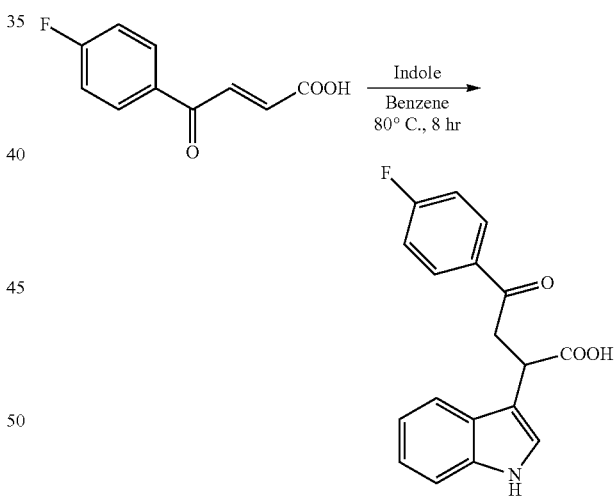

In a 30-mL round-bottomed flask, trans-4-(4-fluorophenyl)-4-oxo-2-butenoic acid (0.21 g, 1.08 mmol) was dissolved in benzene (10 mL). To the solution, indole (0.26 g, 2.19 mmol) was added, and the mixture was stirred at 80° C. for 8 hours and stirred until the temperature became room temperature. The solvent in the reaction solution was distilled off under reduced pressure, and the residue was purified by silica gel column chromatography (chloroform:methanol=20:1) to obtain 4-(4-fluorophenyl)-2-(1H-indol-3-yl)-4-oxo-butanoic acid (compound #4) (0.15 g, yield: 47%); Melting point: 161.6 to 166.6° C.; $^1$H NMR (DMSO-d$_6$): δ 8.13 (m, 2H), 7.68 (d, J=7.9 Hz, 1H), 7.35 (m, 4H), 7.09 (t, J=7.2 Hz, 1H), 7.00 (t, J=7.1 Hz, 1H), 4.34 (dd, J=10.7, 3.9 Hz, 1H), 4.03 (dd, J=18.1, 10.7 Hz, 1H), 3.34 (dd, J=18.1, 3.9 Hz, 1H); $^{13}$C NMR (DMSO-d$_6$): δ 197.96, 175.61, 166.00 (d, J$_{C-F}$=250.0 Hz), 137.16, 134.11, 131.93 (d, J$_{C-F}$=10.0 Hz), 127.15, 124.16, 122.07, 119.97, 119.53, 116.6 (d, J$_{C-F}$=22.0 Hz), 112.79, 112.42, 42.03, 38.57; IR (neat): 3419, 2925, 1679 cm$^{-1}$; HRFAB m/z [M+H]$^+$ calcd for 312.1036 (C$_{19}$H$_{17}$NO$_3$), found 312.1028.

Synthesis of Compound #5 trans-4-(2,4-Difluorophenyl)-4-oxo-2-butenoic Acid

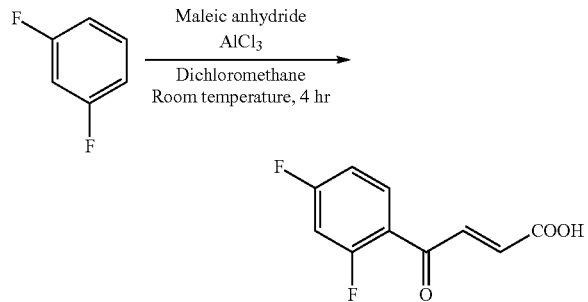

In a 50-mL round-bottomed flask filled with nitrogen, 1,3-difluorobenzene (0.51 g, 4.47 mmol) was dissolved in dichloromethane (20 mL). To the solution, maleic anhydride (0.43 g, 4.46 mmol) and aluminum chloride (1.20 g, 9.01 mmol) were added, and the mixture was stirred at room temperature for 4 hours and stirred until the temperature became room temperature. The reaction solution was pH-adjusted to 1 by the addition of 1 N hydrochloric acid (10 mL), followed by extraction with ethyl acetate (40 mL) three times. The organic layer was washed with brine and dried over anhydrous sodium sulfate. The solvent was distilled off under reduced pressure, and then, the residue was purified by recrystallization from benzene to obtain trans-4-(2,4-difluorophenyl)-4-oxo-2-butenoic acid (0.57 g, yield: 56%); Melting point: 114.8 to 119.6° C.; $^1$H NMR (acetone-d$_6$): δ 7.98 (m, 1H), 7.71 (dd, J$_{H-F}$=15.6, 3.4 Hz, 1H), 7.23 (m, 2H), 6.75 (dd, J$_{H-F}$=15.6, 1.2 Hz, 1H); $^{13}$C NMR (acetone-d$_6$): δ 187.2 (d, J$_{C-F}$=2.6 Hz), 166.9 (dd, J$_{C-F}$=254.5, 12.3 Hz), 166.4, 163.4 (dd, J$_{C-F}$=254.5, 12.9 Hz), 140.0 (d, J$_{C-F}$=6.1 Hz), 134.0 (dd, J$_{C-F}$=10.9, 3.6 Hz), 133.0 (d, J$_{C-F}$=1.6 Hz), 123.3 (dd, (J$_{C-F}$=12.4, 3.6 Hz), 113.4 (dd, J$_{C-F}$=21.5, 3.6 Hz), 105.8 (dd, J$_{C-F}$=27.3, 26.3 Hz); IR (neat): 2917, 1697, 1661 cm$^{-1}$; FAB-MS m/z [M+H$^+$] calcd for 213 (C$_{11}$H$_{10}$O$_3$), found 213.

4-(2,4-Difluorophenyl)-2-(1H-indol-3-yl)-4-oxo-butanoic Acid (Compound #5)

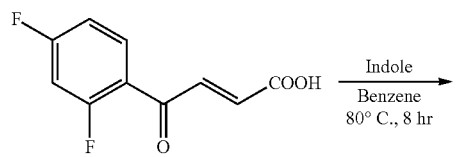

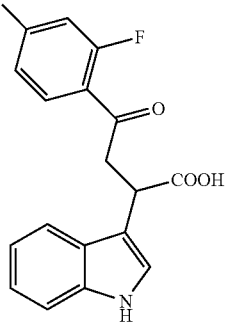

In a 30-mL round-bottomed flask, trans-4-(2,4-difluorophenyl)-4-oxo-2-butenoic acid (0.39 g, 1.84 mmol) was dissolved in benzene (10 mL). To the solution, indole (0.43 g, 2.19 mmol) was added, and the mixture was stirred 80° C. for 8 hours and stirred until the temperature became room temperature. The solvent in the reaction solution was distilled off under reduced pressure, and the residue was purified by silica gel column chromatography (chloroform:methanol=20:1) to obtain 4-(2,4-difluorophenyl)-2-(1H-indol-3-yl)-4-oxo-butanoic acid (0.15 g, yield: 51%); Melting point: 180.2 to 184.6° C.; $^1$H NMR (DMSO-d$_6$): δ 7.98 (m, 1H), 7.65 (d, J=7.9 Hz, 1H), 7.37 (d, J=8.1 Hz, 1H), 7.42 (m, 1H), 7.28 (d, J=2.3 Hz, 1H), 7.24 (m, 1H), 7.09 (t, J=7.1 Hz, 1H), 7.01 (t, J=7.5 Hz, 1H), 4.34 (dd, J=10.5, 3.5 Hz, 1H), 3.90 (ddd, =18.5, 10.6, 2.4 Hz, 1H), 3.30 (ddd, J$_{H-F}$=18.5, 6.1, 3.5 Hz, 1H); $^{13}$C NMR (DMSO-d$_6$): δ 195.2 (d, J$_{C-F}$=4.1 Hz), 174.8, 165.2 (d, J$_{C-F}$=253.0, 13.4 Hz), 162.2 (d, J$_{C-F}$=255.5, 13.4 Hz), 136.4, 132.7 (dd, J$_{C-F}$=10.8, 4.1 Hz), 126.3, 123.3, 122.2 (dd, J$_{C-F}$=12.3, 3.6 Hz), 121.4, 119.1, 118.8, 112.6 (dd, J$_{C-F}$=21.1, 3.6 Hz), 111.9, 111.8, 105.4 (dd, J$_{C-F}$=26.1 Hz), 45.6 (d, J$_{C-F}$=6.3 Hz), 37.9; IR (neat): 3382, 2919, 1678 cm$^{-1}$; HRFAB m/z [M+H]$^+$ calcd for 332.1036 (C$_{19}$H$_{17}$NO$_3$), found 312.1028.

Synthesis of Compound #6 trans-4-(2,4-Dimethylphenyl)-4-oxo-2-butenoic Acid

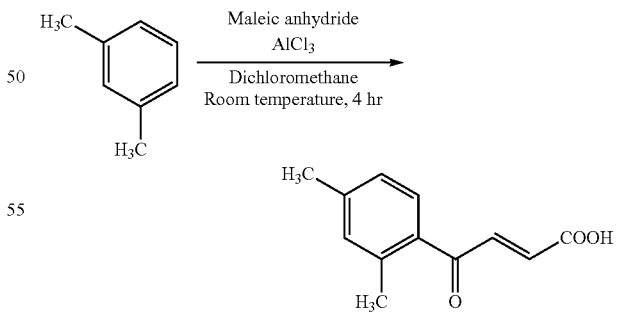

In a 50-mL round-bottomed flask filled with nitrogen, m-xylene (1.00 g, 9.42 mmol) was dissolved in dichloromethane (40 mL). To the solution, maleic anhydride (0.93 g, 9.42 mmol) and aluminum chloride (2.51 g, 18.84 mmol) were added, and the mixture was stirred at room temperature for 4 hours. The reaction solution was pH-adjusted to 1 by the addition of 1 N hydrochloric acid (10 mL), followed by extraction with ethyl acetate (40 mL) three times. The organic layer was washed with brine and dried over anhydrous sodium sulfate. The solvent was distilled off under reduced pressure, and then, the residue was purified by recrystallization (benzene) to obtain trans-4-(2,4-dimethylphenyl)-4-oxo-2-butenoic acid (1.49 g, yield: 77%); Melting point: 85.4 to 88.8° C.; $^1$H NMR (CDCl$_3$): δ 7.75 (d, J=15.6 Hz, 1H), 7.56 (d, J=8.2 Hz, 1H), 7.10 (m, 2H), 6.70 (d, J=15.6 Hz, 1H), 2.50 (s, 3H), 2.38 (s, 3H); $^{13}$C NMR (CDCl$_3$): δ 192.5, 170.9, 143.1, 141.7, 139.5, 133.6, 133.0, 130.9, 130.0, 126.4, 21.5, 21.2; IR (neat): 2986, 1703, 1667 cm$^{-1}$; FAB-MS m/z [M+H]$^+$ calcd for 205 (C$_{12}$H$_{12}$O$_3$), found 205.

4-(2,4-Dimethylphenyl)-2-(1-propyl-1H-indol-3-yl)-4-oxo-butanoic Acid (Compound #6)

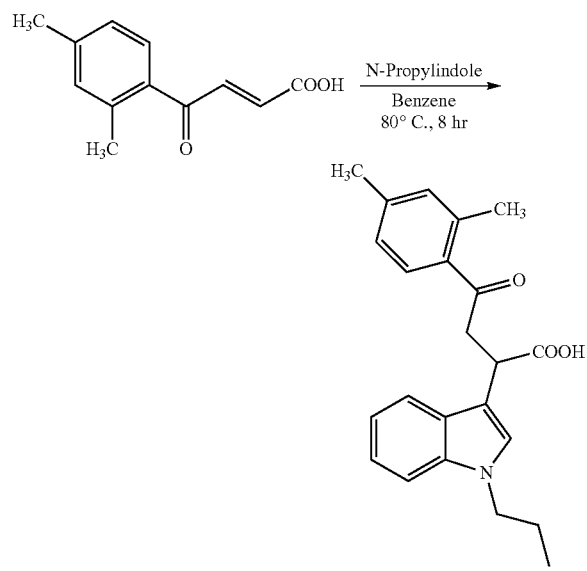

In a 30-mL round-bottomed flask, trans-4-(2,4-dimethylphenyl)-4-oxo-2-butenoic acid (0.50 g, 2.45 mmol) was dissolved in benzene (10 mL). To the solution, N-propylindole (0.85 g, 4.90 mmol) was added, and the mixture was stirred at 80° C. for 8 hours and stirred until the temperature became room temperature. The solvent in the reaction solution was distilled off under reduced pressure, and the residue was purified by silica gel column chromatography (chloroform:acetone=5:1) to obtain 4-(2,4-dimethylphenyl)-2-(1-propyl-1H-indol-3-yl)-4-oxo-butanoic acid (0.98 g, yield: 67%); Melting point: 139 to 141° C.; $^1$H NMR (400 MHz, CDCl$_3$): δ 7.70 (d, J=7.8 Hz, 1H), 7.59 (d, J=7.8 Hz, 1H), 7.28 (d, J=8.2 Hz, 1H), 7.18 (t, J=15.1 Hz, 1H), 7.07 (m, 2H), 6.99 (d, J=8.7 Hz, 2H), 4.56 (dd, J=6.0, 4.1 Hz, 1H), 3.97 (m, 2H), 3.92 (m, 1H), 3.28 (dd, J=17.8, 4.1 Hz, 1H), 2.43 (s, 3H), 2.30 (s, 3H), 1.80 (m, 2H), 0.89 (t, J=14.7, 3H); $^{13}$C NMR (100 MHz, CDCl$_3$): δ 200.9, 179.7, 142.3, 138.9, 136.3, 134.1, 132.8, 129.1, 126.7, 126.2, 126.1, 121.7, 119.4, 119.2, 110.6, 109.5, 48.0, 44.0, 38.0, 23.4, 21.5, 21.3, 11.5; IR (neat): 3428, 2923, 1707 cm$^{-1}$; FAB-MS m/z [M+H]$^+$ calcd for 322.1443 (C$_{19}$H$_{17}$NO$_3$), found 364.

4-Phenyl-2-(1H-5-ethoxyindol-3-yl)-4-oxo-butanoic acid (compound #7) was synthesized in the same way as in compound #20 using 5-ethoxyindole instead of indole.

Compounds #8, 13 to 15, 17 to 19, and 21 to 25 were each synthesized with methyl N-methoxycarbonylindoleacetate as a key intermediate.

1-Methoxycarbonylindole-3-acetic Acid Methyl Ester

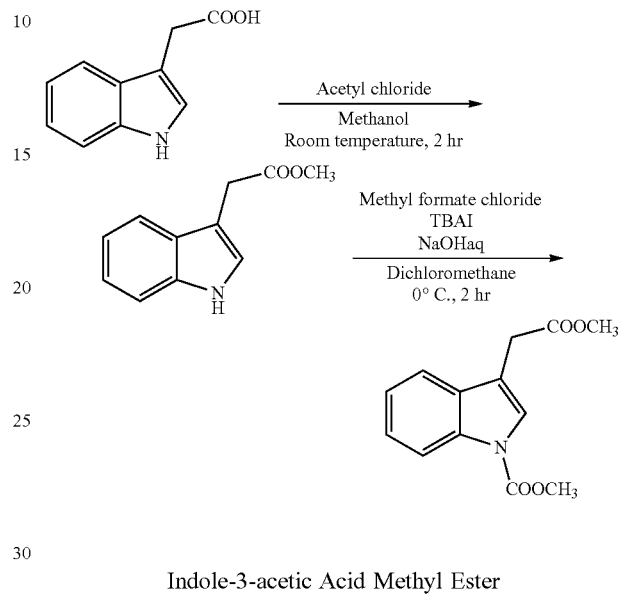

Indole-3-acetic Acid Methyl Ester

Indole-3-acetic acid (2.00 g, 11.42 mmol) was dissolved in methanol (40 ml). To this solution, acetyl chloride (0.5 ml, 6.688 mmol) was added dropwise, and the mixture was stirred at room temperature for 2 hours. After the reaction was confirmed by TLC to be complete, the reaction was quenched by the addition of a saturated aqueous solution of sodium bicarbonate, followed by extraction with ethyl acetate (50 ml) three times. The organic layer was washed twice with brine and dried over anhydrous sodium sulfate. The solvent was distilled off under reduced pressure, and then, the residue was purified by silica gel column chromatography (hexane:ethyl acetate=7:3) to obtain indole-3-acetic acid methyl ester (2.14 g, yield: 99%): $^1$H NMR (400 MHz, CDCl$_3$): δ 8.13 (s, 1H), 6.97 (s, 1H), 7.59 (d, J=7.7 Hz, 1H), 7.23 (d, J=7.9 Hz, 1H), 7.10-7.19 (m, 2H), 3.67 (s, 3H), 3.76 (s, 2H); $^{13}$C NMR (100 MHz, CDCl$_3$): δ 172.3, 136.0, 127.1, 123.2, 122.0, 119.5, 118.6, 111.2, 108.0, 51.9, 31.0; IR (neat): 3410, 1730, 1458, 1435, 1337, 1164, 1095, 1011 cm$^{-1}$; EI-MS: m/z [M+H]$^+$ 189.

1-Methoxycarbonyl-3-indoleacetic Acid Methyl Ester

Methyl indole-3-acetate (2.00 g, 10.57 mmol) was dissolved in dichloromethane (30 ml). To this solution, tetrabutylammonium iodide (TBAI, 30.0 mg, 0.081 mmol) and a 30% aqueous sodium hydroxide solution (24 ml) were added, and the mixture was cooled to 0° C. To the reaction solution, methyl formate chloride (1.96 g, 20.73 mmol) was added, and the mixture was stirred at 0° C. for 2 hours. After the reaction was confirmed by TLC to be complete, the reaction was quenched by the addition of 6 N hydrochloric acid. Water (50 ml) was added thereto, followed by extraction with chloroform (50 ml) three times. The organic layer was washed twice with brine and dried over anhydrous sodium sulfate. The solvent was distilled off under reduced pressure, and then, the residue was purified by silica gel column chromatography (hexane:ethyl acetate=8:2) to obtain methyl N-methoxycarbonylindole-3-acetate (2.26 g, yield: 87%): $^1$H NMR (400 MHz, CDCl$_3$): δ 8.18 (d, J=7.0 Hz, 1H), 7.59 (s, 1H), 7.53 (d, J=7.7 Hz, 1H), 7.35 (t, J=7.5 Hz, 1H), 7.27 (t, J=7.4 Hz, 1H), 4.00 (s, 3H), 3.72 (s, 3H), 3.71 (s, 2H); $^{13}$C NMR (100 MHz, CDCl$_3$): δ 171.1, 151.1, 135.2, 129.9, 124.6, 123.8, 122.8, 118.9, 115.0, 113.8, 53.5, 51.9, 30.6; IR (neat): 1746, 1455, 1382, 1258, 1164, 1089, 1018 cm$^{-1}$; EI-MS: m/z [M]$^+$ 247.

Compounds #8 and 9 were each synthesized according to a method described in International Publication No. WO 2010/045451.

Synthesis of Compound #8

2-(N-tert-Butoxycarbonyl-4-piperidinyl)ethanol

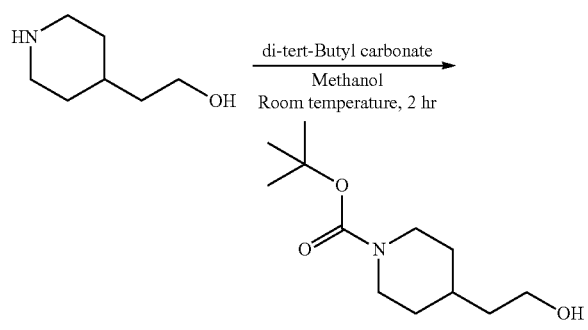

2-(4-Piperidinyl)ethanol (1.0 g, 7.7 mmol) was dissolved in methanol (50 ml). To this solution, di-tert-butyl carbonate (2.0 g, 9.3 mmol) was added, and the mixture was stirred at room temperature for 2 hours. After the reaction was confirmed by TLC to be complete, the solvent was distilled off under reduced pressure, and the residue was purified by silica gel column chromatography (hexane:acetone=9:1) to obtain N-tert-butoxycarbonyl-2-(4-piperidinyl)ethanol (1.68 g, yield: 95%).

Ethane 2-(N-tert-butoxycarbonyl-4-piperidinyl)-1-iodide

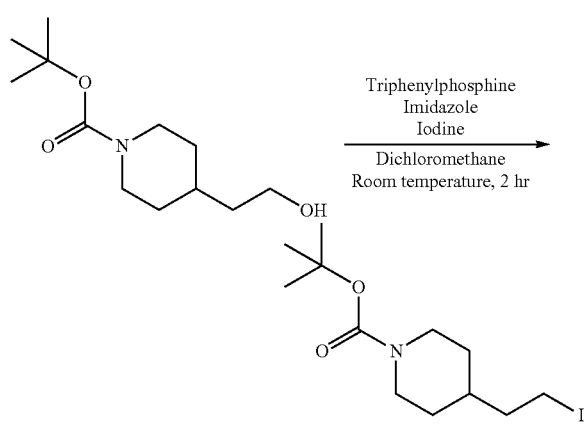

Triphenylphosphine (2.56 g, 9.760 mmol) and imidazole (0.66 g, 9.694 mmol) were dissolved in dichloromethane (15 ml), and the solution was stirred for 5 minutes. Then, iodine (2.47 g, 9.732 mmol) was added thereto, and the mixture was stirred for 10 minutes. A dichloromethane (4 ml) solution of N—N-tert-butoxycarbonyl-2-(4-piperidinyl) ethanol (1.49 g, 6.497 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane:ethyl acetate=9:1) to obtain ethane N-tert-butoxycarbonyl-2-(4-piperidinyl)-1-iodide (2.13 g, yield: 96%).

α-[2-(N-tert-Butoxycarbonyl-4-piperidinyl)-1-ethyl]-1-methoxycarbonyl-3-indoleacetic Acid Methyl Ester

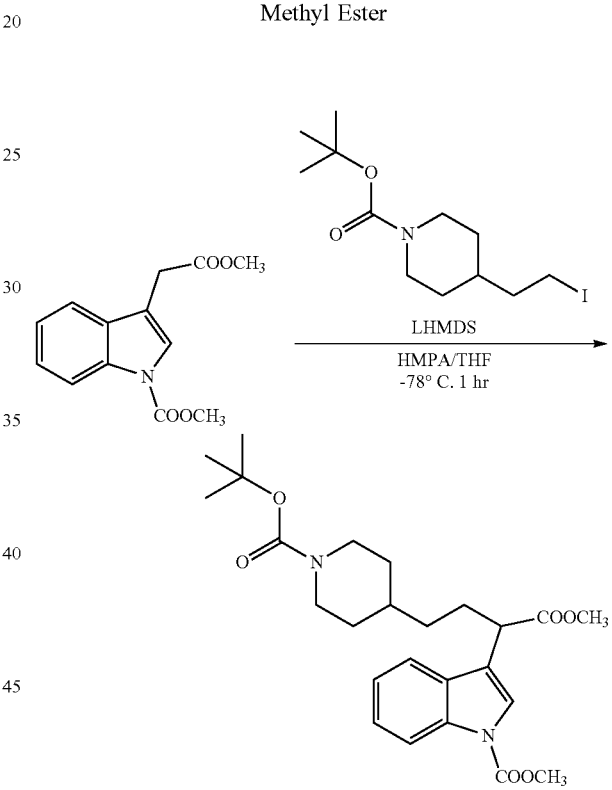

In a nitrogen atmosphere, 1-methoxycarbonyl-3-indoleacetic acid methyl ester (500 mg, 2.022 mmol) and hexamethylphosphoric triamide (HMPA, 1.81 g, 10.11 mmol) were dissolved in tetrahydrofuran (4 ml), and the solution was cooled to −78° C. A 1.5 M solution of lithium diisopropylamide (LDA) in cyclohexane (2.16 ml, 1.6 eq) was slowly added dropwise thereto, and the mixture was stirred at −78° C. for 0.5 hours. To this reaction solution, a tetrahydrofuran (2 ml) solution of ethane 2-(N-tert-butoxycarbonyl-4-piperidinyl)-1-iodide (686 mg, 2.022 mmol) was slowly added dropwise, and the mixture was stirred at −78° C. for 1 hour. After the reaction was confirmed by TLC to be complete, the temperature was adjusted to 0° C., and the reaction was quenched by the addition of water (15 ml), followed by extraction with ethyl acetate (15 ml) three times. The organic layer was washed twice with brine and dried over anhydrous sodium sulfate. The solvent was distilled off under reduced pressure, and then, the residue was purified by silica gel column chromatography (hexane:ethyl acetate=8:2) to obtain α-2-(N-tert-butoxycarbonyl-4-piperidinyl)-ethyl-1-methoxycarbonyl-3-indoleacetic acid methyl ester (626 mg, yield: 68%): $^1$H NMR (400 MHz, CDCl$_3$): δ 8.19 (m, 1H), 7.61 (d, J=7.8 Hz, 1H), 7.56 (s, 1H), 7.35 (t, J=7.7 Hz, 1H), 7.25-7.30 (m, 1H), 3.79-4.15 (m, 5H), 3.77 (t, J=7.6 Hz, 1H), 3.68 (s, 3H), 2.65 (m, 2H), 2.05 (m, 2H), 1.65 (m, 2H), 1.25-1.50 (m, 12H), 1.05-1.19 (m, 2H); $^{13}$C NMR (100 MHz, CDCl$_3$): δ 173.9, 168.0, 154.8, 135.4, 129.3, 124.8, 123.1, 122.9, 119.2, 119.2, 115.2, 79.1, 53.7, 53.0, 52.1, 48.9, 43.7, 42.7, 35.9, 34.3, 32.0, 29.5, 28.4; FAB-MS: m/z [M+H]$^+$ 459.

α-[2-(1-Acetyl-4-piperidinyl)-ethyl]-1-methoxycarbonyl-3-indoleacetic Acid Methyl Ester column chromatography (chloroform:acetone=9:1) to obtain α-[2-(1-acetyl-4-piperidinyl)-ethyl]-1-methoxycarbonyl-3-indoleacetic acid methyl ester (53.9 mg, yield: 65%): $^1$H NMR (400 MHz, CDCl$_3$): δ 8.18 (d, J=6.7 Hz, 1H), 7.61 (d, J=7.8 Hz, 1H), 7.56 (s, 1H), 7.35 (t, J=8.4 Hz, 1H), 7.25-7.28 (m, 1H), 4.57 (d, J=12.8 Hz, 1H), 4.03 (s, 3H), 3.73-3.79 (m, 2H), 3.68 (s, 3H), 2.99 (t, J=12.9 Hz, 1H), 2.50 (t, J=12.6 Hz, 1H), 1.91-2.19 (m, 5H), 1.73 (t, J=10.4 Hz, 2H), 1.49 (m, 1H), 1.26-1.32 (m, 2H), 1.05-1.12 (m, 2H); $^{13}$C NMR (100 MHz, CDCl$_3$): δ 173.8, 168.7, 151.2, 135.4, 129.3, 124.8, 122.9, 119.2, 119.1, 115.2, 53.7, 52.1, 46.6, 42.7, 41.7, 35.9, 34.2, 32.5, 31.6, 29.2, 21.4; FAB-MS: m/z [M+H]$^+$ 401.

α-2-(1-Acetyl-4-piperidinyl)-ethyl-3-indoleacetic Acid (Compound #8)

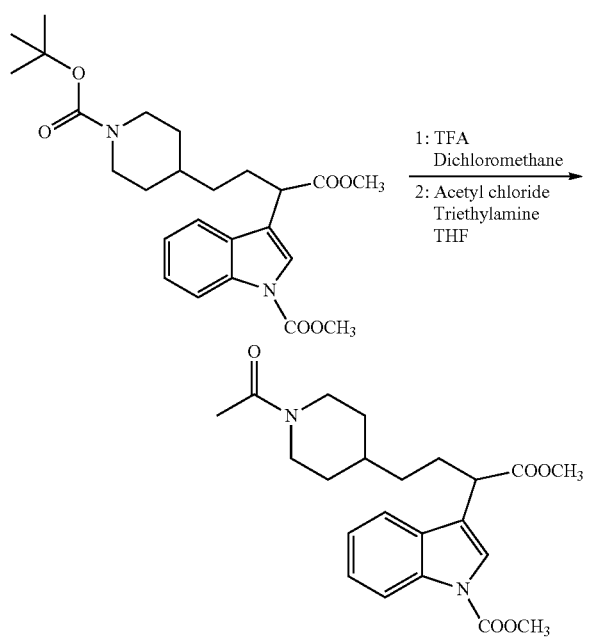

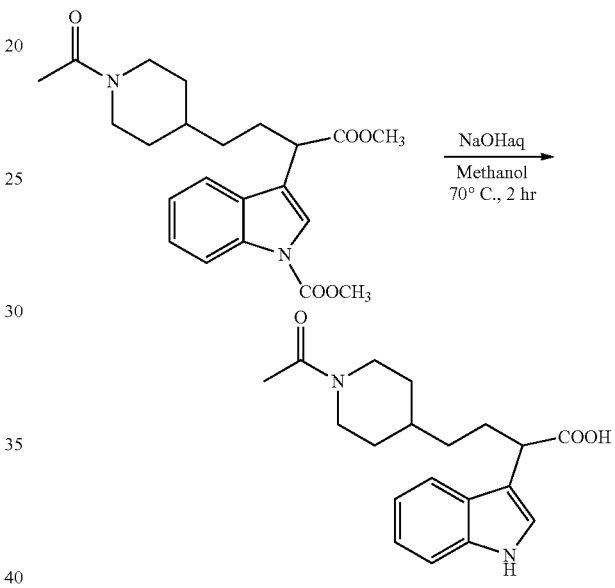

α-[2-(N-tert-Butoxycarbonyl-4-piperidinyl)-1-ethyl]-1-methoxycarbonyl-3-indoleacetic acid methyl ester (100 mg, 0.218 mmol) was dissolved in dichloromethane (2 ml). To the solution, trifluoroacetic acid (1.0 ml, 13.07 mmol) was added, and the mixture was stirred at room temperature for 5 minutes. The reaction solution was added dropwise to a 10% aqueous sodium carbonate solution (10 mL) to quench the reaction. This solution was subjected to extraction with ethyl acetate (10 mL) three times. The organic layer was washed twice with brine (10 mL) and dried over anhydrous sodium sulfate. The solvent was distilled off under reduced pressure to obtain α-[2-(4-piperidinyl)-ethyl]-1-methoxycarbonyl-3-indoleacetic acid methyl ester (74.1 mg). This compound (74.1 mg, 0.207 mmol) was dissolved in tetrahydrofuran (3 mL). To the solution, triethylamine (0.2 mL) and acetyl chloride (10 mg) were added, and the mixture was stirred at room temperature for 1.5 hours. The reaction was quenched by the addition of a saturated aqueous solution of ammonium chloride (10 mL), followed by extraction with ethyl acetate (10 mL) three times. The organic layer was washed twice with brine (10 mL) and dried over anhydrous sodium sulfate. The solvent was distilled off under reduced pressure, and then, the residue was purified by silica gel α-2-(1-acetyl-4-piperidinyl)-ethyl-N-methoxycarbonyl-3-indoleacetic acid methyl ester (48.0 mg, 0.120 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:acetone=3:2) to obtain α-2-(1-acetyl-4-piperidinyl)-ethyl-3-indoleacetic acid (compound #8) (25.5 mg, yield: 65%: $^1$H NMR (400 MHz, CDCl$_3$): δ 8.54 (s, 1H), 7.67 (d, J=7.9 Hz, 1H), 7.31 (d, J=8.0 Hz, 1H), 7.16 (t, J=7.7 Hz, 1H), 7.07-7.11 (m, 2H), 4.48 (d, J=12.7 Hz, 1H), 3.81 (t, J=7.5 Hz, 1H), 3.66 (d, J=13.2 Hz, 1H), 2.89 (t, J=12.5 Hz, 1H), 2.43 (t, J=12.6 Hz, 1H), 1.86-2.17 (m, 5H), 1.62 (t, J=16.5 Hz, 2H), 1.41 (m, 1H), 1.22-1.28 (m, 2H), 0.93-1.01 (m, 2H); $^{13}$C NMR (100 MHz, CDCl$_3$): δ 178.8, 169.3, 136.2, 126.5, 122.3, 122.0, 119.5, 119.1, 113.3, 111.4, 46.7, 43.1, 42.0, 35.7, 34.2, 32.5, 31.6, 29.7, 21.3; IR (neat): 3410, 1699, 1454, 1271 cm$^{-1}$; FAB-MS: m/z [M+H]$^+$ 329.

α-2-(1-Acetyl-4-piperidinyl)-methyl-3-indoleacetic acid (compound #9) was synthesized by the same approach as in compound #8 using N-tert-butoxycarbonyl-4-piperidinylmethanol instead of 2-(N-tert-butoxycarbonyl-4-piperidinyl)ethanol.

Synthesis of Compound #10

α-4-Aminobutyl-N-methoxycarbonyl-3-indoleacetic Acid Methyl Ester

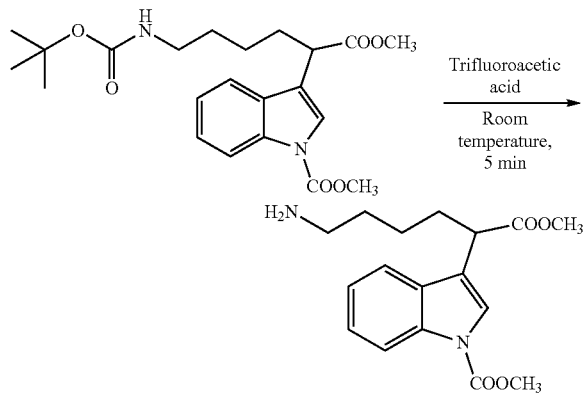

To α-(N-tert-butoxycarbonyl-4-amino-1-butyl)-1-methoxycarbonyl-3-indoleacetic acid methyl ester (150 mg, 0.358 mmol), trifluoroacetic acid (0.4 ml, 5.227 mmol) was added, and the mixture was stirred at room temperature. After 5 minutes, the reaction solution was added dropwise to an aqueous sodium bicarbonate solution to quench the reaction. Water (5 ml) was added thereto, followed by extraction with ethyl acetate (5 ml) three times. The organic layer was washed twice with brine and dried over anhydrous sodium sulfate. The solvent was distilled off under reduced pressure to obtain α-4-aminobutyl-N-methoxycarbonyl-3-indoleacetic acid methyl ester.

α-[N-(1-Acetylpyrrolidine-2-carbonyl)-4-aminobutyl]-N-methoxycarbonyl-3-indoleacetic Acid Methyl Ester

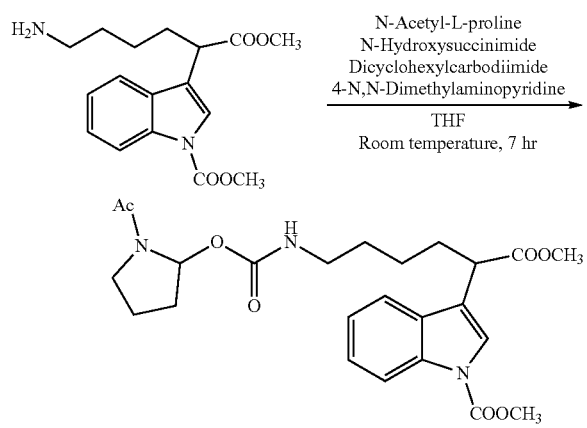

α-4-Aminobutyl-N-methoxycarbonyl-3-indoleacetic acid methyl ester (150 mg, 0.493 mmol) was dissolved in tetrahydrofuran (3 ml). To this solution, N-acetyl-L-proline (116 mg, 0.738 mmol), N-hydroxysuccinimide (85.0 mg, 0.739 mmol), dicyclohexylcarbodiimide (152 mg, 0.737 mmol), and 4-N,N-dimethylaminopyridine (72.0 mg, 0.589 mmol) were added, and the mixture was stirred at room temperature for 7 hours. The reaction was quenched with a saturated aqueous solution of ammonium chloride, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:acetone=7:3) to obtain α-[N-(1-acetylpyrrolidine-2-carbonyl)-4-aminobutyl]-N-methoxycarbonyl-3-indoleacetic acid methyl ester (107 mg, yield: 49%): $^1$H NMR (400 MHz, CDCl$_3$): δ 8.17 (d, J=7.1 Hz, 1H), 7.61 (d, J=7.7 Hz, 1H), 7.55 (s, 1H), 7.33 (t, J=7.8 Hz, 1H), 7.25 (t, J=7.4 Hz, 1H), 7.18 (s, 1H), 4.50 (d, J=7.3 Hz, 1H), 4.02 (s, 3H), 3.80 (t, J=7.6 Hz, 1H), 3.67 (s, 3H), 3.36-3.58 (m, 2H), 3.10-3.26 (m, 2H), 1.76-2.40 (m, 9H), 1.49-1.56 (m, 2H), 1.33-1.38 (m, 2H); $^{13}$C NMR (100 MHz, CDCl$_3$): δ 173.8, 171.0, 170.8, 151.1, 135.3, 129.2, 124.6, 122.9, 122.8, 119.2, 119.1, 115.0, 59.4, 53.6, 51.9, 48.1, 42.3, 38.9, 31.5, 29.0, 27.2, 24.8, 24.7, 22.3; FAB-MS: m/z [M+H]$^+$ 458.

α-[N-(1-Acetylpyrrolidine-2-carbonyl)-4-aminobutyl]-3-indoleacetic Acid (Compound #10)

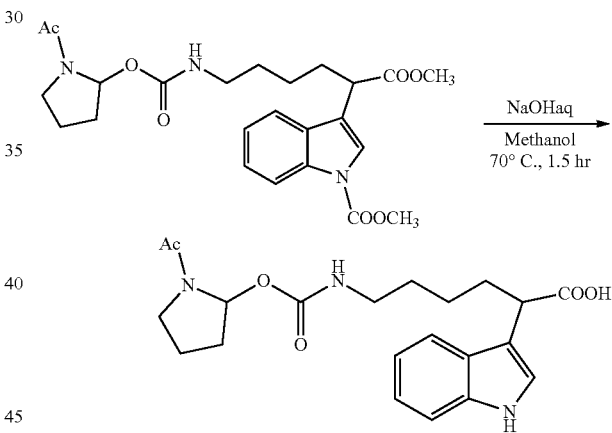

α-[N-(1-Acetylpyrrolidine-2-carbonyl)-4-aminobutyl]-N-methoxycarbonyl-3-indoleacetic acid methyl ester (80.0 mg, 0.175 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain α-[N-(1-acetylpyrrolidine-2-carbonyl)-4-aminobutyl]-3-indoleacetic acid (compound #10) (63.6 mg, yield: 94%): $^1$H NMR (400 MHz, acetone-d$_6$): δ 10.21 (s, 1H), 8.03 (s, 1H), 7.70 (d, J=7.8 Hz, 1H), 7.38 (d, J=8.0 Hz, 1H), 7.27 (s, 1H), 7.09 (t, J=7.3 Hz, 1H), 7.01 (t, J=7.6 Hz, 1H), 4.35 (d, J=7.2 Hz, 1H), 3.85 (t, J=7.6 Hz, 1H), 3.53 (m, 1H), 3.40-3.46 (m, 1H), 3.23 (m, 1H), 3.10-3.17 (m, 1H), 1.85-2.14 (m, 9H), 1.36-1.50 (m, 4H); $^{13}$C NMR (100 MHz, acetone-d$_6$): δ 175.8, 172.1, 170.3, 137.3, 127.5, 123.3, 121.9, 119.7, 119.3, 114.1, 112.0, 60.5, 48.3, 43.3, 39.2, 32.9, 32.5, 25.4, 25.1, 22.2; IR (Neat): 3300, 1634, 1456, 1245 cm$^{-1}$; FAB-MS: m/z [M+H]$^+$ 386.

Synthesis of Compound #11

α-[2-(2-Aminoethoxy)-ethyl]-N-methoxycarbonyl-3-indoleacetic Acid Methyl Ester

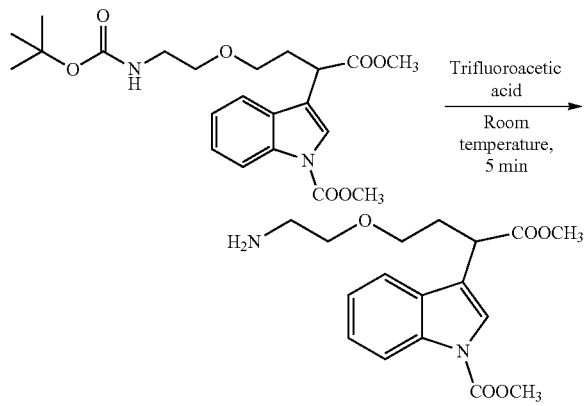

To α-[N-tert-butoxycarbonyl-(2-aminoethoxyethyl)]-1-methoxycarbonyl-3-indoleacetic acid methyl ester (140 mg, 0.322 mmol), trifluoroacetic acid (0.3 ml, 3.920 mmol) was added, and the mixture was stirred at room temperature. After 5 minutes, the reaction solution was added dropwise to an aqueous sodium bicarbonate solution to quench the reaction. Water (5 ml) was added thereto, followed by extraction with ethyl acetate (5 ml) three times. The organic layer was washed twice with brine and dried over anhydrous sodium sulfate. The solvent was distilled off under reduced pressure to obtain α-[2-(2-aminoethoxy)-ethyl]-N-methoxycarbonyl-3-indoleacetic acid methyl ester (80.0 mg, yield: 74%).

α-{N-(1-Acetylpyrrolidine-2-carbonyl)-[2-(2-aminoethoxy)-ethyl]}-N-methoxycarbonyl-3-indoleacetic Acid Methyl Ester

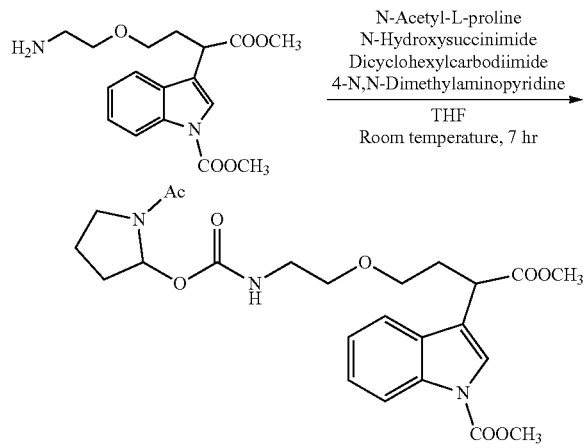

α-[2-(2-Aminoethoxy)-ethyl]-N-methoxycarbonyl-3-indoleacetic acid methyl ester (80.0 mg, 0.239 mmol) was dissolved in tetrahydrofuran (3 ml). To this solution, N-acetyl-L-proline (56.4 mg, 0.359 mmol), N-hydroxysuccinimide (41.2 mg, 0.358 mmol), dicyclohexylcarbodiimide (74.0 mg, 0.359 mmol), and 4-N,N-dimethylaminopyridine (35.0 mg, 0.286 mmol) were added, and the mixture was stirred at room temperature for 7 hours. The reaction was terminated with a saturated aqueous solution of ammonium chloride, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:acetone=7:3) to obtain α-[N-(1-acetylpyrrolidine-2-carbonyl)-4-aminobutyl]-N-methoxycarbonyl-3-indoleacetic acid methyl ester (76.1 mg, yield: 67%): $^1$H NMR (400 MHz, CDCl$_3$): δ 8.18 (d, J=7.1 Hz, 1H), 7.57-7.66 (m, 2H), 7.35 (t, J=7.7 Hz, 1H), 7.25-7.28 (m, 2H), 4.56 (t, J=8.3 Hz, 1H), 4.09 (t, J=7.6 Hz, 1H), 4.03 (s, 3H), 3.68 (s, 3H), 3.59 (t, J=9.0 Hz, 1H), 3.32-3.52 (m, 7H), 2.36-2.48 (m, 2H), 1.84-2.18 (m, 7H), 1.49-1.56 (m, 2H), 1.33-1.38 (m, 2H); $^{13}$C NMR (100 MHz, CDCl$_3$): 174.2, 171.5, 170.8, 151.1, 135.5, 129.3, 124.8, 123.1, 123.0, 119.4, 118.9, 115.2, 69.4, 68.4, 59.2, 53.8, 52.2, 48.2, 39.5, 39.2, 32.2, 27.8, 25.0, 22.5; FAB-MS: m/z [M+H]$^+$ 474.

α-[N-(1-Acetylpyrrolidine-2-carbonyl)-4-aminobutyl]-3-indoleacetic Acid (Compound #11)

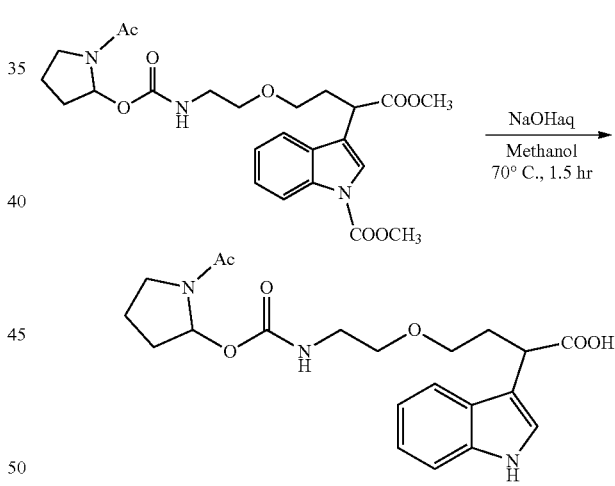

α-[N-(1-Acetylpyrrolidine-2-carbonyl)-4-aminobutyl]-N-methoxycarbonyl-3-indoleacetic acid methyl ester (60.0 mg, 0.127 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain α-[N-(1-acetylpyrrolidine-2-carbonyl)-4-aminobutyl]-3-indoleacetic acid (compound #11) (36.6 mg, yield: 72%): $^1$H NMR (400 MHz, acetone-d$_6$): δ 8.48 (d, J=13.4 Hz, 1H), 7.70 (d, J=7.9 Hz, 1H), 7.34 (d, J=8.1 Hz, 1H), 7.09-7.21 (m, 3H), 4.67 (t, J=8.3 Hz, 1H), 4.40-4.11 (m, 1H), 3.18-3.76 (m, 8H), 2.46-2.67 (m, 4H), 1.86-2.22 (m, 7H); $^{13}$C NMR (100 MHz, acetone-d$_6$): δ 178.0, 171.6, 171.2, 136.1, 126.5, 122.3, 122.0, 119.4, 118.9, 113.7, 111.2, 69.3, 68.6, 60.0, 48.5, 41.2, 39.9, 33.7, 29.1, 24.8, 22.3; IR (Neat): 3317, 1634, 1456, 1247, 1119 cm$^{-1}$; FAB-MS: m/z [M+H]$^+$ 402.

Synthesis of Compound #12

α-(N-tert-Butoxycarbonyl-6-amino-1-hexyl)-α-(1-naphthyl)-acetic Acid Methyl Ester

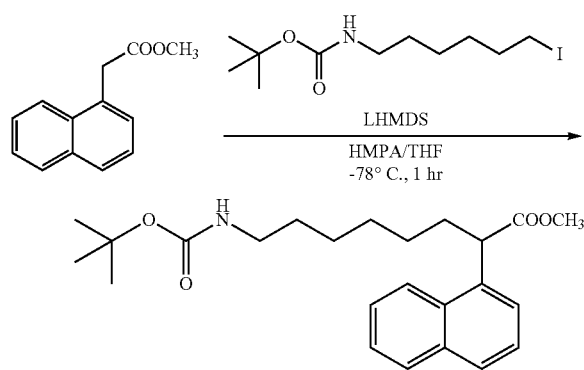

α-(1-Naphthyl)-acetic acid methyl ester (150 mg, 0.75 mmol) was dissolved in tetrahydrofuran. To the solution, hexamethylphosphoramide (HMPA, 671 mg, 3.75 mmol) was added, and the mixture was cooled to −78° C. To this solution, lithium diisopropylamide (1.5 M solution in cyclohexane, 0.75 ml, 1 mmol) was added dropwise, and the mixture was stirred at −78° C. for 30 minutes. Then, a tetrahydrofuran solution (2 mL) of N-tert-butoxycarbonyl-6-amino-1-iodohexane (270 mg, 0.82 mmol) was added dropwise thereto, and the mixture was stirred at −78° C. for hour. The temperature of the reaction solution was raised to 0° C. over 15 minutes, and then, water (50 mL) was added to the solution, followed by extraction with ethyl acetate (50 mL) twice. The organic layer was washed with a saturated ammonium chloride solution (20 mL) and subsequently brine (20 mL) and then dried over sodium sulfate to dryness under reduced pressure. The reaction product was purified by silica gel column chromatography (hexane:ethyl acetate=8:2) to obtain α-(N-tert-butoxycarbonyl-6-amino-1-hexyl)-α-(1-naphthyl)-acetic acid methyl ester (271 mg, yield: 91%): $^1$H NMR (400 MHz, CDCl$_3$): δ 8.11 (d, J=8.5 Hz, 1H), 7.83 (d, J=8.0 Hz, 1H), 7.74 (d, J=8.1 Hz, 1H), 7.40-7.54 (m, 4H), 4.71 (s, 1H), 4.36 (t, J=7.8 Hz, 1H), 3.61 (s, 3H), 3.04 (m, 2H), 2.07 (m, 2H), 1.24-1.48 (m, 17H); $^{13}$C NMR (100 MHz, CDCl$_3$): δ 174.7, 155.9, 135.3, 133.8, 131.3, 128.8, 127.5, 126.1, 125.4, 125.3, 124.6, 122.8, 78.7, 51.8, 46.5, 40.3, 32.9, 29.7, 28.9, 28.2, 27.6, 26.3; FAB-MS: m/z [M+H]$^+$ 400.

α-(N-tert-Butoxycarbonyl-6-amino-1-hexyl)-α-(1-naphthyl)-acetic Acid (Compound #12)

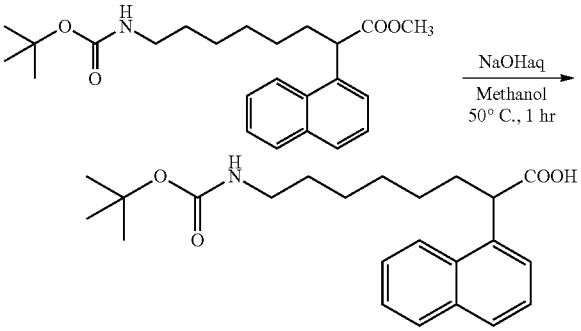

α-(N-tert-Butoxycarbonyl-6-amino-1-hexyl)-α-(1-naphthyl)-acetic acid methyl ester (100 mg, 0.25 mmol) was dissolved in a mixed solution of methanol and an aqueous sodium hydroxide solution (2 N aqueous sodium hydroxide solution:methanol=1:4, 5 mL), and the solution was heated at 50° C. for 1 hour. The reaction solution was pH-adjusted to 3.5 with 6 N hydrochloric acid, and methanol was removed by distillation under reduced pressure. To this solution, water (15 mL) was added, followed by extraction with ethyl acetate (50 mL) twice. The organic layer was washed with a saturated ammonium chloride solution (20 mL) and subsequently brine (20 mL) and then dried over sodium sulfate to dryness under reduced pressure. The reaction product was purified by silica gel column chromatography (chloroform:methanol=95:5) to obtain α-(N-tert-butoxycarbonyl-6-amino-1-hexyl)-α-(1-naphthyl)-acetic acid (compound #12) (90 mg, yield: 93%): $^1$H NMR (400 MHz, CDCl$_3$): δ 8.13 (d, J=8.4 Hz, 1H), 7.84 (d, J=7.9 Hz, 1H), 7.75 (d, J=8.1 Hz, 1H), 7.41-7.53 (m, 4H), 4.56 (s, 1H), 4.35 (t, J=7.4 Hz, 1H), 3.03 (m, 2H), 2.05 (m, 2H), 1.22-1.46 (m, 17H); $^{13}$C NMR (100 MHz, CDCl$_3$): δ 179.0, 156.0, 135.1, 133.9, 131.6, 128.9, 127.7, 126.2, 125.5, 125.4, 124.9, 123.1, 79.0, 46.6, 40.4, 32.7, 29.8, 29.0, 28.3, 27.7, 26.4; IR (neat): 3417, 1705, 1457, 1268, 1099 cm$^{-1}$; FAB-MS: m/z [M+H]$^+$ 386.

Synthesis of Compound #13

N-tert-Butoxycarbonyl-6-amino-1-hexanol

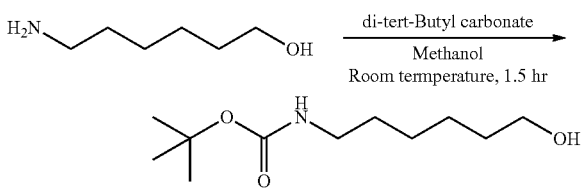

6-Amino-1-hexanol (1.0 g, 8.533 mmol) was dissolved in methanol (10 ml). To this solution, di-tert-butyl carbonate (1.86 g, 8.522 mmol) was added, and the mixture was stirred at room temperature for 1.5 hours. After the reaction was confirmed by TLC to be complete, the solvent was distilled off under reduced pressure, and the residue was purified by silica gel column chromatography (hexane:acetone=9:1) to obtain N-tert-butoxycarbonyl-6-aminohexanol (1.80 g, yield: 97%).

N-tert-Butoxycarbonyl-6-amino-1-iodohexane

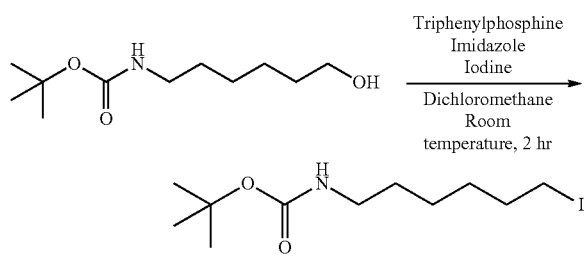

Triphenylphosphine (2.35 g, 8.96 mmol) and imidazole (0.61 g, 8.96 mmol) were dissolved in dichloromethane (15 ml), and the solution was stirred for 5 minutes. Then, iodine (2.28 g, 8.98 mmol) was added thereto, and the mixture was stirred for 10 minutes. A dichloromethane (4 ml) solution of N-tert-butoxycarbonyl-6-aminohexanol (1.3 g, 5.98 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane:ethyl acetate=9:1) to obtain N-tert-butoxycarbonyl-6-amino-1-iodohexane (1.67 g, yield: 86%).

α-Methyl-1-methoxycarbonyl-3-indoleacetic acid methyl ester was synthesized according to a method described in Katayama M, Kato Y, Marumo S. "Synthesis, absolute configuration and biological activity of both enantiomers of 2-(5,6-dichloro-3-indolyl)propionic acid: new dichloroindole auxins" Bioscience, Biotechnology, and Biochemistry, 65 (2), 270-276; 2001.

α-(N-tert-Butoxycarbonyl-6-amino-1-hexyl)-α-methyl-1-methoxycarbonyl-3-indoleacetic Acid Methyl Ester

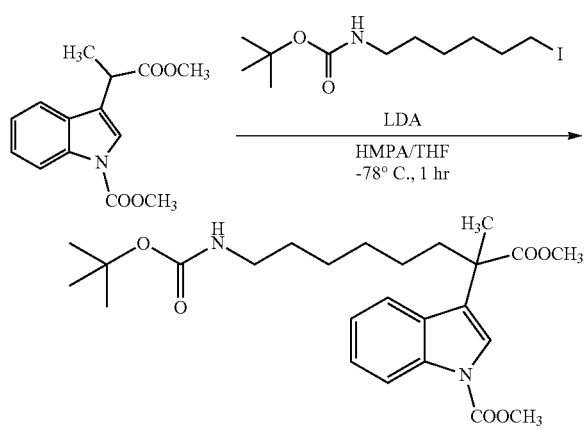

In a nitrogen atmosphere, α-methyl-1-methoxycarbonyl-3-indoleacetic acid methyl ester (83.8 mg, 0.321 mmol) was dissolved in tetrahydrofuran (2 ml), and the solution was cooled to −78° C. This solution was slowly added dropwise to a 1.0 M solution of lithium bistrimethylsilylamide (LHMDS) in tetrahydrofuran (0.69 ml, 1.5 eq), and the mixture was stirred at −78° C. for 0.5 hours. To this reaction solution, a tetrahydrofuran (1 ml) solution of N-tert-butoxycarbonyl-6-amino-1-iodohexane (105 mg, 0.321 mmol) was slowly added dropwise, and the mixture was stirred at −78° C. for 2 hours. After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=8:2) to obtain α-(N-tert-butoxycarbonyl-6-amino-1-hexyl)-α-methyl-1-methoxycarbonyl-3-indoleacetic acid methyl ester (68.6 mg, yield: 46%): $^1$H NMR (400 MHz, CDCl$_3$): δ 8.19 (d, J=6.3 Hz, 1H), 7.52 (d, J=7.9 Hz, 1H), 7.48 (s, 1H), 7.32 (t, J=7.5 Hz, 1H), 7.21 (t, J=7.5 Hz, 1H), 4.54 (s, 1H), 4.03 (s, 3H), 3.62 (s, 3H), 3.06 (m, 2H), 2.04-2.12 (m, 2H), 1.61 (s, 3H), 1.17-1.43 (m, 17H); $^{13}$C NMR (100 MHz, CDCl$_3$): δ 176.3, 155.9, 151.3, 135.8, 128.6, 124.9, 124.5, 122.8, 122.0, 120.0, 115.2, 78.9, 53.7, 52.1, 45.5, 40.4, 37.2, 29.9, 29.5, 28.3, 26.5, 24.2, 22.5; FAB-MS: m/z [M]$^+$ 460.

α-(N-tert-Butoxycarbonyl-6-amino-1-hexyl)-α-methyl-3-indoleacetic Acid (Compound #13)

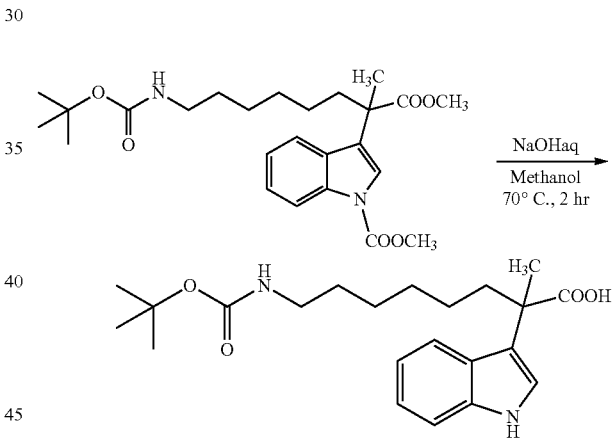

α-(N-tert-Butoxycarbonyl-6-amino-1-hexyl), α-methyl-1-methoxycarbonyl-3-indoleacetic acid methyl ester (60.0 mg, 0.130 mmol) was dissolved in methanol (4.6 ml). To the solution, water (0.4 ml) and potassium hydroxide (1.68 g, 30 mmol) were added, and the mixture was stirred at 70° C. for 2 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (benzene:acetone=85:15) to obtain α-(N-tert-butoxycarbonyl-6-amino-1-hexyl)-α-methyl-3-indoleacetic acid (compound #13) (40.0 mg, yield: 79%): $^1$H NMR (400 MHz, CDCl$_3$): δ 8.26 (s, 1H), 7.71 (d, J=8.0 Hz, 1H), 7.33 (d, J=8.0 Hz, 1H), 7.16 (t, J=7.4 Hz, 1H), 7.06 (t, J=7.3 Hz, 1H), 7.04 (s, 1H), 4.52 (s, 1H), 3.03 (m, 2H), 2.08-2.17 (m, 2H), 1.63 (s, 3H), 1.23-1.48 (m, 17H); $^{13}$C NMR (100 MHz, CDCl$_3$): δ 181.7, 156.1, 136.7, 125.5, 121.4, 120.4, 119.2, 118.8, 111.3, 79.1, 45.7, 40.5, 37.5, 29.7, 28.5, 26.5, 24.2, 22.6; IR (neat): 3415, 3339, 1699, 1519, 1460, 1369, 1249, 1170 cm$^{-1}$; FAB-MS: m/z [M+H]$^+$ 389.

Synthesis of Compound #14

2-(N-tert-Butoxycarbonyl-2-aminoethoxy)-ethanol

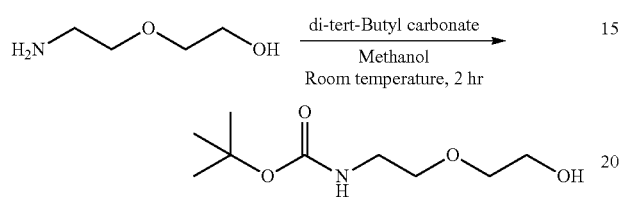

2-(2-Aminoethoxy)-ethanol (1.0 g, 9.511 mmol) was dissolved in methanol (10 ml). To this solution, di-tert-butyl carbonate (2.07 g, 9.485 mmol) was added, and the mixture was stirred at room temperature for 2 hours. After the reaction was confirmed by TLC to be complete, the solvent was distilled off under reduced pressure, and the residue was purified by silica gel column chromatography (hexane: acetone=3:2) to obtain 2-(N-tert-butoxycarbonyl-2-aminoethoxy)-ethanol (1.78 g, yield: 91%)

2-(N-tert-Butoxycarbonyl-2-aminoethoxy)-1-iodoethane

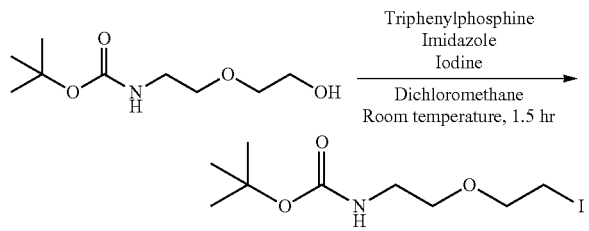

Triphenylphosphine (2.87 g, 10.94 mmol) and imidazole (0.75 g, 11.02 mmol) were dissolved in dichloromethane (15 ml), and the solution was stirred for 5 minutes. Then, iodine (2.78 g, 10.95 mmol) was added thereto, and the mixture was stirred for 10 minutes. A dichloromethane (4 ml) solution of 2-(N-tert-butoxycarbonyl-2-aminoethoxy)-ethanol (1.5 g, 7.308 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane:ethyl acetate=85:15) to obtain 2-(N-tert-butoxycarbonyl-2-aminoethoxy)-1-iodoethane (2.19 g, yield: 95%).

α-[2-(N-tert-Butoxycarbonyl-2-aminoethoxy)-1-ethyl]-1-methoxycarbonyl-3-indoleacetic Acid Methyl Ester

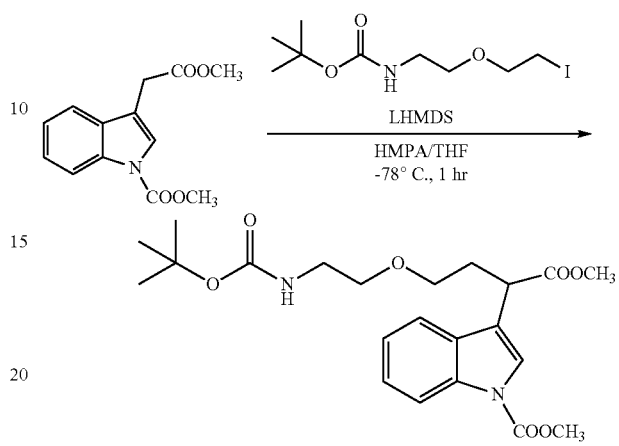

In a nitrogen atmosphere, 1-methoxycarbonyl-3-indoleacetic acid methyl ester (500 mg, 2.022 mmol) and hexamethylphosphoric triamide (HMPA, 1.81 g, 10.11 mmol) were dissolved in tetrahydrofuran (4 ml), and the solution was cooled to −78° C. A 1.5 M solution of lithium diisopropylamide (LDA) in cyclohexane (2.02 ml, 1.5 eq) was slowly added dropwise thereto, and the mixture was stirred at −78° C. for 0.5 hours. To this reaction solution, a tetrahydrofuran (2 ml) solution of 2-(N-tert-butoxycarbonyl-2-aminoethoxy)-1-iodoethane (637 mg, 2.022 mmol) was slowly added dropwise, and the mixture was stirred at −78° C. for 1 hour. After the reaction was confirmed by TLC to be complete, the temperature was adjusted to 0° C., and the reaction was quenched by the addition of water (15 ml), followed by extraction with ethyl acetate (15 ml) three times. The organic layer was washed twice with brine and dried over anhydrous sodium sulfate. The solvent was distilled off under reduced pressure, and then, the residue was purified by silica gel column chromatography (hexane: ethyl acetate=8:2) to obtain α-[2-(N-tert-butoxycarbonyl-2-aminoethoxy)-1-ethyl]-1-methoxycarbonyl-3-indoleacetic acid methyl ester (645 mg, yield: 79%): $^1$H NMR (400 MHz, CDCl$_3$): δ 8.18 (d, J=7.0 Hz, 1H), 7.63 (d, J=7.7 Hz, 1H), 7.57 (s, 1H), 7.34 (t, J=7.7 Hz, 1H), 7.26 (t, J=7.3 Hz, 1H), 4.98 (s, 1H), 4.02-4.06 (m, 4H), 3.69 (s, 3H), 3.43-3.51 (m, 4H), 3.30 (m, 2H), 2.29 (m, 2H), 1.45 (s, 3H); $^{13}$C NMR (100 MHz, CDCl$_3$): δ 173.8, 155.9, 151.2, 135.4, 124.8, 123.1, 122.9, 119.2, 118.8, 115.2, 79.1, 69.8, 68.3, 52.7, 52.1, 40.3, 39.3, 32.2, 28.3; FAB-MS: m/z [M+H]$^+$ 435.

α-[2-(N-tert-Butoxycarbonyl-2-aminoethoxy)-1-ethyl]-3-indoleacetic Acid (Compound #14)

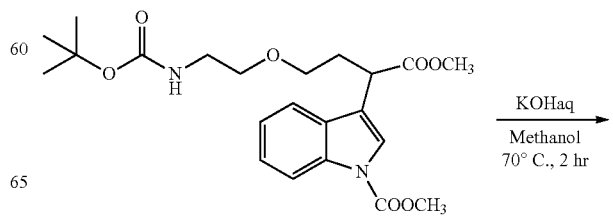

59

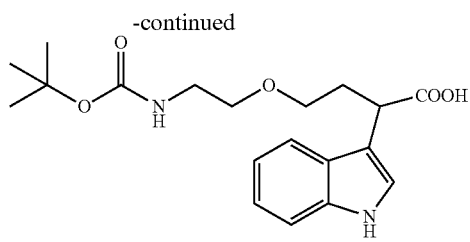

α-[2-(N-tert-Butoxycarbonyl-2-aminoethoxy)-1-ethyl]-1-methoxycarbonyl-3-indoleacetic acid methyl ester (80.0 mg, 0.184 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain α-[2-(N-tert-butoxycarbonyl-2-aminoethoxy)-1-ethyl]-3-indoleacetic acid (compound #14) (70.2 mg, yield: 87%); $^1$H NMR (400 MHz, CDCl$_3$): δ 8.40 (s, 1H), 7.67 (d, J=7.9 Hz, 1H), 7.29 (d, J=8.0 Hz, 1H), 7.15 (t, J=7.8 Hz, 1H), 7.08 (t, J=7.3 Hz, 1H), 7.04 (s, 1H), 5.03 (s, 1H), 4.04 (t, J=7.1 Hz, 1H), 3.30-3.46 (m, 4H), 3.23 (m, 2H), 2.26 (m, 2H), 1.44 (s, 9H); $^{13}$C NMR (100 MHz, CDCl$_3$): δ 179.2, 156.2, 136.2, 126.4, 122.6, 122.1, 119.5, 119.1, 112.6, 111.3, 79.4, 69.7, 68.5, 40.3, 39.7, 32.3, 28.4; IR (neat): 3406, 3332, 1699, 1520, 1458, 1367, 1252, 1169, 1119 cm$^{-1}$; FAB-MS: m/z [M+Na]$^+$ 385.

Synthesis of Compound #15

N-tert-Butoxycarbonyl-4-amino-1-butanol

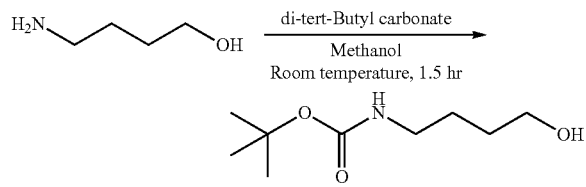

4-Amino-1-butanol (1.0 g, 11.22 mmol) was dissolved in methanol (10 ml). To this solution, di-tert-butyl carbonate (2.53 g, 11.58 mmol) was added, and the mixture was stirred at room temperature for 1.5 hours. After the reaction was confirmed by TLC to be complete, the solvent was distilled off under reduced pressure, and the residue was purified by silica gel column chromatography (hexane:acetone=9:1) to obtain N-tert-butoxycarbonyl-4-amino-1-butanol (1.88 g, yield: 89%).

60

N-tert-Butoxycarbonyl-4-amino-1-iodobutane

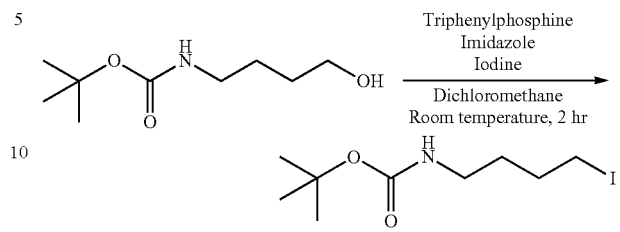

Triphenylphosphine (3.3 g, 12.58 mmol) and imidazole (0.86 g, 12.63 mmol) were dissolved in dichloromethane (15 ml), and the solution was stirred at 5 minutes. Then, iodine (3.2 g, 12.61 mmol) was added thereto, and the mixture was stirred for 10 minutes. A dichloromethane (4 ml) solution of N-tert-butoxycarbonyl-4-amino-1-butanol (1.6 g, 8.454 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane:ethyl acetate=9:1) to obtain N-tert-butoxycarbonyl-4-amino-1-iodobutane (1.83 g, yield: 72%).

α-(N-tert-Butoxycarbonyl-4-amino-1-butyl)-1-methoxycarbonyl-3-indoleacetic Acid Methyl Ester

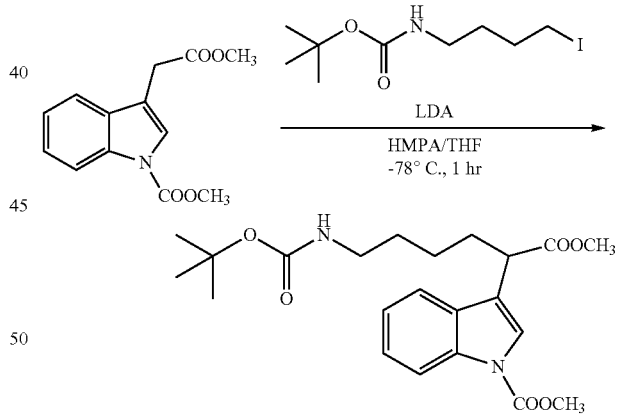

In a nitrogen atmosphere, 1-methoxycarbonyl-3-indoleacetic acid methyl ester (400 mg, 1.618 mmol) and hexamethylphosphoric triamide (HMPA, 1.45 g, 8.086 mmol) were dissolved in tetrahydrofuran (4 ml), and the solution was cooled to −78° C. A 1.5 M solution of lithium diisopropylamide (LDA) in cyclohexane (1.62 ml, 1.5 eq) was slowly added dropwise thereto, and the mixture was stirred at −78° C. for 0.5 hours. To this reaction solution, a tetrahydrofuran (2 ml) solution of N-tert-butoxycarbonyl-4-amino-1-iodobutane (484 mg, 1.618 mmol) was slowly added dropwise, and the mixture was stirred at −78° C. for 1 hour. After the reaction was confirmed by TLC to be complete, the temperature was adjusted to 0° C., and the reaction was quenched by the addition of water (15 ml), followed by extraction with ethyl acetate (15 ml) three times. The organic layer was washed twice with brine and dried over anhydrous sodium sulfate. The solvent was distilled off under reduced pressure, and then, the residue was purified by silica gel column chromatography (hexane: ethyl acetate=8:2) to obtain α-(N-tert-butoxycarbonyl-4-amino-1-butyl)-1-methoxycarbonyl-3-indoleacetic acid methyl ester (373 mg, yield: 55%): $^1$H NMR (400 MHz, CDCl$_3$): δ 8.18 (d, J=7.8 Hz, 1H), 7.60 (d, J=7.8 Hz, 1H), 7.55 (s, 1H), 7.34 (t, J=7.9 Hz, 1H), 7.25 (t, J=7.7 Hz, 1H), 4.59 (s, 1H), 4.02 (s, 3H), 3.80 (t, J=7.6 Hz, 1H), 3.67 (s, 3H), 3.09 (m, 2H), 2.03 (m, 2H), 1.25-1.53 (m, 13H); $^{13}$C NMR (100 MHz, CDCl$_3$): δ 173.9, 155.9, 151.2, 135.5, 129.3, 124.8, 123.0, 122.9, 119.2, 115.2, 78.9, 53.6, 52.0, 42.5, 40.2, 31.7, 29.8, 28.3, 24.8; FAB-MS: m/z [M+H]$^+$ 419.

α-(N-tert-Butoxycarbonyl-4-amino-1-butyl)-3-indoleacetic Acid (Compound #15)

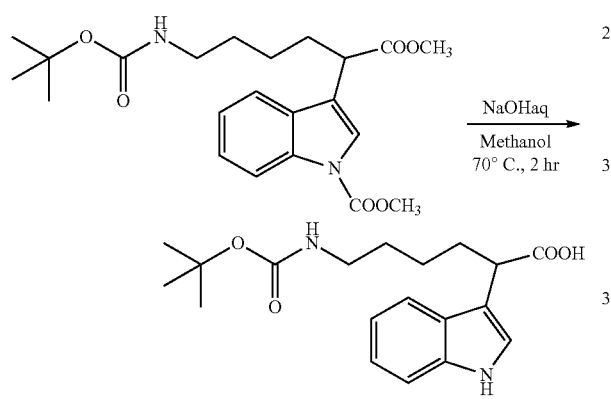

α-(N-tert-Butoxycarbonyl-4-amino-1-butyl)-1-methoxycarbonyl-3-indoleacetic acid methyl ester (100 mg, 0.239 mmol) was dissolved in methanol (2 ml). To this solution, a 2 N aqueous sodium hydroxide solution (0.5 ml) was added, and the mixture was stirred at 70° C. for 2 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-(N-tert-butoxycarbonyl-4-amino-1-butyl)-3-indoleacetic acid (compound #15) (71.8 mg, yield: 87%): $^1$H NMR (400 MHz, CDCl$_3$): δ 8.35 (s, 1H), 7.67 (d, J=7.8 Hz, 1H), 7.28 (d, J=7.8 Hz, 1H), 7.15 (t, J=7.7 Hz, 1H), 7.09 (t, J=7.3 Hz, 1H), 7.00 (s, 1H), 4.57 (s, 1H), 3.81 (t, J=7.5 Hz, 1H), 3.02 (m, 2H), 1.97 (m, 2H), 1.23-1.48 (m, 13H); C NMR (100 MHz, CDCl$_3$): δ 179.6, 156.1, 136.1, 126.4, 122.3, 122.0, 119.4, 119.1, 113.0, 111.3, 79.3, 42.9, 40.3, 31.9, 29.7, 28.4, 24.7; IR (neat): 3747, 1699, 1520, 1456, 1367, 1250, 1170 cm$^{-1}$; FAB-MS: m/z [M+H]$^+$ 347.

Synthesis of Compound #17

2-Ethyl-1-iodobutane

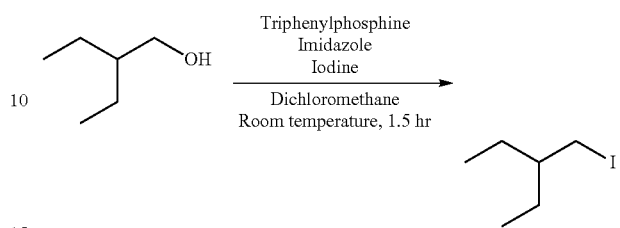

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 2-ethyl-1-butanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane) to obtain 2-ethyl-1-iodobutane (0.35 g, yield: 34%).

α-(2-Ethyl-1-butyl)-1-methoxycarbonyl-3-indoleacetic Acid Methyl Ester

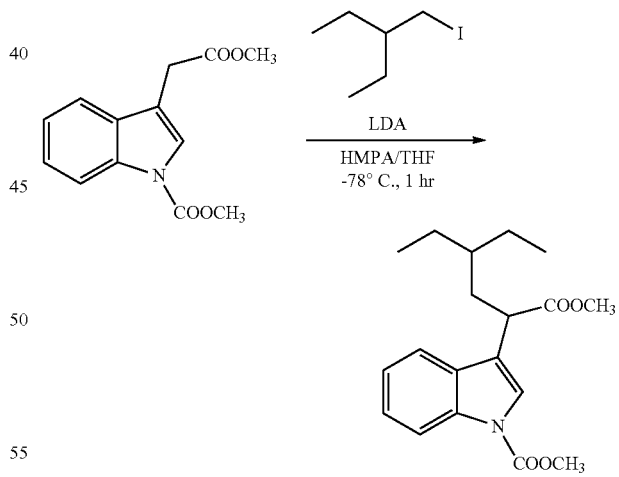

In a nitrogen atmosphere, 1-methoxycarbonyl-3-indoleacetic acid methyl ester (100 mg, 0.404 mmol) and hexamethylphosphoric triamide (HMPA, 362 mg, 2.020 mmol) were dissolved in tetrahydrofuran (2 ml), and the solution was cooled to −78° C. A 1.0 M solution of lithium bis(trimethylsilyl)amide (LHMDS) in tetrahydrofuran (0.61 ml, 1.5 eq) was slowly added dropwise thereto, and the mixture was stirred at −78° C. for 0.5 hours. To this reaction solution, a tetrahydrofuran (1 ml) solution of 2-ethyl-1-iodobutane (85.8 mg, 0.405 mmol) was slowly added dropwise, and the mixture was stirred at −78° C. for 1 hour. After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=9:1) to obtain α-(2-ethyl-1-butyl)-1-methoxycarbonyl-3-indoleacetic acid methyl ester (104 mg, yield: 78%): $^1$H NMR (400 MHz, CDCl$_3$): δ 8.18 (d, J=7.0 Hz, 1H), 7.64 (d, J=7.8 Hz, 1H), 7.57 (s, 1H), 7.34 (t, J=7.7 Hz, 1H), 7.26 (t, J=7.4 Hz, 1H), 4.01 (s, 3H), 3.93 (t, J=7.8 Hz, 1H), 3.67 (s, 3H), 1.96 (m, 2H), 1.21-1.41 (m, 5H), 0.82-0.88 (m, 6H); $^{13}$C NMR (100 MHz, CDCl$_3$): δ 174.3, 151.3, 135.5, 129.5, 124.7, 122.9, 119.7, 119.3, 115.2, 53.7, 52.0, 40.4, 38.0, 35.6, 25.1, 24.9, 10.4, 10.4; IR (neat): 1738, 1455, 1377, 1256, 1164, 1085 cm$^{-1}$; FAB-MS: m/z [M]$^+$ 331.

α-(2-Ethyl-1-butyl)-3-indoleacetic Acid (Compound #17)

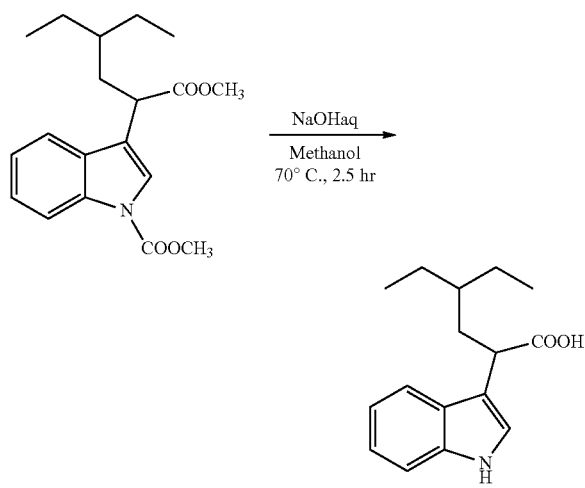

α-(2-Ethyl-1-butyl)-1-methoxycarbonyl-3-indoleacetic acid (70.0 mg, 0.211 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-(2-ethyl-1-butyl)-3-indoleacetic acid (compound #17) (52.4 mg, yield: 96): $^1$H NMR (400 MHz, CDCl$_3$): δ 8.02 (s, 1H), 7.70 (d, J=7.9 Hz, 1H), 7.30 (d, J=8.0 Hz, 1H), 7.17 (t, J=7.9 Hz, 1H), 7.11 (t, J=7.5 Hz, 1H), 7.08 (s, 1H), 3.97 (t, J=7.8 Hz, 1H), 1.96 (m, 2H), 1.23-1.39 (m, 5H), 0.78-0.84 (m, 6H); $^{13}$C NMR (100 MHz, CDCl$_3$): δ 181.1, 136.1, 126.6, 122.2, 122.2, 119.7, 119.3, 113.7, 111.2, 40.6, 37.8, 35.9, 25.0, 25.0, 10.4, 10.4; IR (neat): 3414, 1703, 1458, 1293, 1098 cm$^{-1}$; FAB-MS: m/z [M+H]$^+$ 260.

Synthesis of Compound #18

3-Methyl-1-iodopentane

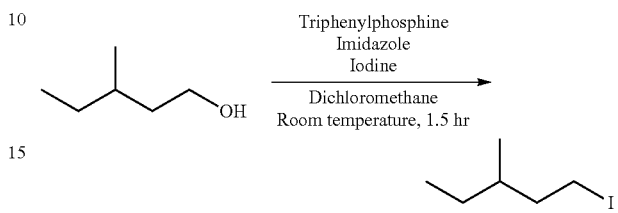

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 3-methyl-1-pentanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane:ethyl acetate=98:2) to obtain 3-methyl-1-iodopentane (0.12 mg, yield: 11%).

α-(3-Methyl-1-pentyl)-1-methoxycarbonyl-3-indoleacetic Acid Methyl Ester

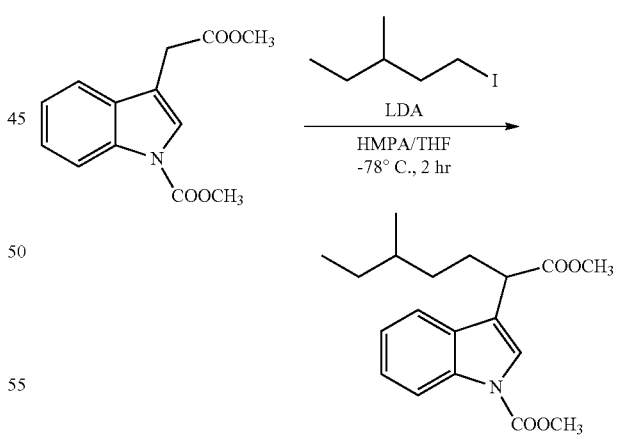

In a nitrogen atmosphere, 1-methoxycarbonyl-3-indoleacetic acid methyl ester (50.0 mg, 0.202 mmol) and hexamethylphosphoric triamide (HMPA, 181 mg, 1.011 mmol) were dissolved in tetrahydrofuran (1 ml), and the solution was cooled to −78° C. A 1.0 M solution of lithium bis(trimethylsilyl)amide (LHMDS) in tetrahydrofuran (0.30 ml, 1.5 eq) was slowly added dropwise thereto, and the mixture was stirred at −78° C. for 0.5 hours. To this reaction solution, a tetrahydrofuran (1 ml) solution of 3-methyl-1- iodopentane (51.5 mg, 0.243 mmol) was slowly added dropwise, and the mixture was stirred at −78° C. for 2 hours. After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=12:1) to obtain α-(3-methyl-1-pentyl)-1-methoxycarbonyl-3-indoleacetic acid methyl ester (25.8 mg, yield: 39%): $^1$H NMR (400 MHz, CDCl$_3$): δ 8.18 (d, J=6.7 Hz, 1H), 7.62 (d, J=7.7 Hz, 1H), 7.56 (s, 1H), 7.34 (t, J=7.8 Hz, 1H), 7.26 (t, J=7.2 Hz, 1H), 4.03 (s, 3H), 3.77 (t, J=7.9 Hz, 1H), 3.68 (s, 3H), 2.01 (m, 2H), 1.10-1.39 (m, 5H), 0.82-0.87 (m, 6H); $^{13}$C NMR (100 MHz, CDCl$_3$): δ 174.2, 151.3, 135.5, 129.5, 124.8, 122.9, 119.4, 119.3, 115.2, 53.7, 52.0, 42.9, 34.4, 34.2, 29.8, 29.2, 19.1, 11.3; IR (neat): 1741, 1454, 1378, 1254, 1084 cm$^{-1}$; FAB-MS: m/z [M]$^+$ 331.

α-(3-Methyl-1-pentyl)-3-indoleacetic Acid (Compound #18)

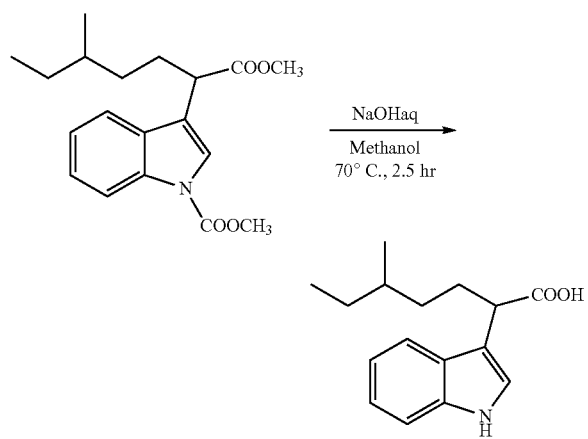

α-(3-Methyl-1-pentyl)-1-methoxycarbonyl-3-indoleacetic acid methyl ester (20.0 mg, 0.060 mmol) was dissolved in methanol (1 ml). To this solution, a 2 N aqueous sodium hydroxide solution (0.25 ml) was added, and the mixture was stirred at 70° C. for 2.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-(3-methyl-1-pentyl)-3-indoleacetic acid (compound #18) (16.8 mg, yield: 89%): $^1$H NMR (400 MHz, CDCl$_3$): δ 8.07 (s, 1H), 7.70 (d, J=7.8 Hz, 1H), 7.33 (d, J=8.1 Hz, 1H), 7.19 (t, J=8.0 Hz, 1H), 7.10-7.13 (m, 2H), 3.82 (t, J=6.7 Hz, 1H), 1.97 (m, 2H), 1.10-1.36 (m, 5H), 0.79-0.85 (m, 6H); $^{13}$C NMR (100 MHz, CDCl$_3$): δ 180.4, 136.1, 126.6, 122.2, 122.2, 119.7, 119.3, 113.7, 111.2, 43.2, 34.5, 34.3, 30.1, 29.2, 19.1, 11.3; IR (neat): 3418, 1704, 1456, 1294, 1098 cm$^{-1}$; FAB-MS: m/z [M]$^+$ 259.

Synthesis of Compound #19

2-Methyl-1-iodopentane

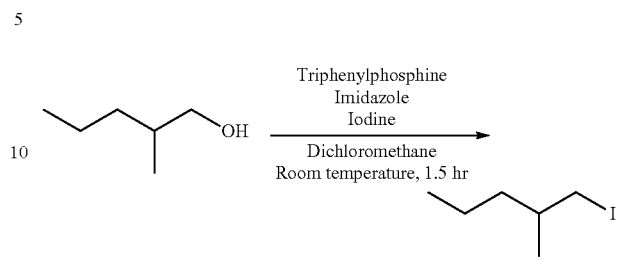

Triphenylphosphine (1.93 g, 7.358 mmol) and imidazole (0.5 g, 7.344 mmol) were dissolved in dichloromethane (5.0 ml), and the solution was stirred for 5 minutes. Then, iodine (1.86 g, 7.328 mmol) was added thereto, and the mixture was stirred for 10 minutes. A dichloromethane (2.0 ml) solution of 2-methyl-1-pentanol (0.5 g, 5.672 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane) to obtain 2-methyl-1-iodopentane (0.56 g, yield: 54%).

α-(2-Methyl-1-pentyl)-1-methoxycarbonyl-3-indoleacetic Acid Methyl Ester

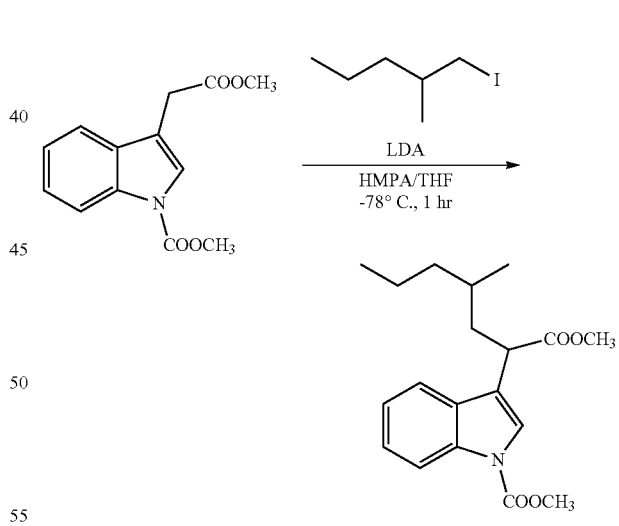

In a nitrogen atmosphere, 1-methoxycarbonyl-3-indoleacetic acid methyl ester (100 mg, 0.404 mmol) and hexamethylphosphoric triamide (HMPA, 362 mg, 2.020 mmol) were dissolved in tetrahydrofuran (2 ml), and the solution was cooled to −78° C. A 1.0 M solution of lithium bis(trimethylsilyl)amide (LHMDS) in tetrahydrofuran (0.61 ml, 1.5 eq) was slowly added dropwise thereto, and the mixture was stirred at −78° C. for 0.5 hours. To this reaction solution, a tetrahydrofuran (1 ml) solution of 2-methyl-1-iodopentane (85.8 mg, 0.405 mmol) was slowly added dropwise, and the mixture was stirred at −78° C. for 1 hour.

After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=9:1) to obtain α-(2-methyl-1-pentyl)-1-methoxycarbonyl-3-indoleacetic acid methyl ester (101 mg, yield: 75%): $^1$H NMR (400 MHz, CDCl$_3$): δ 8.18 (d, J=5.7 Hz, 1H), 7.63 (d, J=7.8 Hz, 1H), 7.55 (s, 1H), 7.34 (t, J=7.6 Hz, 1H), 7.27 (t, J=7.5 Hz, 1H), 4.03 (s, 3H), 3.91-3.97 (m, 1H), 3.68 (s, 3H), 1.58-2.24 (m, 2H), 1.10-1.50 (m, 5H), 0.83-0.97 (m, 6H); $^{13}$C NMR (100 MHz, CDCl$_3$): δ 174.4, 151.2, 135.4, 129.4, 124.7, 122.9, 122.8, 119.9, 119.4, 115.2, 53.7, 52.0, 40.4, 39.6, 39.3, 30.7, 19.8, 19.4, 14.2; IR (neat): 1739, 1456, 1373, 1217, 1087 cm$^{-1}$; FAB-MS: m/z [M]$^+$ 331.

α-(2-Methyl-1-pentyl)-3-indoleacetic Acid (Compound #19)

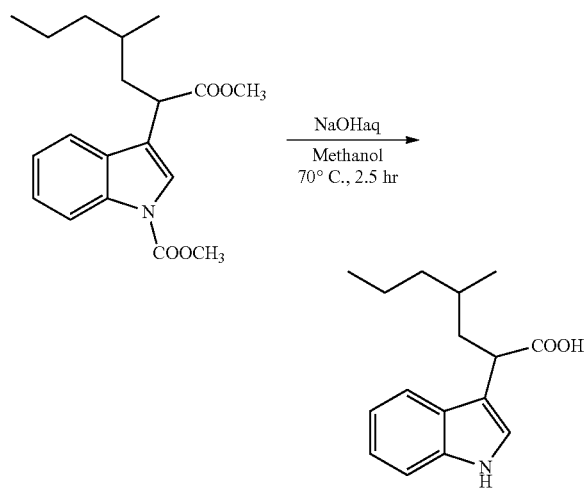

α-(2-Methyl-1-pentyl)-1-methoxycarbonyl-3-indoleacetic acid methyl ester (70.0 mg, 0.211 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-(2-methyl-1-pentyl)-3-indoleacetic acid (compound #19) (51.9 mg, yield: 95%): $^1$H NMR (400 MHz, CDCl$_3$): δ 8.12 (s, 1H), 7.70 (d, J=7.8 Hz, 1H), 7.30 (d, J=8.0 Hz, 1H), 7.17 (t, J=7.4 Hz, 1H), 7.11 (t, J=7.2 Hz, 1H), 7.06 (s, 1H), 3.96-4.02 (m, 1H), 1.60-2.22 (m, 2H), 1.12-1.51 (m, 5H), 0.79-0.94 (m, 6H); $^{13}$C NMR (100 MHz, CDCl$_3$): δ 180.9, 136.1, 126.5, 122.3, 122.2, 119.7, 119.3, 113.3, 111.2, 40.7, 39.9, 39.2, 30.3, 19.8, 19.4, 14.3; IR (neat): 3417, 1699, 1457, 1292, 1099 cm$^{-1}$; FAB-MS: m/z [M]$^+$ 259.

Synthesis of Compound #20

4-Phenyl-2-(1H-indol-3-yl)-4-oxo-butanoic Acid (Compound #20)

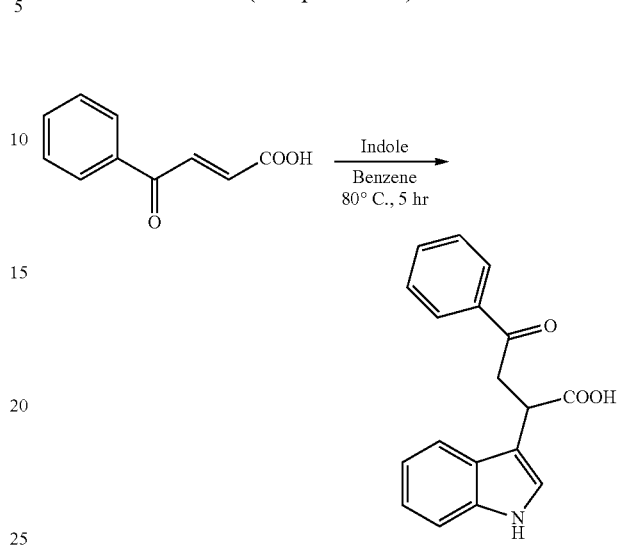

In a 30-mL round-bottomed flask, trans-4-phenyl-4-oxo-2-butenoic acid (1.0 g, 5.65 mmol) was dissolved in benzene (25 mL). To the solution, indole (0.79 g, 6.77 mmol) was added, and the mixture was stirred at 80° C. for 5 hours and stirred until the temperature became room temperature. The solvent in the reaction solution was distilled off under reduced pressure, and the residue was recrystallized from benzene to obtain 4-phenyl-2-(1H-indol-3-yl)-4-oxo-butanoic acid (compound #20) (1.24 g, yield: 75%); Melting point: 149 to 150° C.; $^1$H NMR (400 MHz, acetone-d$_6$): δ 10.17 (1H, brs, 1H), 8.05 (2H, d, J=8.2 Hz), 7.80 (1H, d, J=8.3 Hz), 7.57 (1H, t, J=7.8 Hz), 7.51 (2H, dd, J=8.2, 7.8 Hz), 7.41 (1H, d, J=8.2 Hz), 7.37 (1H, s), 7.13 (1H, t, J=8.2 Hz), 7.06 (1H, t, J=8.2 Hz), 4.57 (1H, dd, J=11.0, 4.1 Hz), 4.13 (1H, dd, J=17.8, 11.0 Hz), 3.41 (1H, dd, J=17.8, 4.1 Hz);

IR: (neat): 3400, 3055, 1711, 1677, 1453 cm$^{-1}$; FAB-MS m/z [M+H]$^+$ calcd for 294.1130 (C$_{18}$H$_{16}$NO$_3$), found 294.1143 [M+H]$^+$.

Synthesis of Compound #21

4,4,5,5,5-Pentafluoro-1-iodopentane

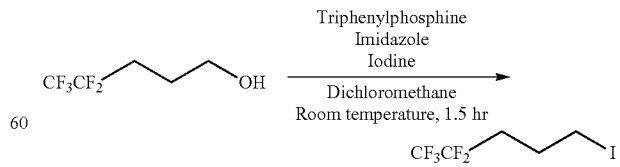

Triphenylphosphine (1.1 g, 4.211 mmol) and imidazole (0.29 g, 4.211 mmol) were dissolved in dichloromethane (5.0 ml), and the solution was stirred for 5 minutes. Then, iodine (1.07 g, 4.211 mmol) was added thereto, and the mixture was stirred for 10 minutes. A dichloromethane (2.0 ml) solution of 4,4,5,5,5-pentafluoro-1-pentanol (0.5 g, 2.807 mmol) was added dropwise thereto, and the mixture was stirred at room temperature for 1.5 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane) to obtain 4,4,5,5,5-pentafluoro-1-iodopentane (0.36 g, yield: 45%).

α-(4,4,5,5,5-Pentafluoro-1-pentyl)-1-methoxycarbonyl-3-indoleacetic Acid Methyl Ester

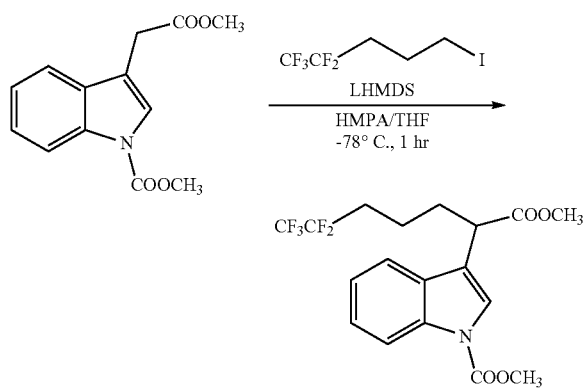

In a nitrogen atmosphere, 1-methoxycarbonyl-3-indoleacetic acid methyl ester (50.0 mg, 0.202 mmol) and hexamethylphosphoric triamide (HMPA, 181 mg, 1.011 mmol) were dissolved in tetrahydrofuran (1 ml), and the solution was cooled to −78° C. A 1.0 M solution of lithium bis(trimethylsilyl)amide (LHMDS) in tetrahydrofuran (0.30 ml, 1.5 eq) was slowly added dropwise thereto, and the mixture was stirred at −78° C. for 0.5 hours. To this reaction solution, a tetrahydrofuran (1 ml) solution of 4,4,5,5,5-pentafluoro-1-iodopentane (81.4 mg, 0.283 mmol) was slowly added dropwise, and the mixture was stirred at −78° C. for 1 hour. After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=85:15) to obtain α-(4,4,5,5,5-pentafluoro-1-pentyl)-1-methoxycarbonyl-3-indoleacetic acid methyl ester (59.8 mg, yield: 73%): $^1$H NMR (400 MHz, CDCl$_3$): δ 8.19 (d, J=7.6 Hz, 1H), 7.60 (d, J=7.8 Hz, 1H), 7.57 (s, 1H), 7.36 (t, J=7.5 Hz, 1H), 7.27 (t, J=6.9 Hz, 1H), 4.03 (s, 3H), 3.83 (t, J=7.6 Hz, 1H), 3.69 (s, 3H), 1.98-2.23 (m, 4H), 1.62-1.68 (m, 2H); $^{13}$C NMR (100 MHz, CDCl$_3$): δ 173.5, 151.3, 135.5, 129.1, 125.0, 123.1, 123.1, 119.2, 118.6, 115.3, 53.8, 52.2, 42.3, 31.4, 30.6, 30.3, 30.1, 18.6; IR (neat): 1739, 1456, 1378, 1257, 1198 cm$^{-1}$; FAB-MS: m/z [M]$^+$ 407.

α-(4,4,5,5,5-Pentafluoro-1-pentyl)-3-indoleacetic Acid (Compound #21)

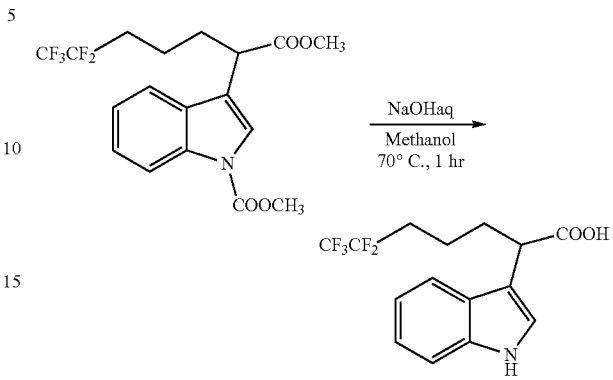

α-(4,4,5,5,5-Pentafluoro-1-pentyl)-1-methoxycarbonyl-3-indoleacetic acid methyl ester (55.5 mg, 0.183 mmol) was dissolved in methanol (1 ml). To this solution, a 2 N aqueous sodium hydroxide solution (0.25 ml) was added, and the mixture was stirred at 70° C. for 1 hour. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-(4,4,5,5,5-pentafluoro-1-pentyl)-3-indoleacetic acid (compound #21) (43.9 mg, yield: 97%): $^1$H NMR (400 MHz, CDCl$_3$): δ 8.06 (s, 1H), 7.67 (d, J=7.9 Hz, 1H), 7.33 (d, J=8.1 Hz, 1H), 7.20 (t, J=8.0 Hz, 1H), 7.12 (t, J=7.9 Hz, 1H), 7.09 (s, 1H), 3.87 (t, J=7.5 Hz, 1H), 1.95-2.22 (m, 4H), 1.60-1.67 (m, 2H); $^{13}$C NMR (100 MHz, CDCl$_3$): δ 179.9, 136.2, 126.2, 122.4, 122.4, 119.9, 119.1, 112.5, 111.4, 42.7, 31.5, 30.6, 30.3, 30.1, 18.6; IR (neat): 3418, 1704, 1459, 1198 cm$^{-1}$; FAB-MS: m/z [M]$^+$ 335.

Synthesis of Compound #22

3-(2-Hydroxy-1-ethyl)-1,1'-biphenyl

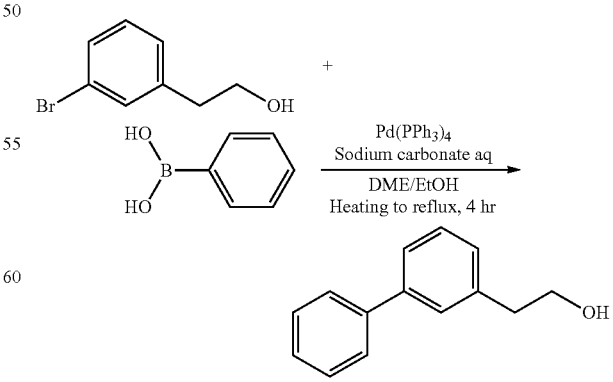

2-(3-Bromophenyl)-1-ethanol (200 mg, 0.995 mmol) was dissolved in a mixed solvent of dimethoxyethane:ethanol (=5:1) (3.0 ml). To the solution, phenylboronic acid (242 mg, 1.985 mmol), a 2 M aqueous sodium carbonate solution (1.5 ml), and tetrakis(triphenylphosphine) palladium(0) (Pd(PPh$_3$)$_4$, 56.0 mg, 0.048 mmol) were added, and the mixture was stirred for 4 hours under heating to reflux. After the reaction was confirmed by TLC to be complete, the reaction solution was filtered through celite, and the filtrate was neutralized by the addition of hydrochloric acid, followed by extraction with ethyl acetate (10 ml) three times. The organic layer was washed twice with brine and dried over anhydrous sodium sulfate. The solvent was distilled off under reduced pressure, and then, the residue was purified by silica gel column chromatography (hexane:ethyl acetate=8:2) to obtain 3-(2-hydroxy-1-ethyl)-1,1'-biphenyl (172 mg, yield: 87%).

3-(2-Iodo-1-ethyl)-1,1'-biphenyl

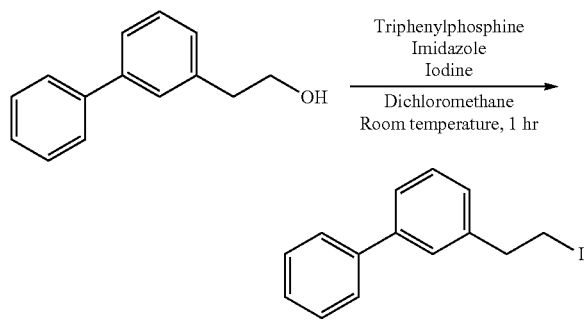

Triphenylphosphine (327 mg, 1.248 mmol) and imidazole (85.0 mg, 1.249 mmol) were dissolved in dichloromethane (3.0 ml), and the solution was stirred for 5 minutes. Then, iodine (317 mg, 1.248 mmol) was added thereto, and the mixture was stirred for 10 minutes. A dichloromethane (0.5 ml) solution of 3-(2-hydroxy-1-ethyl)-1,1'-biphenyl (165 mg, 0.832 mmol) was added dropwise thereto, and the mixture was stirred at room temperature for 1 hour. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane:ethyl acetate=98:2) to obtain 3-(2-iodo-1-ethyl)-1,1'-biphenyl (185 mg, yield: 72%).

α-[2-(1,1'-Biphenyl-3-yl)-1-ethyl]-1-methoxycarbonyl-3-indoleacetic Acid Methyl Ester

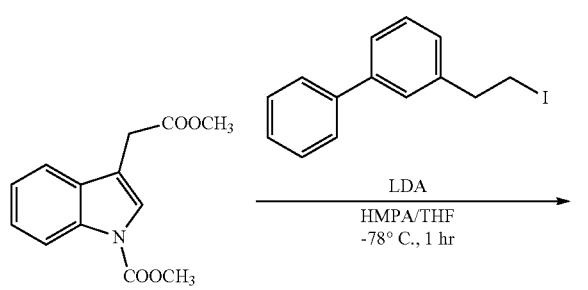

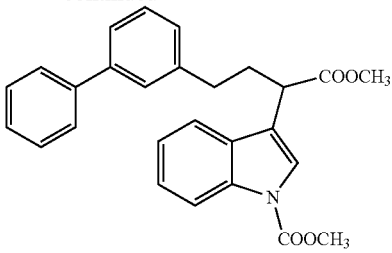

In a nitrogen atmosphere, 1-methoxycarbonyl-3-indoleacetic acid methyl ester (80 mg, 0.324 mmol) and hexamethylphosphoric triamide (HMPA, 290 mg, 1.618 mmol) were dissolved in tetrahydrofuran (2 ml), and the solution was cooled to −78° C. A 1.5 M solution of lithium diisopropylamide (LDA) in cyclohexane (0.32 ml, 1.5 eq) was slowly added dropwise thereto, and the mixture was stirred at −78° C. for 0.5 hours. To this reaction solution, a tetrahydrofuran (1 ml) solution of 3-(2-iodo-1-ethyl)-1,1'-biphenyl (99.7 mg, 0.324 mmol) was slowly added dropwise, and the mixture was stirred at −78° C. for 1 hour. After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=85:15) to obtain α-[2-(1,1'-biphenyl-3-yl)-1-ethyl]-1-methoxycarbonyl-3-indoleacetic acid methyl ester (132 mg, yield: 96%): $^1$H NMR (400 MHz, CDCl$_3$): δ 8.19 (d, J=6.8 Hz, 1H), 7.55-7.58 (m, 4H), 7.31-7.44 (m, 7H), 7.24 (t, J=8.1 Hz, 1H), 7.15 (d, J=7.5 Hz, 1H), 4.02 (s, 3H), 3.86 (t, J=7.5 Hz, 1H), 3.65 (S, 3H), 2.73 (t, J=7.7 Hz, 2H), 2.25-2.58 (m, 2H); $^{13}$C NMR (100 MHz, CDCl$_3$): δ 173.8, 151.2, 141.4, 141.3, 141.1, 135.5, 129.3, 128.8, 128.6, 127.3, 127.2, 127.1, 124.9, 124.8, 123.1, 122.9, 119.3, 118.9, 115.2, 53.7, 52.1, 41.8, 33.7, 33.5; FAB-MS: m/z [M]$^+$ 427.

α-[2-(1,1'-Biphenyl-3-yl)-1-ethyl]-3-indoleacetic Acid (Compound #22)

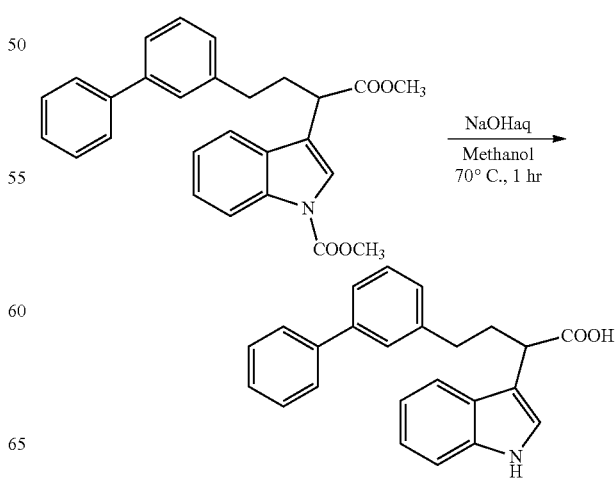

α-[2-(1,1'-Biphenyl-3-yl)-1-ethyl]-1-methoxycarbonyl-3-indoleacetic acid methyl ester (80.0 mg, 0.187 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-[2-(1,1'-biphenyl-3-yl)-1-ethyl]-3-indoleacetic acid (compound #22) (60.3 mg, yield: 91%): $^1$H NMR (400 MHz, CDCl$_3$): δ 8.01 (s, 1H), 7.65 (d, J=7.9 Hz, 1H), 7.53-7.55 (m, 2H), 7.29-7.41 (m, 7H), 7.17 (t, J=7.2 Hz, 1H), 7.07-7.13 (m, 3H), 3.91 (t, J=7.5 Hz, 1H), 2.71 (t, J=7.7 Hz, 2H), 2.39 (m, 2H); $^{13}$C NMR (100 MHz, CDCl$_3$): δ 180.3, 141.8, 141.3, 141.2, 136.1, 128.8, 128.7, 127.4, 127.4, 127.2, 126.4, 124.9, 122.4, 122.3, 119.8, 119.3, 112.9, 111.3, 42.2, 33.8, 33.7; IR (neat): 3420, 1699, 1456, 1216, 1097 cm$^{-1}$; FAB-MS: m/z [M] 355.

Synthesis of Compound #23

α-(2-Phenyl-1-ethyl)-1-methoxycarbonyl-3-indoleacetic Acid Methyl Ester

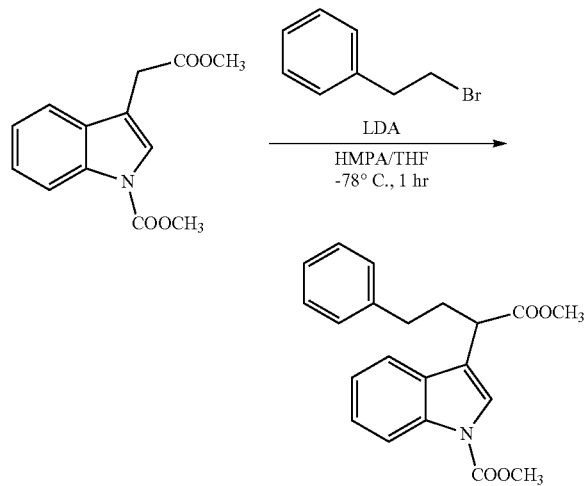

In a nitrogen atmosphere, 1-methoxycarbonyl-3-indoleacetic acid methyl ester (300 mg, 1.213 mmol) and hexamethylphosphoric triamide (HMPA, 1.09 g, 6.067 mmol) were dissolved in tetrahydrofuran (2 ml), and the solution was cooled to −78° C. A 1.5 M solution of lithium diisopropylamide (LDA) in cyclohexane (1.21 ml, 1.5 eq) was slowly added dropwise thereto, and the mixture was stirred at −78° C. for 0.5 hours. To this reaction solution, a tetrahydrofuran (2 ml) solution of 1-bromo-2-phenylethane (292 mg, 1.577 mmol) was slowly added dropwise, and the mixture was stirred at −78° C. for 1 hour. After the reaction was confirmed by TLC to be complete, the temperature was adjusted to 0° C., and the reaction was quenched by the addition of water (10 ml), followed by extraction with ethyl acetate (10 ml) three times. The organic layer was washed twice with brine and dried over anhydrous sodium sulfate. The solvent was distilled off under reduced pressure, and then, the residue was purified by silica gel column chromatography (benzene) to obtain α-(2-phenyl-1-ethyl)-1-methoxycarbonyl-3-indoleacetic acid methyl ester (228 mg, yield: 54%): $^1$H NMR (400 MHz, CDCl$_3$): δ 8.18 (d, J=6.0 Hz, 1H), 7.57 (s, 1H), 7.55 (d, J=8.0 Hz, 1H), 7.31 (t, J=7.8 Hz, 1H), 7.13-7.26 (m, 6H), 3.94 (s, 3H), 3.83 (t, J=7.5 Hz, 1H), 3.64 (s, 3H), 2.66 (t, J=7.8 Hz, 2H), 2.35 (m, 2H); $^{13}$C NMR (100 MHz, CDCl$_3$): δ 173.8, 151.2, 140.9, 135.4, 129.3, 128.4, 128.3, 126.0, 124.8, 123.1, 122.9, 119.3, 119.0, 115.2, 53.7, 52.0, 41.8, 33.5; FAB-MS: m/z [M]$^+$ 351.

α-(2-Phenyl-1-ethyl)-3-indoleacetic Acid (Compound #23)

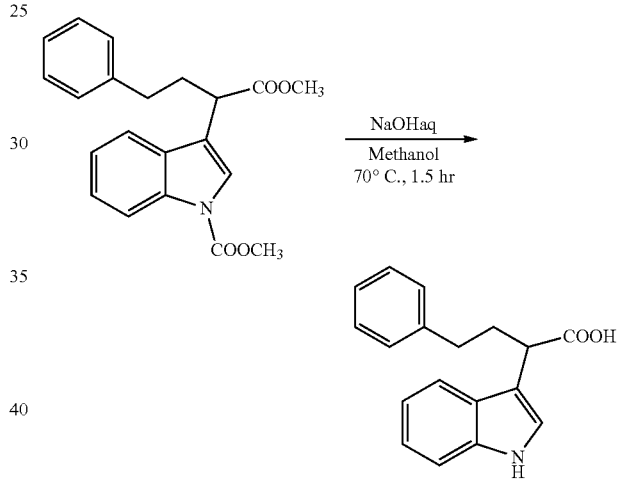

α-(2-Phenyl-1-ethyl)-1-methoxycarbonyl-3-indoleacetic acid methyl ester (150 mg, 0.427 mmol) was dissolved in methanol (2 ml). To this solution, a 2 N aqueous sodium hydroxide solution (0.5 ml) was added, and the mixture was stirred at 70° C. for 1.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-(2-phenyl-1-ethyl)-3-indoleacetic acid (compound #23) (85.3 mg, yield: 72%): $^1$H NMR (400 MHz, acetone-d$_6$): δ 10.16 (s, 1H), 7.67 (d, J=8.0 Hz, 1H), 7.40 (d, J=8.1 Hz, 1H), 7.09-7.32 (m, 7H), 7.03 (t, J=7.6 Hz, 1H), 3.93 (t, J=7.4 Hz, 1H), 2.67 (t, J=5.4 Hz, 2H), 2.35 (m, 2H); $^{13}$C NMR (100 MHz, acetone-d$_6$): δ 175.4, 142.4, 137.2, 128.8, 128.7, 127.2, 126.2, 123.2, 121.8, 119.4, 119.2, 113.6, 111.8, 42.5, 34.9, 34.1; IR (neat): 3416, 1700, 1457, 1246, 1098 cm$^{-1}$; FAB-MS: m/z [M]$^+$ 279.

Synthesis of Compound #24

2-Cyclopentyl-1-iodoethane

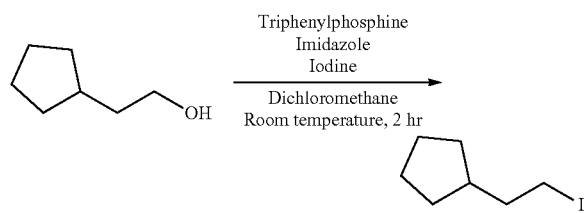

Triphenylphosphine (1.03 g, 3.942 mmol) and imidazole (0.27 g, 3.937 mmol) were dissolved in dichloromethane (5 ml), and the solution was stirred for 5 minutes. Then, iodine (1.0 g, 3.940 mmol) was added thereto, and the mixture was stirred for 10 minutes. A dichloromethane (1 ml) solution of 2-cyclopentyl-1-ethanol (0.3 g, 2.627 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane) to obtain 2-cyclopentyl-1-iodoethane (0.46 g, yield: 84%).

α-(2-Cyclopentyl-1-ethyl)-1-methoxycarbonyl-3-indoleacetic Acid Methyl Ester

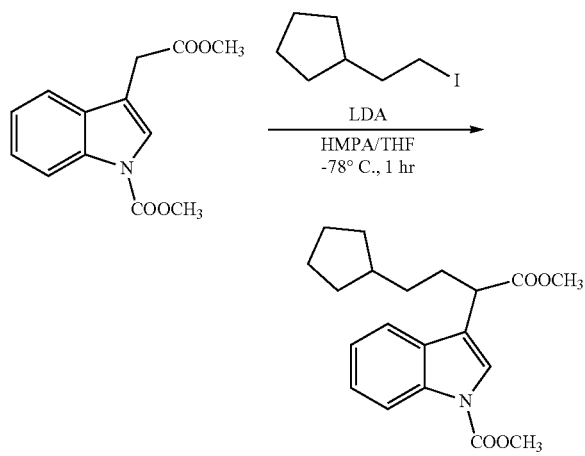

In a nitrogen atmosphere, 1-methoxycarbonyl-3-indoleacetic acid methyl ester (150 mg, 0.607 mmol) and hexamethylphosphoric triamide (HMPA, 544 mg, 3.036 mmol) were dissolved in tetrahydrofuran (2 ml), and the solution was cooled to −78° C. A 1.5 M solution of lithium diisopropylamide (LDA) in cyclohexane (0.61 ml, 1.5 eq) was slowly added dropwise thereto, and the mixture was stirred at −78° C. for 0.5 hours. To this reaction solution, a tetrahydrofuran (1 ml) solution of 2-cyclopentyl-1-iodoethane (153 mg, 0.728 mmol) was slowly added dropwise, and the mixture was stirred at −78° C. for 1 hour. After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate 13:1) to obtain α-(2-cyclopentyl-1-ethyl)-1-methoxycarbonyl-3-indoleacetic acid methyl ester (153 mg, yield: 76%): $^1$H NMR (400 MHz, CDCl$_3$): δ 8.18 (d, J=6.0 Hz, 1H), 7.63 (d, J=7.8 Hz, 1H), 7.57 (s, 1H), 7.32 (t, J=7.4 Hz, 1H), 7.25 (t, J=7.4 Hz, 1H), 3.99 (s, 3H), 3.88 (t, J=7.7 Hz, 1H), 3.67 (s, 3H), 2.05 (m, 2H), 1.76-1.79 (m, 3H), 1.59-1.62 (m, 2H), 1.47-1.50 (m, 2H), 1.12-1.17 (m, 2H); $^{13}$C NMR (100 MHz, CDCl$_3$): δ 174.1, 151.1, 135.4, 129.4, 124.6, 122.8, 119.4, 119.2, 115.1, 53.6, 51.9, 41.7, 38.5, 37.9, 32.5, 32.3, 24.9; FAB-MS: m/z [M]$^+$ 329.

α-(2-Cyclopentyl-1-ethyl)-1-methoxycarbonyl-3-indoleacetic Acid Methyl Ester (Compound #24)

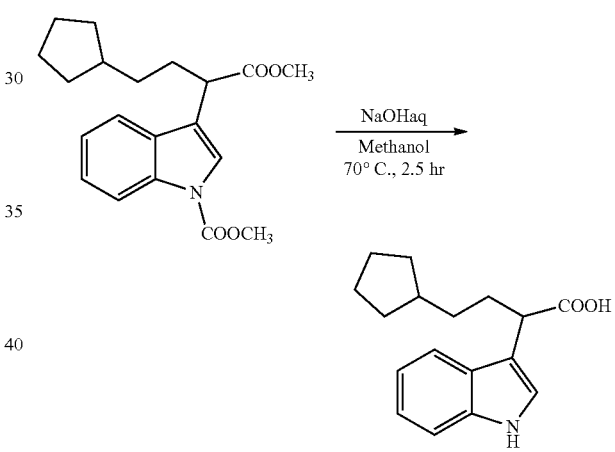

α-(2-Cyclopentyl-1-ethyl)-1-methoxycarbonyl-3-indoleacetic acid methyl ester (100 mg, 0.291 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=95:5) to obtain α-(2-cyclopentyl-1-ethyl)-1-methoxycarbonyl-3-indoleacetic acid methyl ester (compound #24) (78.5 mg, yield: 99%): $^1$H NMR (400 MHz, CDCl$_3$): δ 8.19 (s, 1H), 7.69 (d, J=7.9 Hz, 1H), 7.29 (d, J=8.0 Hz, 1H), 7.16 (t, J=8.0 Hz, 1H), 7.10 (t, J=7.5 Hz, 1H), 7.06 (s, 1H), 3.83 (t, J=7.6 Hz, 1H), 2.01 (m, 2H), 1.70-1.75 (m, 3H), 1.45-1.55 (m, 4H), 1.34-1.37 (m, 2H), 0.98-1.03 (m, 2H); $^{13}$C NMR (100 MHz, CDCl$_3$): δ 180.7, 136.1, 126.5, 122.2, 122.0, 119.5, 119.2, 113.4, 111.2, 43.1, 39.9, 34.1, 32.5, 31.6, 25.1; IR (neat): 3415, 1703, 1457, 1339, 1098 cm$^{-1}$; FAB-MS: m/z [M+Na]$^+$ 294.

Synthesis of Compound #25

Cyclopentyliodomethane

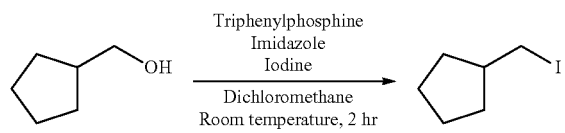 [SMILES: OCC1CCCC1 ; ICC1CCCC1]

Triphenylphosphine (1.18 g, 4.491 mmol) and imidazole (0.31 g, 4.495 mmol) were dissolved in dichloromethane (5 ml), and the solution was stirred for 5 minutes. Then, iodine (1.14 g, 4.492 mmol) was added thereto, and the mixture was stirred for 10 minutes. A dichloromethane (1 ml) solution of cyclopentylmethanol (0.3 g, 2.995 mmol) was added dropwise thereto, and the mixture was stirred at room temperature for 2 hours. After the reaction was confirmed by TLC to be complete, the reaction solution was filtered through celite, and a 5% aqueous sodium thiosulfate solution was added to the filtrate to remove iodine. The organic layer was washed twice with brine and dried over anhydrous sodium sulfate. The solvent was distilled off under reduced pressure, and then, the residue was purified by silica gel column chromatography (hexane) to obtain cyclopentyliodomethane (0.53 g, yield: 84%).

α-Cyclopentylmethyl-1-methoxycarbonyl-3-indoleacetic Acid Methyl Ester

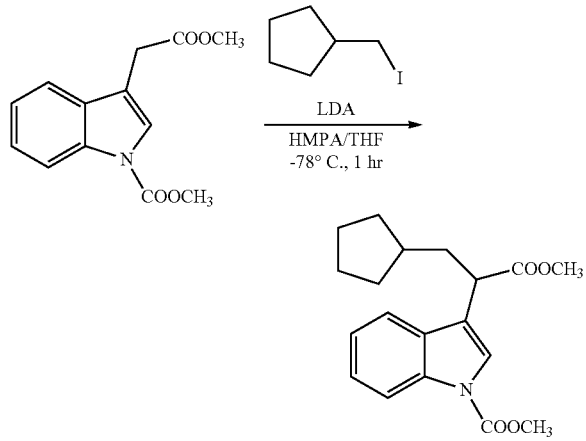

In a nitrogen atmosphere, 1-methoxycarbonyl-3-indoleacetic acid methyl ester (150 mg, 0.607 mmol) and hexamethylphosphoric triamide (HMPA, 544 mg, 3.036 mmol) were dissolved in tetrahydrofuran (2 ml), and the solution was cooled to −78° C. A 1.5 M solution of lithium diisopropylamide (LDA) in cyclohexane (0.61 ml, 1.5 eq) was slowly added dropwise thereto, and the mixture was stirred at −78° C. for 0.5 hours. To this reaction solution, a tetrahydrofuran (1 ml) solution of cyclopentyliodomethane (153 mg, 0.728 mmol) was slowly added dropwise, and the mixture was stirred at −78° C. for 1 hour. After the reaction was confirmed by TLC to be complete, the temperature was adjusted to 0° C., and the reaction was quenched by the addition of water (5 ml), followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=13:1) to obtain α-cyclopentylmethyl-1-methoxycarbonyl-3-indoleacetic acid methyl ester (153 mg, yield: 76%): $^1$H NMR (400 MHz, CDCl$_3$): δ 8.18 (d, J=6.0 Hz, 1H), 7.63 (d, J=7.8 Hz, 1H), 7.57 (s, 1H), 7.32 (t, J=7.4 Hz, 1H), 7.25 (t, J=7.4 Hz, 1H), 3.99 (s, 3H), 3.88 (t, J=7.7 Hz, 1H), 3.67 (s, 3H), 2.05 (m, 2H), 1.76-1.79 (m, 3H), 1.59-1.62 (m, 2H), 1.47-1.50 (m, 2H), 1.12-1.17 (m, 2H); $^{13}$C NMR (100 MHz, CDCl$_3$): δ 174.1, 151.1, 135.4, 129.4, 124.6, 122.8, 119.4, 119.2, 115.1, 53.6, 51.9, 41.7, 38.5, 37.9, 32.5, 32.3, 24.9; FAB-MS: m/z [M]$^+$ 329.

α-Cyclopentylmethyl-3-indoleacetic Acid (Compound #25)

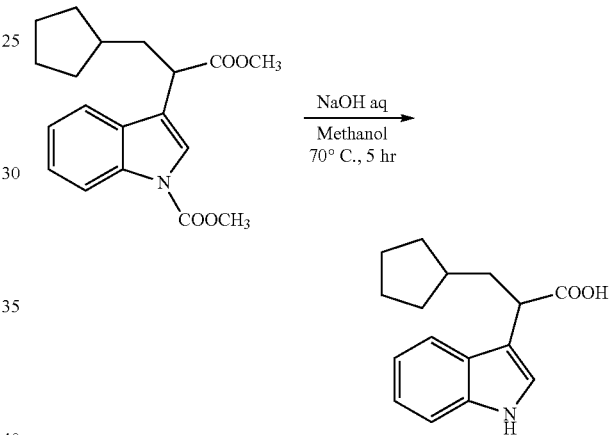

α-Cyclopentylmethyl-1-methoxycarbonyl-3-indoleacetic acid methyl ester (100 mg, 0.304 mmol) was dissolved in methanol (2 ml). To this solution, a 2 N aqueous sodium hydroxide solution (0.5 ml) was added, and the mixture was stirred at 70° C. for 2.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol 95:5) to obtain α-cyclopentylmethyl-3-indoleacetic acid (compound #25) (58.3 mg, yield: 75%); $^1$H NMR (400 MHz, acetone-d$_6$): δ 10.13 (s, 1H), 7.70 (d, J=7.8 Hz, 1H), 7.38 (d, J=8.1 Hz, 1H), 7.28 (s, 1H), 7.10 (t, J=8.0 Hz, 1H), 7.02 (t, J=7.1 Hz, 1H), 3.73 (t, J=7.7 Hz, 1H), 2.06 (m, 2H), 1.78-1.83 (m, 3H), 1.47-1.61 (m, 4H), 1.17-1.20 (m, 2H); $^{13}$C NMR (100 MHz, acetone-d$_6$): δ 175.8, 137.3, 127.4, 123.1, 121.8, 119.5, 119.2, 114.1, 111.9, 42.4, 39.6, 38.7, 32.9, 32.9, 25.3, 25.3; IR (neat): 3418, 1699, 1456, 1339, 1097 cm-1; FAB-MS: m/z [M]$^+$ 257.

Compounds #26 to 31 were each synthesized according to a method described in Muro Fumihito et. al. "Discovery of trans-4-[1-[[2,5-Dichloro-4-(1-methyl-3-indolylcarboxamido)phenyl]acetyl]-(4S)-methoxy-(2S)-pyrrolidinylmethoxy]cyclohexanecarboxylic Acid: An Orally Active, Selective Very Late Antigen-4 Antagonist" Journal of Medicinal Chemistry, 52 (24), 7974-7992; 2009.

Synthesis of Compound #26

N-Methyl-3-indoleacetic Acid Methyl Ester

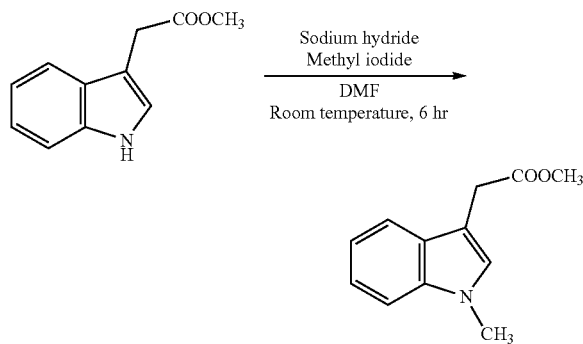

3-Indoleacetic acid methyl ester (200 mg, 1.1 mmol) was dissolved in N,N-dimethylformamide (3 mL). To the solution, sodium hydride (60 mg) was added. To this solution, methyl iodide (223 mg, 1.58 mmol) was added, and the mixture was stirred at room temperature for 6 hours. After the reaction was confirmed by TLC to be complete, the reaction solution was acidified (pH=3 to 4) by the addition of 6 N hydrochloric acid, and water (5 ml) was added thereto, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=5:1) to obtain N-methyl-3-indoleacetic acid methyl ester (140 mg, yield: 65%); $^1$H NMR (400 MHz, CDCl$_3$): δ 7.60 (d, J=7.9 Hz, 1H), 7.29 (d, J=8.2 Hz, 1H), 7.23 (dd, J=8.2, 7.9 Hz, 1H), 7.12 (dd, J=8.2, 7.9 Hz, 1H), 7.03 (s, 1H), 3.75 (s, 3H), 3.77 (s, 2H), 3.69 (s, 3H); $^{13}$C NMR (100 MHz, CDCl$_3$): δ 172.6, 136.9, 127.7, 121.7 (2C), 119.26, 118.9, 109.3, 106.8, 51.9, 32.7, 31.0.

N-Methyl-3-indoleacetic Acid (Compound #26)

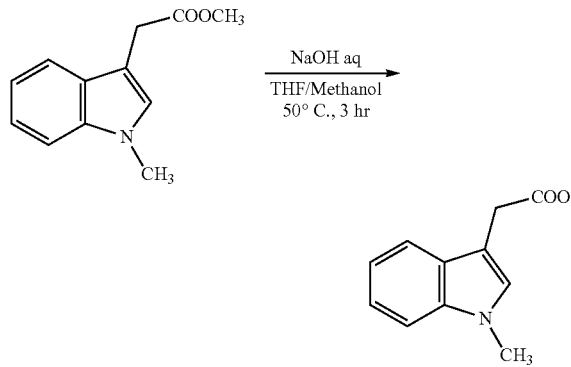

N-Methyl-3-indoleacetic acid methyl ester (120 mg, 0.59 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=10:1) to obtain N-methyl-3-indoleacetic acid (compound #26) (108 mg, yield: 96%); $^1$H NMR (400 MHz, CDCl$_3$): δ 7.59 (d, J=8.0 Hz, 1H), 7.35 (d, J=8.1 Hz, 1H), 7.18 (s, 1H), 7.16 (dd, J=7.0, 6.1 Hz, 1H), 7.04 (dd, J=8.1, 6.7 Hz, 1H), 3.79 (s, 3H), 3.73 (s, 2H). $^{13}$C NMR (100 MHz, CDCl$_3$): δ 177.6, 136.8, 127.9, 127.5, 121.8, 119.2, 118.9, 109.5, 106.1, 53.7, 31.7.

Synthesis of Compound #27

N-Ethyl-3-indoleacetic Acid Methyl Ester

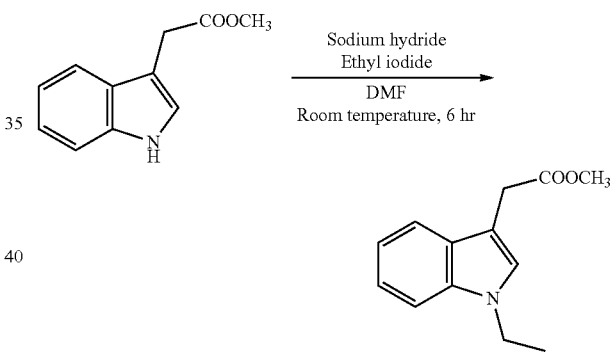

3-Indoleacetic acid methyl ester (200 mg, 1.1 mmol) was dissolved in N,N-dimethylformamide (3 mL). To the solution, sodium hydride (60 mg) was added. To this solution, ethyl iodide (246 mg, 1.58 mmol) was added, and the mixture was stirred at room temperature for 6 hours. After the reaction was confirmed by TLC to be complete, the reaction solution was acidified (pH=3 to 4) by the addition of 6 N hydrochloric acid, and water (5 ml) was added thereto, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=5:1) to obtain N-ethyl-3-indoleacetic acid methyl ester (133 mg, yield: 58%); $^1$H NMR (400 MHz, CDCl$_3$): δ 7.60 (d, J=7.8 Hz, 1H), 7.31 (d, J=8.3 Hz, 1H), 7.21 (dd, J=8.3, 7.8 Hz, 1H), 7.11 (dd, J=8.3, 7.8 Hz, 1H), 7.09 (s, 1H), 4.11 (q, J=7.3 Hz, 2H), 3.76 (s, 2H), 3.68 (s, 3H), 1.43 (t, J=7.3, 3H); $^{13}$C NMR (100 MHz, CDCl$_3$): δ 172.6, 160.8, 135.9, 127.8, 125.9, 121.6, 119.0, 109.3, 51.9, 40.8, 31.1, 15.4.

N-Ethyl-3-indoleacetic Acid (Compound #27)

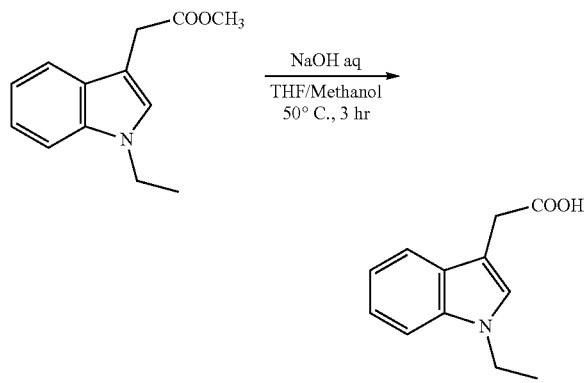

N-Methyl-3-indoleacetic acid methyl ester (120 mg, 0.59 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=10:1) to obtain N-methyl-3-indoleacetic acid (compound #27) (108 mg, yield: 97%); $^1$H NMR (400 MHz, CDCl$_3$): δ 7.60 (d, J=7.9 Hz, 1H), 7.40 (d, J=8.2 Hz, 1H), 7.25 (s, 1H), 7.15 (ddd, J=7.5, 7.6 Hz, 1H), 7.04 (ddd, J=7.3, 7.5 Hz, 1H), 4.20 (q, J=7.3 Hz, 2H), 3.74 (s, 2H), 1.39 (t, J=7.3 Hz, 3H); $^{13}$C NMR (100 MHz, CDCl$_3$): δ 173.3, 136.8, 129.0, 127.1, 122.0, 119.8, 119.4, 110.1, 108.1, 41.1, 31.9, 15.8.

Synthesis of Compound #28

N-Propyl-3-indoleacetic Acid Methyl Ester

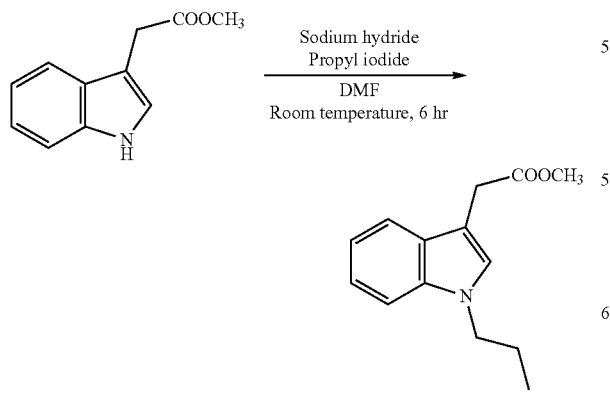

3-Indoleacetic acid methyl ester (200 mg, 1.1 mmol) was dissolved in N,N-dimethylformamide (3 mL). To the solution, sodium hydride (60 mg) was added. To this solution, propyl iodide (268 mg, 1.58 mmol) was added, and the mixture was stirred at room temperature for 6 hours. After the reaction was confirmed by TLC to be complete, the reaction solution was acidified (pH=3 to 4) by the addition of 6 N hydrochloric acid, and water (5 ml) was added thereto, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=6:1) to obtain N-propyl-3-indoleacetic acid methyl ester (136 mg, yield: 56%); $^1$H NMR (400 MHz, CDCl$_3$): δ 7.60 (d, J=7.8 Hz, 1H) 7.31 (d, J=8.3 Hz, 1H) 7.21 (dd, J=8.0, 7.1 Hz, 1H) 7.11 (dd, J=7.7, 6.9 Hz, 1H) 7.08 (s, 1H) 4.04 (t, J=7.1 Hz, 2H) 3.77 (s, 2H) 3.69 (s, 3H) 1.86 (m, 2H) 0.93 (t, J=7.3 Hz, 3H); $^{13}$C NMR (100 MHz, CDCl$_3$): δ 172.6, 136.2, 127.70, 126.7, 121.5, 119.0, 119.0, 109.4, 106.6, 51.9, 47.9, 31.1, 23.5, 11.5.

N-Propyl-3-indoleacetic Acid (Compound #28)

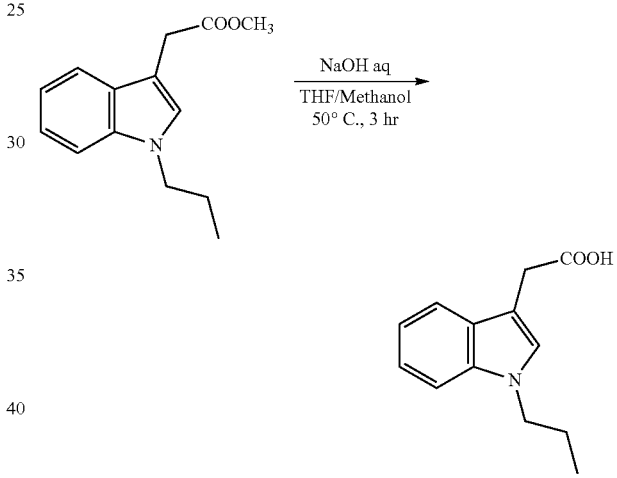

N-Propyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=10:1) to obtain N-propyl-3-indoleacetic acid (compound #28) (103 mg, yield: 98%); $^1$H NMR (400 MHz, CDCl$_3$): δ 7.60 (d, J=8.0 Hz, 1H), 7.32 (d, J=8.2 Hz, 1H), 7.21 (dd, J=7.2, 8.0 Hz, 1H), 7.11 (dd, J=7.3, 9.8 Hz, 1H), 7.09 (s, 1H), 4.04 (t, J=7.1 Hz, 2H), 3.79 (s, 2H), 1.85 (m, 2H), 0.92 (t, J=7.4 Hz, 3H); $^{13}$C NMR (100 MHz, CDCl$_3$): δ 177.5, 136.2, 127.6, 127.0, 121.6, 119.1, 119.0, 109.5, 106.0, 53.7, 31.7, 23.5, 11.5.

Synthesis of Compound #29

N-Butyl-3-indoleacetic Acid Methyl Ester

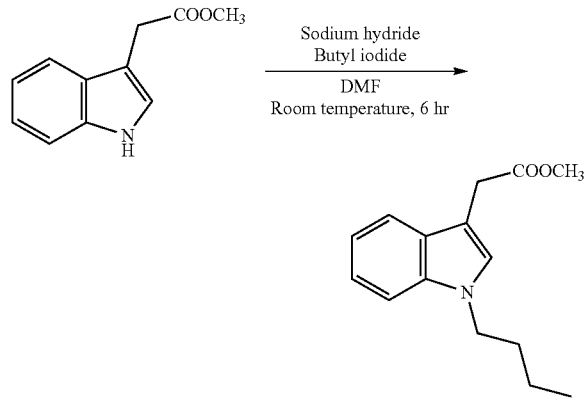

3-Indoleacetic acid methyl ester (200 mg, 1.1 mmol) was dissolved in N,N-dimethylformamide (3 mL). To the solution, sodium hydride (60 mg) was added. To this solution, butyl iodide (290 mg, 1.58 mmol) was added, and the mixture was stirred at room temperature for 6 hours. After the reaction was confirmed by TLC to be complete, the reaction solution was acidified (pH=3 to 4) by the addition of 6 N hydrochloric acid, and water (5 ml) was added thereto, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=6:1) to obtain N-butyl-3-indoleacetic acid methyl ester (137 mg, yield: 53%); $^1$H NMR (400 MHz, CDCl$_3$): δ 7.60 (d, J=7.8 Hz, 1H), 7.32 (d, J=8.2 Hz, 1H), 7.21 (dd, J=8.5, 9.8 Hz, 1H), 7.11 (dd, J=9.7, 7.4 Hz, 1H), 7.08 (s, 1H), 4.08 (t, J=7.1 Hz, 2H), 3.77 (s, 2H), 3.69 (s, 3H), 1.80 (m, 2H), 1.34 (m, 2H), 0.93 (t, J=7.4 Hz, 3H); $^{13}$C NMR (100 MHz, CDCl$_3$): δ 172.6, 136.2, 127.7, 126.7, 121.5, 119.0, 119.0, 109.4, 106.7, 51.9, 46.0, 32.3, 31.1, 20.2, 13.7.

N-Butyl-3-indoleacetic Acid (Compound #29)

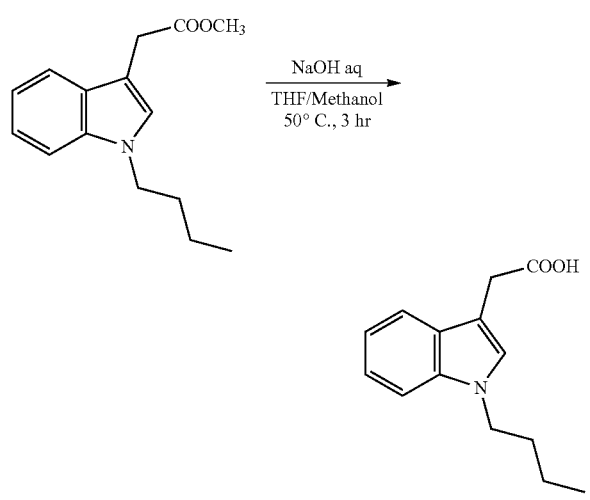

N-Butyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=10:1) to obtain N-butyl-3-indoleacetic acid (compound #29) (104 mg, yield: 98%); $^1$H NMR (400 MHz, CDCl$_3$): δ 7.59 (d, J=7.9 Hz, 1H), 7.31 (d, J=8.2 Hz, 1H), 7.20 (dd, J=7.1, 7.9 Hz, 1H), 7.11 (dd, J=7.3, 7.5 Hz, 1H), 7.07 (s, 1H), 4.06 (t, J=7.2 Hz, 2H), 3.78 (s, 2H), 1.79 (m, 2H), 1.33 (m, 2H), 0.92 (t, J=7.4, 3H); $^{13}$C NMR (100 MHz, CDCl$_3$): δ 178.0, 136.1, 127.6, 126.9, 121.6119.10, 119.0, 109.5, 106.0, 53.6, 31.7, 29.1, 20.2, 13.7.

Synthesis of Compound #30

N-Hexyl-3-indoleacetic Acid Methyl Ester

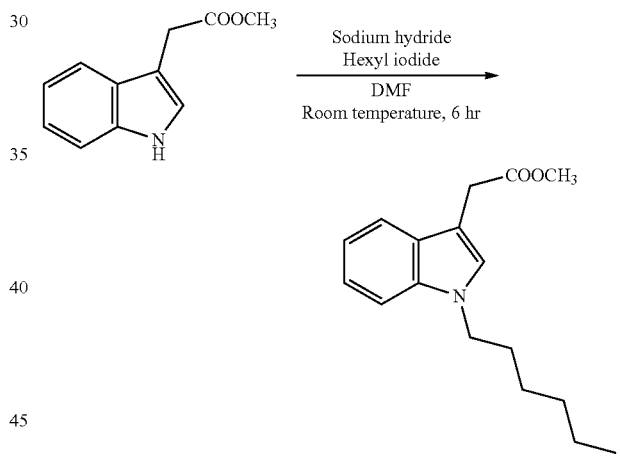

3-Indoleacetic acid methyl ester (200 mg, 1.1 mmol) was dissolved in N,N-dimethylformamide (3 mL). To the solution, sodium hydride (60 mg) was added. To this solution, hexyl iodide (334 mg, 1.58 mmol) was added, and the mixture was stirred at room temperature for 6 hours. After the reaction was confirmed by TLC to be complete, the reaction solution was acidified (pH=3 to 4) by the addition of 6 N hydrochloric acid, and water (5 ml) was added thereto, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane:ethyl acetate=6:1) to obtain N-hexyl-3-indoleacetic acid methyl ester (147 mg, yield: 51%); $^1$H NMR (400 MHz, CDCl$_3$): δ 7.60 (d, J=7.8 Hz, 1H) 7.31, (d, J=8.2 Hz, 1H), 7.20 (ddd, J=8.6, 5.6 Hz, 1H), 7.11 (ddd, J=8.0, 7.3 Hz, 1H), 7.08 (s, 2H), 4.06 (t, J=7.2 Hz, 2H), 3.77 (s, 2H), 3.69 (s, 3H), 1.81 (m, 2H), 1.30 (m, 6H), 0.87 (t, J=6.9 Hz, 3H); $^{13}$C NMR (100 MHz, CDCl₃): δ 172.6, 136.1, 127.7, 126.7, 121.5, 119.0, 119.0, 109.4, 106.6, 51.9, 46.3, 31.4, 31.1, 30.2, 22.6, 22.5, 14.0.

N-Hexyl-3-indoleacetic Acid (Compound #30)

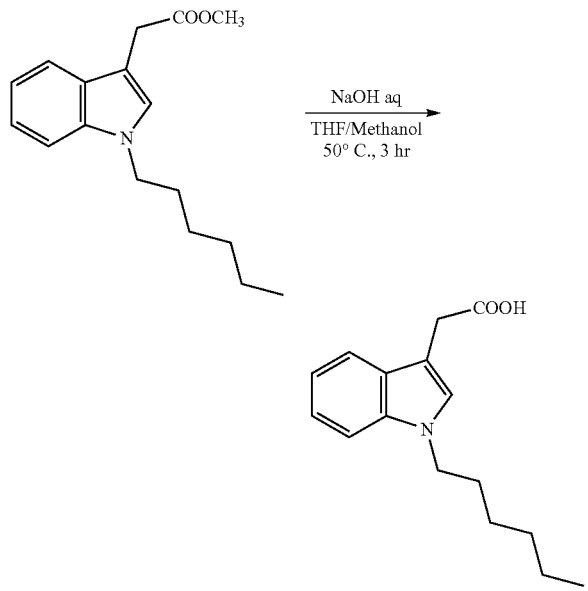

N-Hexyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=10:1) to obtain N-hexyl-3-indoleacetic acid (compound #30) (103 mg, yield: 96%); ¹H NMR (400 MHz, CDCl₃): δ 7.59 (d, J=7.9 Hz, 1H), 7.31 (d, J=8.2 Hz, 1H), 7.20 (ddd, J=7.9, 7.3 Hz, 1H), 7.20 (ddd, J=7.4, 7.7 Hz, 1H), 7.07 (1H, s, 1H), 4.05 (t, J=7.2 Hz, 2H), 3.78 (s, 2H), 1.81 (m, 2H), 1.31 (m, 6H), 0.88 (t, J=6.3 Hz, 3H); ¹³C NMR (100 MHz, CDCl₃): δ 178.0, 136.1, 127.6, 127.6, 121.6, 119.1, 119.0, 109.5, 106.0, 53.7, 31.7, 29.2, 28.9, 27.0, 23.0, 14.02.

Synthesis of Compound #31

N-Heptyl-3-indoleacetic Acid Methyl Ester

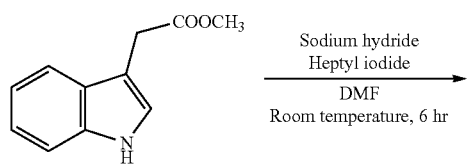

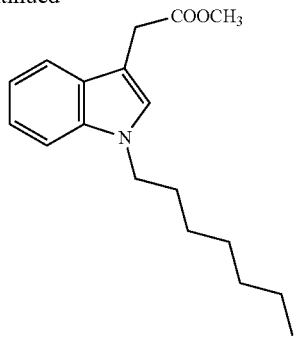

3-Indoleacetic acid methyl ester (200 mg, 1.1 mmol) was dissolved in N,N-dimethylformamide (3 mL). To the solution, sodium hydride (60 mg) was added. To this solution, heptyl iodide (358 mg, 1.58 mmol) was added, and the mixture was stirred at room temperature for 6 hours. After the reaction was confirmed by TLC to be complete, the reaction solution was acidified (pH=3 to 4) by the addition of 6 N hydrochloric acid, and water (5 ml) was added thereto, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (hexane: ethyl acetate=6:1) to obtain N-heptyl-3-indoleacetic acid methyl ester (148 mg, yield: 49%); ¹H NMR (400 MHz, CDCl₃): δ 3.69 (3H, s), 7.60 (1H, d, J=7.8), 7.31 (1H, d, J=8.2) 7.11 (1H, dd, J=8.2, 6.7), 7.08 (1H, s), 4.06 (2H, t, J=7.1), 3.77 (2H, s) 3.59 (1H, dd, J=8.2, 6.7), 1.82 (2H, m), 1.29 (8H, m), 0.87 (3H, t, J=7.1); ¹³C NMR (100 MHz, CDCl₃): δ 172.57, 136.16, 127.70, 126.66, 121.54, 118.98, 118.98, 109.43, 106.64, 51.89, 46.31, 31.67, 31.11, 30.24, 28.89, 26.96, 22.55, 14.02.

N-Heptyl-3-indoleacetic Acid (Compound #31)

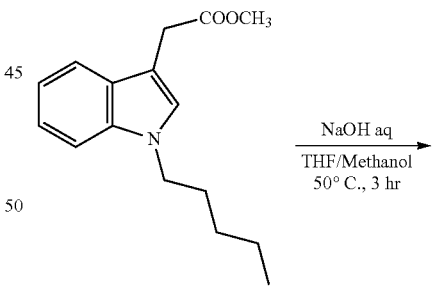

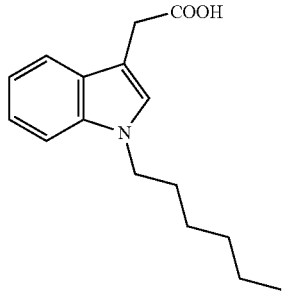

N-Heptyl-3-indoleacetic acid methyl ester (120 mg, 0.52 mmol) was dissolved in tetrahydrofuran (0.5 ml). To this solution, methanol (0.5 ml) and a 2 N aqueous sodium hydroxide solution (0.25 ml) were added, and the mixture was stirred at 50° C. for 3 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=10:1) to obtain N-heptyl-3-indoleacetic acid (compound #31) (180 mg, yield: 95%); $^1$H NMR (400 MHz, CDCl$_3$): δ 7.59 (1H, d, J=7.96), 7.31 (1H, d, J=8.17), 7.21 (1H, ddd, J=8.49, 6.73), 7.11 (1H, ddd, J=7.21, 7.29), 7.08 (1H, S), 4.06 (2H, t, J=7.25), 3.79 (2H, s) 1.81 (2H, m) 1.29 (8H, m) 0.87 (3H, t, J=6.83); $^{13}$C NMR (100 MHz, CDCl$_3$): δ 177.81, 136.10, 127.55, 126.85, 121.62, 119.11, 118.94, 109.49, 105.91, 53.63, 46.32, 30.99, 29.68, 29.16, 26.64, 22.49, 13.99.

Compounds #33 and 34 were each synthesized with α-(7-hydroxy-1-naphthalenyl)-acetic acid ethyl ester as a key intermediate. The α-(7-hydroxy-1-naphthalenyl)-acetic acid ethyl ester was synthesized according to a method described in E. Tsuda et. al., "Alkoxy-auxins are selective inhibitors of auxin transport mediated by PIN, ABCB, and AUX1 transporters" Journal of Biological Chemistry, 286 (3), 2354-2364; 2011.

Synthesis of Compound #33

α-(7-Butoxy-1-naphthalenyl)-acetic Acid Ethyl Ester

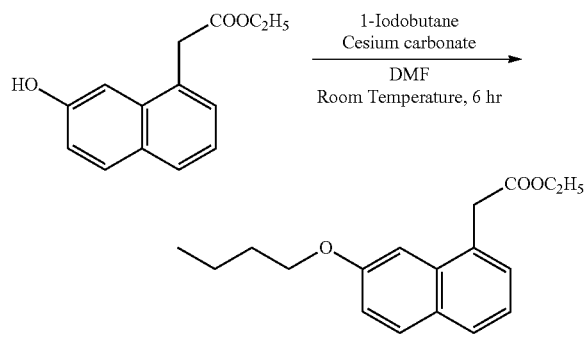

α-(7-Hydroxy-1-naphthalenyl)-acetic acid ethyl ester (90 mg, 0.39 mmol) was dissolved in N,N-dimethylformamide (5 ml). To this solution, 1-iodobutane (107 mg, 0.58 mmol) was added dropwise, then cesium carbonate (127 mg, 0.39 mmol) was added, and the mixture was stirred at room temperature for 6 hours. After the reaction was confirmed by TLC to be complete, water (5 ml) was added to the reaction solution, followed by extraction with ethyl acetate (10 ml) three times. The organic layer was washed twice with brine and dried over anhydrous sodium sulfate. The solvent was distilled off under reduced pressure, and then, the residue was purified by silica gel column chromatography (hexane: ethyl acetate=7:3) to obtain α-(7-butoxy-1-naphthalenyl)-acetic acid ethyl ester as a colorless oil (92 mg, yield: 83%); $^1$H NMR (400 MHz, CDCl$_3$): δ 7.71 (d, J=8.9 Hz, 1H), 7.35 (d, J=6.9 Hz, 1H), 7.67 (d, J=8.1 Hz, 1H), 7.27 (d, J=2.3 Hz, 1H), 7.25 (dd, J=8.1, 6.9 Hz, 1H), 7.14 (q, J=8.9, 2.3 Hz, 1H), 4.12 (q, J=7.1 Hz, 2H), 4.07 (t, J=6.6 Hz, 2H), 3.97 (s, 2H), 1.82 (m, 2H), 1.53 (m, 2H), 1.19 (t, J=7.1 Hz, 3H), 0.96 (t, J=7.5 Hz, 3H); $^{13}$C NMR (100 MHz, CDCl$_3$): δ 171.5, 157.4, 133.2, 130.0, 129.3, 129.1, 128.3, 127.6, 123.0, 118.5, 103.2, 67.6, 60.8, 39.5, 31.2, 19.2, 14.1, 13.8; IR (neat): 2958, 1733, 1510, 1459, 1210, 1156 cm$^{-1}$; HREI-MS: m/z [M]$^+$; calcd for 286.1569 (C$_{18}$H$_{22}$O$_3$), found, 286.1556.

α-(7-Butoxy-1-naphthalenyl)-acetic Acid (Compound #33)

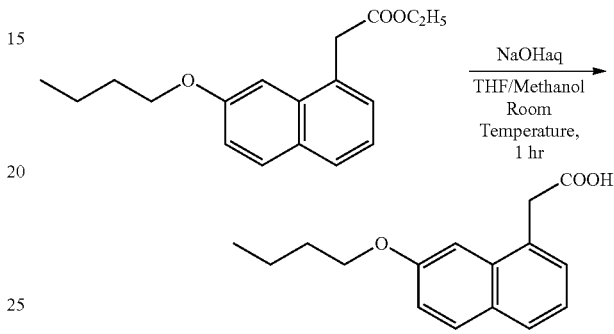

α-(7-Butoxy-1-naphthalenyl)-acetic Acid Ethyl Ester (75 mg, 0.26 mmol) was dissolved in a mixed solution of tetrahydrofuran:methanol:2 M aqueous sodium hydroxide solution=2:2:1 (1.5 ml), and the solution was stirred at room temperature for 1 hour. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (10 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain α-(7-butoxy-1-naphthalenyl)-acetic acid (compound #33) (67 mg, yield: 98%); Melting point: 102 to 104° C.; $^1$H NMR (400 MHz, CDCl$_3$): δ 7.75 (d, J=8.9 Hz, 1H), 7.71 (d, J=8.1 Hz, 1H), 7.34 (d, J=6.9 Hz, 1H), 7.26 (dd, J=8.1, 6.9 Hz, 1H), 7.23 (d, J=2.0 Hz, 1H), 7.16 (q, J=8.9, 2.0 Hz, 1H), 4.05 (t, J=6.5 Hz, 2H), 4.00 (s, 2H), 1.51 (m, 2H), 1.80 (m, 2H), 0.98 (t, J=7.4 Hz, 3H); $^{13}$C NMR (100 MHz, CDCl$_3$): δ 177.6, 157.6, 133.2, 130.2, 129.1, 128.6, 127.9 (2C), 123.0, 118.7, 103.1, 67.7, 39.2, 31.2, 19.3, 13.8; IR (neat): 3021, 2931, 1699, 1457, 1138 cm$^{-1}$; HREI-MS: m/z [M]$^+$ calcd for 258.1256 (C$_{16}$H$_{18}$O$_3$), found 258.1268.

Synthesis of Compound #34

α-(7-Pentoxy-1-naphthalenyl)-acetic Acid Ethyl Ester

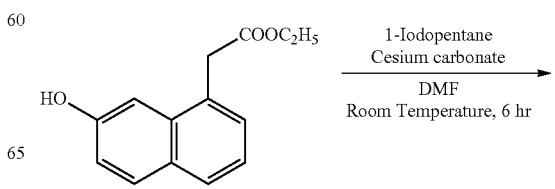

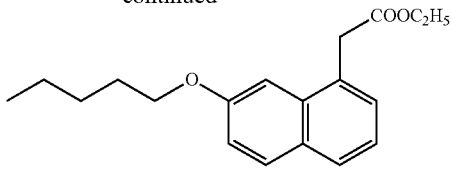

α-(7-Hydroxy-1-naphthalenyl)-acetic acid ethyl ester (90 mg, 0.39 mmol) was dissolved in N,N-dimethylformamide (5 ml). To this solution, 1-iodopentane (116 mg, 0.58 mmol) was added dropwise, then cesium carbonate (127 mg, 0.39 mmol) was added, and the mixture was stirred at room temperature for 6 hours. After the reaction was confirmed by TLC to be complete, water (5 ml) was added to the reaction solution, followed by extraction with ethyl acetate (10 ml) three times. The organic layer was washed twice with brine and dried over anhydrous sodium sulfate. The solvent was distilled off under reduced pressure, and then, the residue was purified by silica gel column chromatography (hexane: ethyl acetate=7:3) to obtain α-(7-pentoxy-1-naphthalenyl)-acetic acid ethyl ester as a colorless oil (103 mg, yield: 88%); $^1$H NMR (400 MHz, CDCl$_3$): δ 1.00 (t, J=7.2 Hz, 3H), 1.26 (t, J=7.1 Hz, 3H), 1.48 (m, 2H), 1.55 (m, 2H), 1.91 (m, 2H), 4.03 (s, 2H), 4.13 (t, J=6.5 Hz, 2H), 4.19 (q, J=7.1 Hz, 2H), 7.20 (dd, J=8.9, 2.5 Hz, 1H), 7.31 (dd, J=8.1, 7.0 Hz, 1H), 7.33 (d, J=2.5 Hz, 1H), 7.41 (d, J=7.0 Hz, 1H), 7.74 (d, J=8.1 Hz, 1H), 7.78 (d, J=8.9 Hz, 1H); $^{13}$C NMR (100 MHz, CDCl$_3$): δ 171.5, 157.4, 133.2, 130.0, 129.3, 129.1, 128.4, 127.6, 123.0, 118.5, 103.2, 67.8, 60.8, 39.6, 28.9, 28.2, 22.4, 14.1, 14.0; IR (neat): 2969, 1734, 1509, 1459, 1160 cm$^{-1}$; HREI-MS: m/z [M]$^+$ calcd for 300.1725 (C$_{19}$H$_{24}$O$_3$), found, 300.1727.

α-(7-Pentoxy-1-naphthalenyl)-acetic Acid (Compound #34)

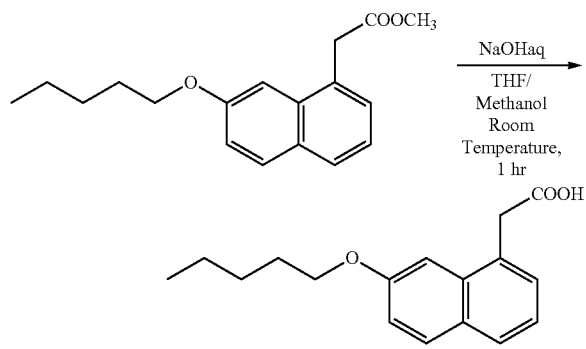

α-(7-Pentoxy-1-naphthalenyl)-acetic acid ethyl ester (90 mg, 0.30 mmol) was dissolved in a mixed solution of tetrahydrofuran:methanol:2 M aqueous sodium hydroxide solution=2:2:1 (1.5 ml), and the solution was stirred at room temperature for 1 hour. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (10 ml) three times. The organic layer was washed twice with brine and dried over anhydrous sodium sulfate. The solvent was distilled off under reduced pressure, and then, the residue was purified by silica gel column chromatography (chloroform:methanol=6:1) to obtain α-(7-pentoxy-1-naphthalenyl)-acetic acid (compound #34) (75 mg, yield: 92%); Melting point: 104 to 106° C.; $^1$H NMR (400 MHz, CDCl$_3$): δ 7.71 (d, J=8.1 Hz, 1H), 7.39 (d, J=6.9 Hz, 1H), 7.26 (t, J=8.1, 6.9 Hz, 1H), 7.21 (d, J=2.1 Hz, 1H), 7.15 (dd, J=8.9, 2.1 Hz, 1H), 4.03 (t, J=6.5 Hz, 2H), 4.00 (s, 2H), 3.87 (d, J=8.9 Hz, 1H), 1.82 (m, 2H), 1.45 (m, 2H), 1.39 (m, 2H), 0.93 (t, J=7.1 Hz, 3H); $^{13}$C NMR (100 MHz, CDCl$_3$): δ 177.6, 157.6, 133.2, 130.2, 129.1, 128.6, 128.4, 128.0, 123.0, 118.7, 103.1, 68.0, 39.1, 28.9, 28.2, 22.5, 14.0; IR (neat): 3014, 2945, 1689, 1463, 1169 cm$^{-1}$; EI-MS m/z [M]$^+$; HREI-MS: m/z [M]$^+$ calcd for 272.1412 (C$_{17}$H$_{20}$O$_3$), found, 272.1378.

Compounds #35 to 37 were each synthesized with 5-hydroxy-3-indoleacetic acid methyl ester as a key intermediate.

5-Hydroxy-3-indoleacetic Acid Methyl Ester

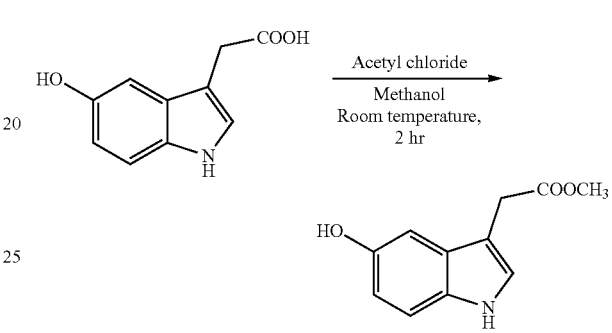

5-Hydroxy-3-indoleacetic acid (1.00 g) was dissolved in methanol (25 ml). To the solution, acetyl chloride (1.0 ml) was slowly added dropwise, and the mixture was stirred at room temperature for 2 hours. After the reaction was confirmed by TLC to be complete, the reaction was quenched by the addition of a saturated aqueous solution of sodium bicarbonate, and the solvent was distilled off under reduced pressure. Then, water (20 ml) was added to the residue, followed by extraction with ethyl acetate (50 ml) three times. The organic layer was washed twice with brine and dried over anhydrous sodium sulfate. The solvent was distilled off under reduced pressure, and then, the residue was purified by silica gel column chromatography (hexane: ethyl acetate=3:2) to obtain 5-hydroxy-3-indoleacetic acid methyl ester (1.05 g, yield: 98%); $^1$H NMR (400 MHz, CDCl$_3$): δ 7.20 (s, J=8.7 Hz, 1H), 7.13 (d, J=2.4 Hz, 1H), 7.00 (d, J=2.4 Hz, 1H), 6.78 (dd, J=8.8, 2.4 Hz, 1H), 3.72 (s, 2H), 3.70 (s, 3H); $^{13}$C NMR (100 MHz, CDCl$_3$): δ 172.6, 149.6, 131.4, 127.9, 124.2, 112.1, 111.9, 103.4, 107.8, 52.0, 31.2; IR (neat): 3411, 3000, 2952, 1728, 1459, 1459, 1154 cm$^{-1}$; EI-MS m/z [M]$^+$ 205, 146; HREI-MS: m/z [M]$^+$ calcd for 205.0739 (C$_{11}$H$_{11}$NO$_3$), found, 205.0761.

Synthesis of compound #35

5-(3,5-Dimethoxybenzyloxy)-3-indoleacetic Acid Methyl Ester

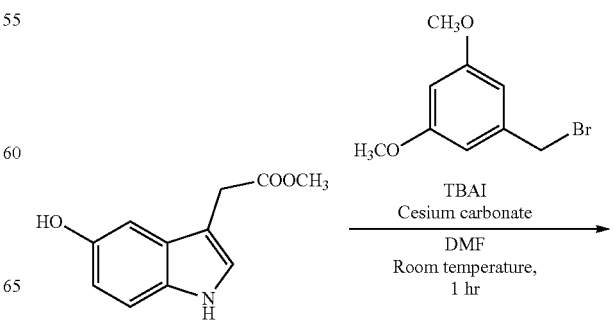

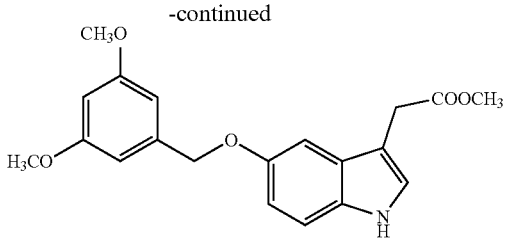

5-Hydroxy-3-indoleacetic acid methyl ester (42.9 mg, 0.21 mmol) was dissolved in N,N-dimethylformamide (DMF). To this solution, 3,5-dimethoxybenzyl bromide (82.2 mg, 0.36 mmol) was added dropwise, then tetra-N-butylammonium iodide (83.0 mg, 2.00 mmol) and cesium carbonate (136.37 mg, 0.42 mmol) put aside in another container were added, and the mixture was stirred at room temperature for 1 hour. After the reaction was confirmed by TLC to be complete, the reaction was quenched by the addition of an aqueous sodium bicarbonate solution, followed by extraction with ethyl acetate (50 ml) three times. The organic layer was washed twice with brine and dried over anhydrous sodium sulfate. The solvent was distilled off under reduced pressure, and then, the residue was purified by silica gel column chromatography (hexane:ethyl acetate=3:2) to obtain 5-(3,5-dimethoxybenzyloxy)-3-indoleacetic acid methyl ester (81.5 mg, yield: 94%); $^1$H NMR (400 MHz, CDCl$_3$): δ 7.17 (d, J=2.2 Hz, 1H), 7.12 (d, J=8.7 Hz, 1H), 7.04 (s, 2H), 6.92 (dd, J=8.7, 2.2 Hz, 1H), 6.64 (d, J=2.2 Hz, 2H), 6.41 (t, J=2.2 Hz, 1H), 5.13 (s, 2H), 3.78 (s, 6H), 3.72 (s, 2H), 3.67 (s, 3H); $^{13}$C NMR (100 MHz, CDCl$_3$): δ 172.5, 160.9 (2C), 153.2, 140.0, 131.4, 124.0, 127.5, 113.0, 111.9, 107.9, 105.2 (2C), 102.2, 99.8, 70.8, 55.3 (2C), 51.9, 31.2; IR (neat): 3396, 2948, 1734, 1449, 1159 cm$^{-1}$.

5-(3,5-Dimethoxybenzyloxy)-3-indoleacetic Acid (Compound #35)

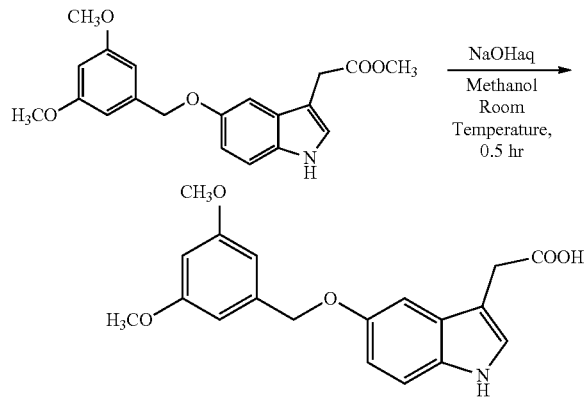

5-(3,5-Dimethoxybenzyloxy)-3-indoleacetic acid methyl ester (81.5 mg, 0.23 mmol) was dissolved in tetrahydrofuran (0.5 ml). To this solution, methanol (0.5 ml) and a 2 N aqueous sodium hydroxide solution (0.25 ml) were added, and the mixture was stirred at room temperature for 0.5 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol 10:1) to obtain 5-(3,5-dimethoxybenzyloxy)-3-indoleacetic acid (compound #35) (55.2 mg, yield: 100%); Melting point: 146.1 to 148.6° C.; $^1$H NMR (400 MHz, CDCl$_3$): δ 7.19 (d, J=8.8 Hz, 1H), 7.12 (d, J=2.2 Hz, 1H), 7.06 (s, 1H), 6.92 (dd, J=8.8, 2.2 Hz, 1H), 6.68 (d, J=2.2 Hz, 2H), 6.40 (t, J=2.2 Hz, 1H), 5.01 (S, 2H), 3.77 (S, 6H), 3.73 (s, 2H); $^{13}$C NMR (100 MHz, CDCl$_3$): δ 177.5, 160.8 (2C), 153.3, 140.0, 131.4, 127.5, 124.1, 113.1, 112.0, 107.4, 105.3 (2C), 102.2, 99.9, 70.9, 55.3 (2C), 31.1; IR (neat): 3406, 2957, 2926, 1702, 1458, 1155 cm$^{-1}$ Synthesis of Compound #36

5-Methoxy-3-indoleacetic Acid Methyl Ester

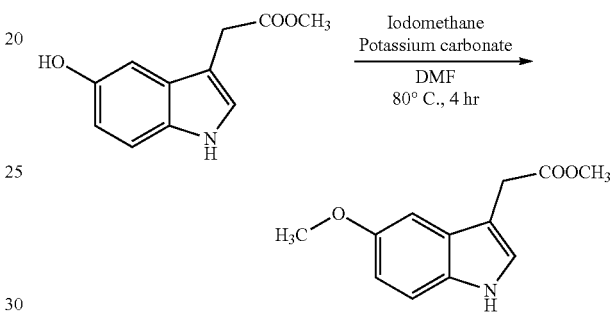

5-Hydroxy-3-indoleacetic acid methyl ester (99.3 mg, 0.48 mmol) was dissolved in N,N-dimethylformamide (2 ml). To this solution, iodomethane (206.2 mg, 1.45 mmol) was added dropwise, then potassium carbonate (200.8 mg, 1.45 mmol) put aside in another container was added, and the mixture was stirred overnight at room temperature and subsequently stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with brine and dried over anhydrous sodium sulfate. The solvent was distilled off under reduced pressure, and then, the residue was purified by silica gel column chromatography (hexane:ethyl acetate=7:3) to obtain 5-methoxy-3-indoleacetic acid methyl ester (58.6 mg, yield: 55.2%); $^1$H NMR (400 MHz, CDCl$_3$): δ 7.22 (1H, d. J=8.8), 7.11 (d, J=2.3 Hz, 1H), 7.05 (d, J=1.3 Hz, 1H), 6.93 (dd, J=8.8, 2.3 Hz, 1H), 3.70 (s, 3H), 3.85 (s, 3H), 3.74 (s, 2H); $^{13}$C NMR (100 MHz, CDCl$_3$): δ 172.5, 154.2, 131.2, 127.6, 123.8, 112.5, 111.9, 108.1, 100.6, 55.9, 51.9, 31.2; IR (neat): 3403, 2951, 1729, 1486, 1213, 1154 cm$^{-1}$; EI-MS m/z [M]$^+$ 219, 160; HREI-MS: m/z [M]$^+$ calcd for 219.0895 (C$_{12}$H$_{13}$NO$_3$), found, 219.0886.

5-Methoxy-3-indoleacetic Acid (Compound #36)

Synthesis of Compound #5

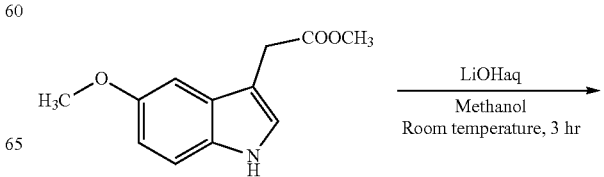

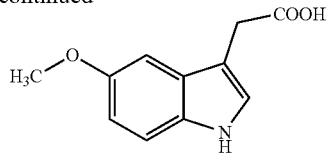

5-Methoxy-3-indoleacetic acid methyl ester (60.0 mg, 0.27 mmol) was dissolved in methanol (2 ml). To the solution, lithium hydroxide (19.7 mg, 0.82 mmol) was added, and the mixture was stirred at room temperature for 3 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain 5-methoxy-3-indoleacetic acid (compound #36) (15.3 mg, yield: 27.2%); Melting point: 147.0 to 149.8° C.; $^1$H NMR (400 MHz, CDCl$_3$): δ 7.28 (d, J=8.8 Hz, 1H), 7.26 (s, 1H), 7.11 (d, J=2.3 Hz, 1H), 6.77 (dd, J=8.8, 2.3 Hz, 1H), 3.80 (s, 3H), 3.71 (s, 1H); $^{13}$C NMR (100 MHz, CDCl$_3$): δ 173.3, 154.8, 132.6, 128.9, 125.2, 112.7, 112.4, 108.8, 101.4, 55.8, 31.5; IR (neat): 3359, 2996, 2851, 1705, 1456, 1137 cm$^{-1}$; EI-MS m/z [M]$^+$ 205 (75%), 160; HREI-MS: m/z [M]$^+$ calcd for 205.0739 (C$_{11}$H$_{11}$NO$_3$), found, 205.0737.

Synthesis of Compound #37

5-Ethoxy-3-indoleacetic Acid Methyl Ester

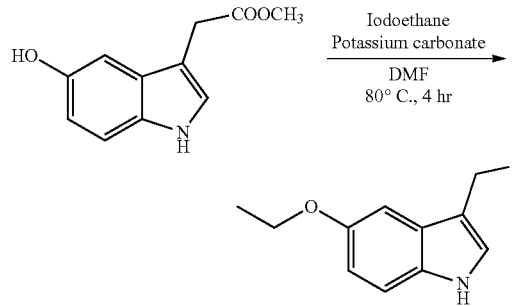

5-Hydroxy-3-indoleacetic acid methyl ester (109.0 mg, 0.53 mmol) was dissolved in N,N-dimethylformamide (2 ml). To this solution, iodoethane (248.74 mg, 1.60 mmol) was added dropwise, then potassium carbonate (220.5 mg, 1.60 mmol) put aside in another container was added, and the mixture was stirred at room temperature for 2 hours and stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with brine and dried over anhydrous sodium sulfate. The solvent was distilled off under reduced pressure, and then, the residue was purified by silica gel column chromatography (hexane:ethyl acetate=7:3) to obtain 5-ethoxy-3-indoleacetic acid methyl ester (100.7 mg, yield: 81.2%); $^1$H NMR (400 MHz, CDCl$_3$): δ 7.86 (q, J=7.0 Hz, 2H), 7.23 (d, J=8.8 Hz, 1H), 7.05 (d, J=2.3 Hz, 1H), 7.12 (d, J=2.0 Hz, 1H), 6.87 (dd, J=8.8, 2.3 Hz, 1H), 3.75 (s, 2H), 3.70 (s, 3H), 1.45 (t, J=7.0 Hz, 3H); $^{13}$C NMR (100 MHz, CDCl$_3$): δ 172.5, 153.4, 131.2, 127.6, 123.7, 113.0, 111.8, 108.1, 101.8, 64.2, 52.0, 31.2, 15.0; IR (neat): 3404, 2978, 1729, 1474, 1211, 1154 cm$^{-1}$; HREI-MS: m/z [M]$^+$ calcd for 233.1052 (C$_{13}$H$_{15}$NO$_3$), found, 233.1034.

5-Ethoxy-3-indoleacetic Acid (Compound #37)

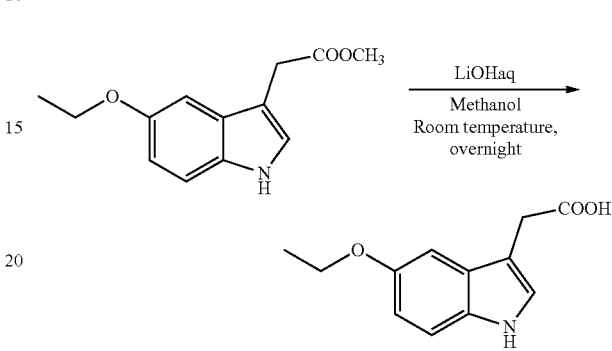

5-Ethoxy-3-indoleacetic acid methyl ester (90.2 mg, 0.27 mmol) was dissolved in methanol (4 ml). To the solution, lithium hydroxide (13.9 mg, 0.58 mmol) was added, and the mixture was stirred overnight at room temperature. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain 5-ethoxy-3-indoleacetic acid (compound #37) (83.8 mg, yield: 98.9%); Melting point: 86.0 to 92.7° C.; $^1$H NMR (400 MHz, CDCl$_3$): δ 7.23 (d, J=8.8 Hz, 1H), 7.12 (d, J=1.9 Hz, 1H), 7.04 (d, J=2.3 Hz, 1H), 6.86 (dd, J=8.8, 2.3 Hz, 1H), 4.09 (q, J=7.0 Hz, 2H), 3.80 (s, 2H), 1.42 (t, J=7.0 Hz, 3H); $^{13}$C NMR (100 MHz, CDCl$_3$): δ 177.4, 153.5, 131.2, 127.5, 124.0, 113.2, 111.9, 107.7, 101.7, 64.2, 31.1, 15.0; IR (neat): 3354, 3066, 2930, 1695, 1457, 1112 cm$^{-1}$; EI-MS m/z [M]$^+$ 219, 205 (40%), 190, 174, 162 (70%), 160 (50%); HREI-MS: m/z [M]$^+$ calcd for 219.0895 (C$_{12}$H$_{13}$NO$_3$), found, 219.0886.

Synthesis of Compound #38

5-(1-Propoxy)-3-indoleacetic Acid Methyl Ester

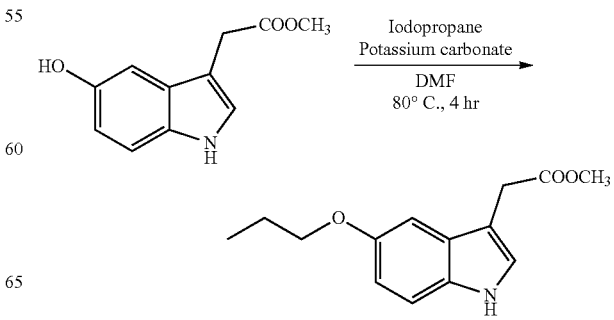

5-Hydroxy-3-indoleacetic acid methyl ester (108.4 mg, 0.53 mmol) was dissolved in N,N-dimethylformamide (2 ml). To this solution, iodopropane was added dropwise, then potassium carbonate (219.3 mg, 1.59 mmol) put aside in another container was added, and the mixture was stirred at room temperature for 2 hours and stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with brine and dried over anhydrous sodium sulfate. The solvent was distilled off under reduced pressure, and then, the residue was purified by silica gel column chromatography (hexane:ethyl acetate=7:3) to obtain 5-(1-propoxy)-3-indoleacetic acid methyl ester (78.6 mg, yield: 60.1%); Melting point: 38.6 to 41.0° C.; $^1$H NMR (400 MHz, CDCl$_3$): δ 7.21 (d, J=8.8 Hz, 1H), 7.10 (d, J=2.3 Hz, 1H), 7.05 (d, J=2.3 Hz, 1H), 6.86 (dd, J=8.8, 2.3 Hz, 1H), 4.01 (t, J=6.7 Hz, 2H), 3.74 (s, 2H), 3.70 (s, 3H), 1.82 (m, 2H), 1.07 (t, J=6.7 Hz, 3H); $^{13}$C NMR (100 MHz, CDCl$_3$): δ 172.5, 153.6, 131.2, 127.6, 123.7, 113.0, 111.8, 108.0, 101.7, 70.4, 52.0, 31.2, 22.8, 10.6; IR (neat): 3355, 3061, 2961, 1695, 1457, 1126 cm$^{-1}$; EI-MS m/z [M]$^+$ 247 (70%), 188 (30%), 149, 131 (75%); HREI-MS: m/z [M]$^+$ calcd for 247.1208 (C$_{14}$H$_{17}$NO$_3$), found, 247.1225.

5-(1-Propoxy)-3-indoleacetic Acid (Compound #38)

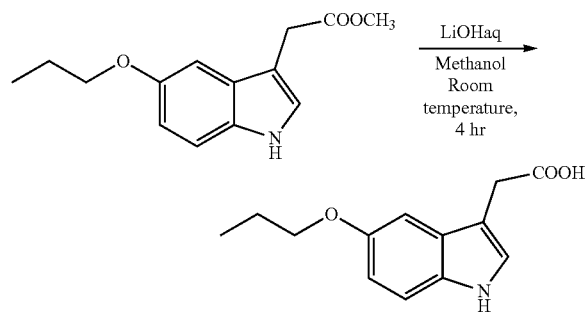

5-(1-Propoxy)-3-indoleacetic acid methyl ester (64.3 mg, 0.26 mmol) was dissolved in methanol (2 ml). To the solution, lithium hydroxide (9.35 mg, 0.39 mmol) was added, and the mixture was stirred at room temperature for 4 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain 5-(1-propoxy)-3-indoleacetic acid (compound #38) (59.3 mg, yield: 97.7%); Melting point: 133.6 to 136.8° C.; $^1$H NMR (400 MHz, CDCl$_3$): δ 7.23 (d, J=8.8 Hz, 1H), 7.13 (s, 1H), 7.04 (d, J=2.2 Hz, 1H), 6.87 (dd, J=8.1, 2.2 Hz, 1H), 3.96 (t, J=6.6 Hz, 2H), 3.76 (s, 3H), 1.82 (m, 2H), 1.05 (t. J=7.4 Hz, 3H); $^{13}$C NMR (100 MHz, CDCl$_3$): δ 177.4, 153.7, 131.2, 127.5, 123.9, 113.2, 111.9, 107.5, 101.7, 70.4, 31.0, 22.8, 10.6, 10.6; IR (neat): 3407, 2954, 1728, 1456, 1213, 1160 cm$^{-1}$; EI-MS m/z [M]$^+$ 233, 191 (50%); HREI-MS: m/z [M]$^+$ calcd for 233.1052 (C$_{12}$H$_{15}$NO$_3$), found 233.1043.

Synthesis of Compound #39

5-(1-Butoxy)-3-indoleacetic Acid Methyl Ester

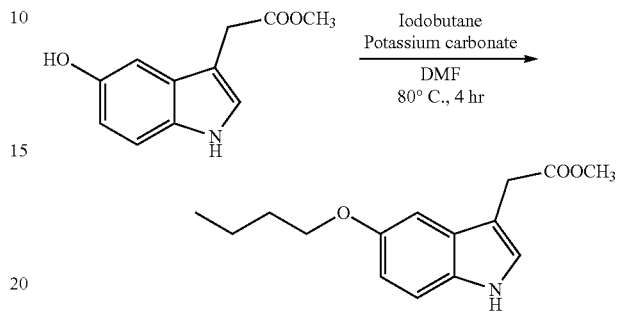

5-Hydroxy-3-indoleacetic acid methyl ester (108.4 mg, 0.53 mmol) was dissolved in N,N-dimethylformamide (2 ml). To this solution, iodobutane was added dropwise, then potassium carbonate (184.2 mg, 1.33 mmol) put aside in another container was added, and the mixture was stirred at 80° C. for 4 hours. After the reaction was confirmed by TLC to be complete, a 10% aqueous sodium bicarbonate solution (20 ml) was added thereto, followed by extraction with ethyl acetate (50 ml). The organic layer was washed twice with brine and dried over anhydrous sodium sulfate. The solvent was distilled off under reduced pressure, and then, the residue was purified by silica gel column chromatography (hexane:ethyl acetate=7:3) to obtain 5-(1-butoxy)-3-indoleacetic acid methyl ester (140.2 mg, yield: 80.5%); $^1$H NMR (400 MHz, CDCl$_3$): δ 7.21 (d, J=7.2 Hz, 1H), 7.10 (d, J=2.3 Hz, 1H), 7.05 (d, J=2.3 Hz, 1H), 6.86 (dd, J=8.8, 2.3 Hz, 1H), 4.01 (t, J=6.5 Hz, 2H), 3.74 (s, 2H), 3.70 (s, 3H), 1.82 (m, 2H), 1.52 (m, 2H), 0.98 (t, J=7.4 Hz, 3H); $^{13}$C NMR (100 MHz, CDCl$_3$): δ 172.5, 153.6, 131.2, 127.6, 123.7, 113.0, 111.8, 108.0, 101.7, 68.5, 51.9, 31.9, 31.2, 19.3, 13.9; IR (neat): 3355, 2957, 1694, 1459, 1127 cm$^{-1}$; HREI-MS: m/z [M]$^+$ calcd for 261.1365 (C$_{15}$H$_{19}$NO$_3$), found, 261.1370.

5-(1-Butoxy)-3-indoleacetic Acid (Compound #39)

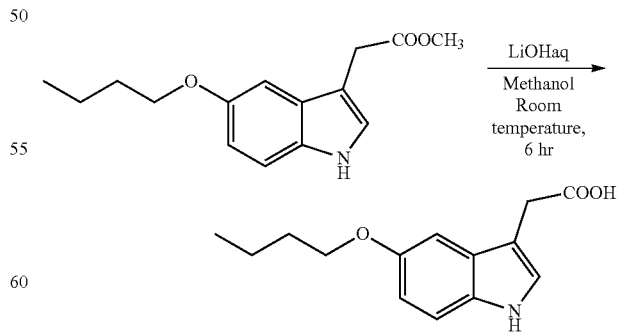

5-(1-Butoxy)-3-indoleacetic acid methyl ester (91.0 mg, 0.35 mmol) was dissolved in methanol (2 ml). To the solution, lithium hydroxide (12.5 mg, 0.52 mmol) was added, and the mixture was stirred at room temperature for 6 hours. After the reaction was confirmed by TLC to be complete, the reaction solution was acidified (pH=3 to 4) by the addition of 6 N hydrochloric acid, and the solvent was distilled off under reduced pressure. Water (5 ml) was added to the residue, followed by extraction with ethyl acetate (5 ml) three times. The organic layer was washed twice with brine and dried over anhydrous sodium sulfate. The solvent was distilled off under reduced pressure, and then, the residue was purified by silica gel column chromatography (chloroform:methanol=9:1) to obtain 5-(1-butoxy)-3-indoleacetic acid (compound #39) (43.8 mg, yield: 51.0%); Melting point: 137.8 to 141.1° C.; $^1$H NMR (400 MHz, CDCl$_3$): δ 7.24 (d, J=8.8 Hz, 1H), 7.14 (s, 1H), 7.04 (d, J=2.0 Hz, 1H), 6.87 (dd, J=8.8, 2.0 Hz, 1H), 4.01 (t, J=6.6 Hz, 2H), 3.76 (s, 2H), 1.78 (m, 2H), 1.05 (t. J=7.4 Hz, 3H); $^{13}$C NMR (100 MHz, CDCl$_3$): δ 173.3, 153.8, 131.2, 123.9, 113.2, 111.6, 107.5, 101.6, 31.6, 29.7, 19.3, 13.9; IR (neat): 3407, 2954, 1728, 1456, 1213, 1160 cm$^{-1}$; EI-MS m/z [M]$^+$ 247, 191 (60%); HREI-MS: m/z [M]$^+$ calcd for 247.1208 (C$_{14}$H$_{17}$NO$_3$), found 247.1189.

In Examples 2 to 7 and Reference Example 1 below, an erythropoietin-producing human hepatocellular carcinoma cell Hep3B (obtained from ATCC [American Type Culture Collection]) was cultured and maintained under conditions of 5% CO$_2$/20% O$_2$ and 37° C. in an RPMI1640 (manufactured by Life Technologies, Inc./GIBCO) medium containing 100 U/mL penicillin (manufactured by Life Technologies, Inc./GIBCO), 100 μg/mL streptomycin (manufactured by Life Technologies, Inc./GIBCO), and 10% fetal bovine serum (FBS) (manufactured by Life Technologies, Inc./GIBCO) (hereinafter, referred to as "RPMI1640 common medium 1"). In Example 15 below, Leigh syndrome patients were subjected to skin biopsy to obtain skin fibroblast cells, which were then primarily cultured under conditions of 5% CO$_2$/20% O$_2$ and 37° C. in a DMEM low glucose (manufactured by Life Technologies, Inc./GIBCO) medium containing 100 U/mL penicillin (manufactured by Life Technologies, Inc./GIBCO), 100 μg/mL streptomycin (manufactured by Life Technologies, Inc./GIBCO), and 1% FBS (manufactured by Life Technologies, Inc./GIBCO) (hereinafter, referred to as "DMEM low glucose common medium") to isolate cells (Leigh cells). In Example 13 below, a human kidney-derived cell line HK-2 (obtained from ATCC) was cultured and maintained under conditions of 5% CO$_2$/20% O$_2$ and 37° C. in a DMEM/F12 (manufactured by Life Technologies, Inc./GIBCO) medium containing 100 U/mL penicillin (manufactured by Life Technologies, Inc./GIBCO), 100 μg/mL streptomycin (manufactured by Life Technologies, Inc./GIBCO), and 10% fetal bovine serum (manufactured by Life Technologies, Inc./GIBCO) (hereinafter, referred to as "DMEM/F12 common medium"). In Example 14 below, a rat islet of Langerhans-derived cell line ISN-1e (kindly provided by Hisamitsu Ishihara, Nihon University School of Medicine) was cultured and maintained under conditions of 5% CO$_2$/20% O$_2$ and 37° C. in an RPMI1640 (manufactured by Life Technologies, Inc./GIBCO) medium containing 10 mM HEPES (manufactured by Sigma-Aldrich Corp.), 2 mM glutamine (manufactured by Sigma-Aldrich Corp.), 50 μM β-mercaptoethanol (manufactured by Sigma-Aldrich Corp.), 100 U/mL penicillin (manufactured by Life Technologies, Inc./GIBCO), 100 μg/mL streptomycin (manufactured by Life Technologies, Inc./GIBCO), and 10% FBS (manufactured by Life Technologies, Inc./GIBCO) (hereinafter, referred to as "RPMI1640 common medium 2").

EXAMPLE 2

1. Confirmation that the Compound of the Present Invention has Effect of Canceling Suppression of Erythropoietin Production by TNFα

It is known that in Hep3B cells, erythropoietin production is promoted under hypoxia conditions, but this promoting effect is suppressed in the presence of TNFα. Accordingly, in order to study the compound of the present invention for its effect of canceling the suppression of erythropoietin production, analysis was conducted using Hep3B cells cultured under hypoxia conditions and in the presence of TNFα.

1-1 Method

The Hep3B cells were seeded at 3×10$^6$ cells/well to a 12-well cell culture plate and then cultured under normal oxygen (20% O$_2$) for 24 hours. Each of 11 types of compounds (compounds #21 to 25 and 33 to 38) and recombinant human TNFα (manufactured by F. Hoffmann La Roche AG) were mixed at concentrations of 3 μM and 220 μg/ml, respectively, with RPMI1640 common medium 1. After further culture under hypoxia (1% O$_2$) for 24 hours, the concentration (mIU/ml) of erythropoietin produced in the medium was measured using human erythropoietin ELISA kit (manufactured by Bender MedSystems GmbH). Hep3B cells cultured in the absence of the compound and in the absence of TNFα (dimethyl sulfoxide [DMSO] added [1%]) ("med[TNFα-]" of FIG. 1) and Hep3B cells cultured in the presence of the compound and in the presence of TNFα (220 μg/ml) ("DMSO[TNFα+]" of FIG. 1) were used as controls.

1-2 Results

In the Hep3B cells, the addition of 11 types of compounds (compounds #21 to 25, and 33 to 38) was shown to increase the concentration of erythropoietin lowered by TNFα (FIG. 1). These results indicate that the 11 types of compounds (compound #21 to 25 and 33 to 38) have an effect of canceling the pathway of negatively regulating erythropoietin production by, for example, a cytokine such as TNFα.

EXAMPLE 3

2. Confirmation that the Compound of the Present Invention has Effect of Promoting Erythropoietin Production Subsequently, in order to study the compound of the present invention for its effect of promoting erythropoietin production, analysis was conducted using Hep3B cells cultured under normal oxygen conditions.

2-1 Method

The Hep3B cells were seeded at 3×10$^6$ cells/well to a 12-well cell culture plate and then cultured under normal oxygen (20% O$_2$) for 24 hours. Each of 9 types of compounds (compounds #2, 4, 13 to 15, and 17 to 20) and recombinant human TNFα (manufactured by F. Hoffmann La Roche AG) were mixed at concentrations of 3 μM and 220 μg/ml, respectively, with RPMI1640 common medium 1. After further culture under normal oxygen (20% O$_2$) for 24 hours, the concentration (mIU/ml) of erythropoietin produced in the medium was measured using human erythropoietin ELISA kit (manufactured by Bender MedSystems GmbH). Hep3B cells cultured in the absence of the compound ("Medium" and "DMSO" of FIG. 2), Hep3B cells cultured in the presence of activators (3,4-dihydroxybenzoic acid: 3,4-DHB [3 μM] and ciclopirox olamine) of the erythropoietin transcription-promoting factor HIF (hypoxia inducible factor, hypoxia-responsive transcriptional factor) ("3,4-DHB" and "file", respectively, of FIG. 2), and Hep3B cells cultured in the presence of a transcriptional repressor GATA-specific inhibitor (K7174 [3 µM]) of erythropoietin ("K7174" of FIG. 2) were used as controls.

2-2 Results

Under the normal oxygen (20% $O_2$) conditions, the 9 types of compounds (compounds #2, 4, 13 to 15, and 17 to 20) were shown to increase the concentration of erythropoietin in the Hep3B cells (FIG. 2). These results indicate that the 9 types of compounds (compounds #2, 4, 13 to 15, and 17 to 20) have an effect of promoting erythropoietin production.

EXAMPLE 4

3. Confirmation that the Compound of the Present Invention has Effect of Promoting Transcriptional Activity of Erythropoietin Gene Promoter Subsequently, in order to study the compound of the present invention for its effect of promoting the transcriptional activity of an erythropoietin gene promoter, luciferase reporter assay was conducted.

3-1 Method

[Plasmid Vector]

A plasmid vector HE-mPro-luc for luciferase assay on the promoter activity of the 5' upstream transcriptional regulatory region of the mouse erythropoietin gene was prepared by cleaving, with restriction enzymes XbaI and SacI, a region having a length from −571 to +53 bp starting at the translation initiation site of exon 1 of the mouse erythropoietin gene, and inserting this region to a luciferase reporter vector pXP2 (Nordeeen SK. BioTechniques. 6: 454-453, 1988).

[Transfection and Luciferase Reporter Assay]

The Hep3B cells were adjusted to $10 \times 10^4$ cells/well in a 24-well cell culture plate and subcultured. Under microscopy, the Hep3B cells that reached a cell density of to 80% were transfected with the plasmid DNA for luciferase reporter assay. The composition of a solution for transfection was prepared by mixing 2 µg of HE-mPro-luc, 50 ng of pRh-TK (manufactured by Promega K.K.), and 2 µl of Lipofectamine 2000 (manufactured by Invitrogen Corp.) with 100 µl of OptiMEM-I (manufactured by Life Technologies, Inc./GIBCO) per well, followed by incubation at room temperature for 20 minutes. The solution was added to the Hep3B cells in the 24-well cell culture plate preincubated in 0.5 ml of serum-free OptiMEM-I medium, and then incubated for 4 hours without serum and antibiotics under conditions of 37° C. and 5% $CO_2/20\%$ $O_2$. Then, the medium was replaced with RPMI1640 common medium 1 supplemented with each of 5 types of compounds (compounds #2, 4, 5, 18, and 21) at a concentration of 10 µM, followed by further incubation for 48 hours under conditions of 37° C. and 5% $CO_2/20\%$ $O_2$. Then, the medium was replaced with 0.5 ml of serum-free PBS, and the cells were gently washed, followed by the removal of PBS by suction. This operation was carried out twice. Then, 100 µl of passive lysis buffer (manufactured by Promega K.K.) was added thereto, and the cells were lysed by mixing at room temperature for 20 minutes. Hep3B cells cultured in the absence of the compound (DMSO added [1%]) ("20% O2/DMSO" of FIG. 3) were used as a negative control. Hep3B cells cultured in the presence of an HIF activator (FG-4592 [10 µM]) ("20% O2/FG4592" of FIG. 3) and Hep3B cells cultured under hypoxia (1% $O_2$) conditions and in the absence of the compound (DMSO added [1%]) ("1% O2/DMSO" of FIG. 3) were used as positive controls.

Dual Luciferase Reporter Assay System (manufactured by Promega K.K.) was used in the luciferase reporter assay. The amounts of firefly and *Renilla* luciferases were measured using a luminometer Lumat LB9507 (manufactured by BERTHOLD TECHNOLOGIES GmbH & Co. KG). The amount of Fire fly luciferase was divided by the amount of *Renilla* luciferase to calculate the transcriptional activity of the erythropoietin gene.

3-2 Results

Under the normal oxygen (20% $O_2$) conditions, the 5 types of compounds (compounds #2, 4, 5, 18, and 21) were shown to increase the transcription level of the erythropoietin gene promoter in the Hep3B cells (FIG. 3). A statistically significant difference was observed in the level increased by these compounds ("#" of FIG. 3 represents p<0.05 vs. "20% $O_2$/DMSO" [t-test, two-tailed test], and "##" represents p<0.01 vs. "20% $O_2$/DMSO" [t-test, two-tailed test]). These results indicate that the 5 types of compounds (compounds #2, 4, 5, 18, and 21) have an effect of promoting the transcriptional activity of the erythropoietin gene promoter and also indicate that this effect is superior to the effect of the existing HIF activator (FG-4592).

EXAMPLE 5

4. Confirmation that the Compound of the Present Invention has Effect of Increasing mRNA Expression Level of Erythropoietin Gene Subsequently, in order to study the compound of the present invention for its effect of increasing the mRNA expression level of the erythropoietin gene, analysis was conducted by quantitative PCR (quantitative polymerase chain reaction: QT-PCR).

4-1 Method

Of the 5 types of compounds confirmed in Example 4 to be effective for promoting the transcriptional activity of the erythropoietin gene promoter, 4 types of compounds (compounds #2, 4, 5, and 21) were selected. From Hep3B cells cultured in RPMI1640 common medium 1 supplemented with each of these 4 types of compounds at a concentration of 10 µM, total RNA was extracted using TriPure Isolation Reagent (manufactured by F. Hoffmann La Roche AG) in a 6-well cell culture plate. Hep3B cells cultured in the absence of the compound (DMSO added [1%]) ("20% O2/DMSO" of FIG. 4) were used as a negative control. Hep3B cells cultured in the presence of a GATA-specific inhibitor (K7174 [10 µM]) ("20% O2/K7174" of FIG. 4) and Hep3B cells cultured under hypoxia (1% $O_2$) conditions and in the absence of the compound (DMSO added [1%]) ("1% O2/DMSO" of FIG. 4) were used as positive controls.

The extracted RNA was used as a template to synthesize cDNA using SuperScript III RTS First-strand kit (manufactured by Invitrogen Corp.). Then, the expression of the erythropoietin mRNA was measured by quantitative PCR with GAPDH as an internal standard. The quantitative PCR was carried out using TaqMan® Gene Expression Assays (using GAPDH; Assay ID: Rn99999916_s1, and human erythropoietin; Assay ID: Hs00171267_m1 TaqMan[R] probes [manufactured by Applied Biosystems Inc.]) and Step One Plus Real-Time PCR System (manufactured by Applied Biosystems Inc.).

4-2 Results

Under the normal oxygen (20% $O_2$) conditions, the 4 types of compounds (compounds #2, 4, 5, and 21) were shown to increase the mRNA expression level of the erythropoietin gene in the Hep3B cells (FIG. 4). A statistically significant difference was observed in the level increased by these compounds ("#" of FIG. 4 represents p<0.05 vs. "$O_2$ 20%/DMSO 0.1%" [t-test, two-tailed test], and "##" represents $p<0.01$ vs. "20% $O_2$/DMSO" [t-test, two-tailed test]). The mRNA expression level of the GAPDH (internal standard) gene did not vary among the samples. These results indicate that the 4 types of compounds (compounds #2, 4, 5, and 21) have an effect of increasing the mRNA expression level of the erythropoietin gene and also indicate that the compounds having the effect of promoting the transcriptional activity of the erythropoietin gene promoter also have the effect of increasing the mRNA expression level of the erythropoietin gene.

EXAMPLE 6

5. Confirmation that the Compound of the Present Invention has Effect of Increasing HIF Subunit α (HIF-α) Production In order to examine the mechanism of action where the compound of the present invention exerts its effect of promoting the transcriptional activity of the erythropoietin gene promoter, the concentration of HIF subunit α (HIF-α) was measured.

5-1 Method

The Hep3B cells were seeded at $1\times10^4$ cells/well to a 24-well cell culture plate and then cultured under normal oxygen (20% $O_2$) for 24 hours. Each of 3 types of compounds (compounds #4, 21, and 35) was mixed at a concentration of 10 μM into RPMI1640 common medium 1. After further culture under normal oxygen (20% $O_2$) for 24 hours, the concentration of HIF-α produced in the medium was measured using Total HIF-1 α Cell-Based ELISA Kit (manufactured by R&D Systems, Inc.). Hep3B cells cultured in the absence of the compound (DMSO added [1%]) ("Control" of FIG. 5) were used as a negative control. Hep3B cells cultured in the presence of HIF activators (FG-4592 [10 μM], DMOG [10 μM], and ciclopirox [10 μM]) ("FG", "DMOG", and "Ciclo", respectively, of FIG. 5) were used as positive controls.

5-2 Results

Under the normal oxygen (20% $O_2$) conditions, the 3 types of compounds (compounds #4, 21, and 35) were shown to increase the HIF-α concentration in the Hep3B cells (FIG. 5). A statistically significant difference was observed in the level increased by these compounds ("#" of FIG. 5 represents $p<0.05$ vs. "Control" [t-test, two-tailed test]). These results indicate that the 3 types of compounds (compounds #4, 21, and 35) have an effect of increasing HIF-α production.

Considering the results of Examples 3 to 6 together, it is suggested that the compound of the present invention increases the amount of HIF-α produced and activates the pathway of positively regulating erythropoietin production by HIF, so that the transcriptional activity of the erythropoietin gene promoter is promoted, the mRNA expression level of the erythropoietin gene is increased, and the erythropoietin production is increased.

REFERENCE EXAMPLE 1

6. Confirmation that Compounds #1 to 15, 17 to 31, and 34 to 39 have Effect of Increasing ATP Production Erythropoietin is known to have a protective effect against ischemic organ injury. It is also known that ATP concentration is lowered at a cerebral ischemic site. Accordingly, on the hypothesis that under the mechanism where erythropoietin exerts its protective effect against ischemic organ injury, intracellular ATP concentration is elevated, of the 41 types of compounds used in the screening for erythropoietin expression-enhancing agents, compounds #1 to 15, 17 to 31, and 34 to 39 were studied for their effects of increasing ATP production.

6-1 Method

The Hep3B cells were seeded at $1\times10^4$ cells/well to a 24-well cell culture plate and then cultured under normal oxygen (20% $O_2$) for 24 hours. Each of 36 types of compounds (compounds #1 to 15, 17 to 31, and 34 to 39) was mixed at a concentration of 10 μM into RPMI1640 common medium 1. After further culture under normal oxygen (20% $O_2$) for 3 hours, 6 hours, or 24 hours, the concentration of ATP produced in the medium was measured using ATP Assay Reagent of "Cells" (manufactured by Toyo B-Net Co., Ltd.) and GloMa 96 Microplate Luminometer (manufactured by Promega K.K.). Hep3B cells cultured in the absence of the compound (DMSO added [1%]) ("DMSO" of FIGS. 6 to 8) were used as a negative control. Hep3B cells cultured in the presence of HIF activators (FG-4592 [10 μM], DMOG [10 μM], 3,4-DHB [10 μM], and ciclopirox [10 μM]) ("FG", "DMOG", "34-DHB", and "Cyclo", respectively, of FIGS. 6 to 8) and Hep3B cells cultured in the presence of a transcriptional repressor GATA-specific inhibitor of erythropoietin (K7174 [10 μM]) ("K7174" of FIGS. 6 to 8) were used as positive controls.

6-2 Results

The results of culture for 3, 6, and 24 hours are shown in FIGS. 6, to 8, respectively. The 36 types of compounds (compounds #1 to 15, 17 to 31, and 34 to 39) were shown to increase the ATP concentration in the Hep3B cells (FIGS. 6 to 8), and the level of increased by 8 types of compounds (compounds #1 to 8) was shown to be particularly high (FIG. 7). These results indicate that the 36 types of compounds (compounds #1 to 15, 17 to 31, and 34 to 39) have an effect of increasing ATP production, and this effect is particularly high in the 8 types of compounds (compounds #1 to 8). Similar study was further conducted at a compound concentration of 3 μM using the 8 types of compounds (compounds #1 to 8) having a particularly high effect on ATP production. As a result, the compounds #1 to 8 even used at a concentration of 3 μM were shown to have an effect of similarly increasing ATP production.

EXAMPLE 7

7. Study on Cytotoxicity of the Compound of the Present Invention

In order to study the compound of the present invention for its cytotoxicity, the cell survival rate of cells cultured in the presence of the compound of the present invention was measured.

7-1 Method

The Hep3B cells were seeded at $1\times10^4$ cells/well to a 24-well cell culture plate and then cultured under normal oxygen (20% $O_2$) for 24 hours. Compound #4 was mixed at a concentration of 0.5, 1, 5, 10, or 50 μM into RPMI1640 common medium 1. After further culture under normal oxygen (20% $O_2$) for 24 hours, the number of live cells was measured using Cell Counting Kit-8 (manufactured by Dojindo Laboratories) to calculate the survival rate of the cells. Hep3B cells cultured in the absence of the compound (DMSO added [1%]) ("DMSO" of FIG. 9) and Hep3B cells cultured in the presence of HIF activators (DMOG [10 μM] and ciclopirox [10 μM]) ("DMOG" and "Ciclopirox", respectively, of FIG. 9) were used as controls.

7-2 Results

The cell survival rate of the cells cultured using 100 μM compound #4 was decreased to approximately 70% as compared with the cells cultured using 0.5 µM compound #4, whereas the cell survival rate of the cells cultured using 1, 5, or 10 µM compound #4 was rarely different from that of the cells cultured using 0.5 µM compound #4 (FIG. 9). The cell survival rate of the cells cultured using 0.5 µM compound #4 was almost the same as that of the cells cultured in the absence of the compound (DMSO added [1%]). These results indicate that the compound #4 of the present invention at least used at a concentration ranging from 0 to 10 µM hardly exhibit cytotoxicity.

EXAMPLE 8

8. Study on Absorption of the Compound of the Present Invention

In order to study the compound of the present invention for its absorbability, the compound of the present invention was administered to animal models, and the plasma concentration of the compound of the present invention was measured.

8-1 Method
[Administration of Compound and Isolation of Plasma from Mouse after Administration]

Compound #4 was administered alone to the tail veins of 3 mice (C57BL/6N 8 W, male, 21-25 g). 30 minutes, 1 hour, and 6 hours after the administration, each mouse was cervically dislocated, and 500 µl of blood was collected from the heart. Then, an anticoagulant (10 µl of heparin) was added thereto, and the resulting blood was centrifuged (12000 rpm×20 min, 4° C.) to isolate plasma. DMSO (57 µl) was administered alone to the tail veins of mice, which were in turn used as controls.

[Quantification Using LC/MS/MS]

The plasma concentration of the compound #4 was quantified using LC/MS/MS constituted by TSQ Quantum Ultra (manufactured by Thermo Fisher Scientific Inc.) and NANOSPACE SI-2 (manufactured by Shiseido Co., Ltd.). Conditions for the selected reaction monitoring (SRM) method of the compound #4 or 2-methyl-5-([2-naphthylamino]carbonyl)-3-thienyl)acetic acid used as an internal standard (hereinafter, referred to as an "internal standard compound") are "m/z 311.1>116.0 (collision energy, CE=24)" and "m/z 324.1>280.0 (CE=14)". "Xbridge C18 (150 mm×2.1 mm i.d., 3.5 µm particle size)" was selected as an analytical column. The compound was eluted in a two-solution gradient of 2.5 mM ammonium acetate and 2.5 mM ammonium acetate/methanol (2.5/97.5 [v/v]) at a flow rate of 200 µl/min in a mobile phase. The compound #4 and the internal standard compound were detected 8.51 and 9.00 minutes, respectively (upper column of FIG. 10). The analysis time per run was 15 minutes. The plasma sample (50 µl) was pretreated by the deproteinization method using the internal standard compound (100 ng/ml, 50 µl) and 0.1% formic acid-acetonitrile (200 µl). After drying of the supernatant over nitrogen, the residue was redissolved in water/methanol (50/50 [v/v]) (50 µl). The sample (1 µl) was introduced through a filter to LC/MS/MS to quantify the plasma concentration (µg/ml) of the compound #4 (lower column of FIG. 10).

8-2 Results

The compound #4 was detected at a high level in the plasma at least 30 minutes after the administration and detected up to at least 6 hours after the administration (lower column of FIG. 10, "#4"). On the other hand, the compound #4 was not detected from the control mice given DMSO (lower column of FIG. 10, "DMSO"). These results indicate that the administered compound #4 is efficiently absorbed into the body.

EXAMPLE 9

9. Confirmation that the Compound of the Present Invention has Effect of Promoting Erythropoietin Production In Vivo In order to study the compound of the present invention for its effect of promoting erythropoietin production in vivo, analysis was conducted using mice given the compound of the present invention.

9-1 Method

A mixed solution (200 µl) of each of 4 types of compounds (compounds #4, 5, 21, and 35) (10 mg/100 µl of DMSO) (10 µl) and corn oil (190 µl) was prepared. This mixed solution (200 µl) was orally administered to each mouse (C57BL/6N 8 W, male, 21-25 g) between 15:00 to 18:00 every day using a sonde. This administration was carried out for 7 consecutive days. Mice orally given corn oil or DMSO and corn oil as well as non-administered mice were used as controls.

24 hours after the final administration, each mouse was cervically dislocated, and 500 µl of blood was collected from the heart. Then, an anticoagulant (10 µl of heparin) was added thereto, and the resulting blood was centrifuged (12000 rpm×20 min, 4° C.) to isolate plasma. The plasma concentration (pg/ml) of erythropoietin was measured using a kit (Quantikine Mouse/Rat Epo Immunoassay, manufactured by R&D Systems, Inc.).

9-2 Results

The amount of erythropoietin in the mouse blood was shown to be increased by the administration of the 4 types of compounds (compounds #4, 5, 21, and 35) ("#4, 5, 21, and 35" of FIG. 11A) as compared with the administration of corn oil alone or DMSO and corn oil ("Corn oil" and "DMSO+corn oil", respectively, of FIG. 11A) or no administration ("Normal" of FIG. 11A). These results indicate that the 4 types of compounds (#4, 5, 21, and 35) have an effect of promoting erythropoietin production in vivo and also support the results of verifying the effect of promoting erythropoietin production in vitro in Examples described above.

EXAMPLE 10

10. Confirmation that the Compound of the Present Invention has Effect of Promoting Erythrocyte Production Since the compound of the present invention was confirmed to have the effect of promoting erythropoietin production in vivo, the compound of the present invention was studied for its effect of promoting erythrocyte production.

10-1 Method

Compound #4 (1 mg) was mixed with 200 µl of CMC (carboxymethylcellulose). This compound #4 mixed solution (1 mg/200 µl of CMC) was orally administered to each mouse (C57BL/6N 8 W, male, 21-25 g) between 15:00 to 18:00 every day using a sonde. This administration was carried out for 7 consecutive days (n=3). Mice orally given CMC were used as controls (n=3).

24 hours after the final administration, each mouse was cervically dislocated, and 500 µl of blood was collected from the heart. Then, an anticoagulant (10 µl of heparin) was added thereto, and the Hct value and the hemoglobin concentration were measured using i-STAT (manufactured by Fuso Pharmaceutical Industries, Ltd.).

10-2 Results

The mouse Hct value (% PCV) was 42.7±1.78 (mean±standard deviation) in the controls given CMC alone and, by contrast, was increased to 47.7±0.816 by the administration of the compound #4 (left diagram of FIG. 11B). The hemoglobin concentration (g/dL) in the mouse blood was 14.5±0.604 (mean±standard deviation) in the controls given CMC alone and, by contrast, was increased to 16.2±0.286 by the administration of the compound #4 (right diagram of FIG. 11B). These results indicate that the compound #4 has an effect of promoting erythrocyte production.

Considering the results of Examples 9 and 10 together, the compound of the present invention promotes erythropoietin production in vivo and elevates erythrocyte concentration in blood, indicating that the compound of the present invention is effective for the prevention or treatment of anemia caused by reduced erythropoietin expression or reduced erythropoietin reactivity.

EXAMPLE 11

11. Confirmation that the Compound of the Present Invention has Effect of Improving Liver Function As mentioned above, erythropoietin is known to have a protective effect against ischemic organ injury. Kidney dysfunction caused by hepatic ischemia is known as an ischemic organ injury. Accordingly, on the assumption that the compound of the present invention, i.e., the compound confirmed to be effective for promoting erythropoietin production, could improve ischemic injury of the liver and improve liver function, the compound of the present invention was studied for its effect of improving liver functions.
11-1 Method Compound #4 (10 mg/100 μl of DMSO) (10 μl) and compound #4 (20 mg/100 μl of DMSO) (15 μl) were mixed with 190 μl and 185 μl, respectively, of corn oil to prepare low-concentration (5 μg/ml) compound #4 and high-concentration (15 μg/ml) compound #4 mixed solutions (200 μl each). Each mixed solution (200 μl) was orally administered to each mouse (C57BL/6N 8 W, male, 21-25 g) between 15:00 to 18:00 every day using a sonde. This administration was carried out for 7 consecutive days (n=4). Mice orally given DMSO were used as controls (n=4).

24 hours after the final administration, each mouse was cervically dislocated, and 500 μl of blood was collected from the heart. Then, an anticoagulant (10 μl of heparin) was added thereto, and the resulting blood was centrifuged (12000 rpm×20 min, 4° C.) to isolate plasma. The plasma concentrations of indexes for liver functions (GOT [glutamic oxaloacetic transaminase] and GPT [glutamic pyruvic transaminase]) were measured using Transaminase CII-Test Wako (manufactured by Wako Pure Chemical Industries, Ltd.) to examine the effect of improving liver functions. Also, the plasma concentration (pg/ml) of erythropoietin was measured using a kit (Quantikine Mouse/Rat Epo Immunoassay, manufactured by R&D Systems, Inc.).
11-2 Results The compound #4 administered at the low concentration (5 μg/ml) and the high concentration (15 μg/ml) was confirmed to elevate the erythropoietin concentration in the mouse plasma (left diagram of FIG. 12). The administered compound #4 was shown to lower the GOT and GPT concentrations in the plasma (central and right diagrams, respectively, of FIG. 12). These results indicate that the compound #4 has an effect of improving liver functions.

EXAMPLE 12

12. Confirmation that the Compound of the Present Invention has Effect of Improving Cerebral Ischemic Injury As mentioned above, erythropoietin is known to have a protective effect against ischemic organ injury. A cerebrovascular disorder caused by cerebral ischemia is known as an ischemic organ injury. In order to study the compound of the present invention, i.e., the compound confirmed to be effective for promoting erythropoietin production, for its effect of improving cerebral ischemic injury, analysis was conducted using MCA (middle cerebral artery) occlusion mouse models (8-12-week-old C57BL/6 mice [22-30 g]).
12-1 Method
[Method for Administering the Compound of the Present Invention and Preparation of MCA Occlusion Mouse Model]

Two types of compounds (compounds #4 and 35) (40 mg/kg of mouse body weight) were each intraperitoneally administered to a mouse 4 hours before ischemia (n=1). A vehicle (DMSO) was administered to a control (n=1). Anesthesia was induced in each mouse with 4% halothane and oxygen and maintained by the intraperitoneal administration of ketamine (40 mg/kg) and xylazine (4 mg/kg) at 30-minute intervals. After the induction of systemic anesthesia, bifurcation of the common carotid artery was exposed under a microscope. A 6-0 nylon thread having a silicon-coated tip was inserted from the internal carotid artery toward the central side so that its tip reached the anterior communicating artery. The common carotid artery was further ligated to block blood flow into the middle cerebral artery. After the ischemic burden for 30 minutes, the nylon thread was removed so that the ligated common carotid artery was released to induce reperfusion.
[TTC Staining Method and Neurological Evaluation]

24 hours after the reperfusion, each mouse was cervically dislocated and then decapitated to excise the brain. Five coronal sections of the cerebrum having a thickness of 2 mm were prepared from the boundary between the cerebrum and the cerebellum. The coronal sections of the cerebrum were stained with TCC through a reaction at 37° C. for 20 minutes with a TTC solution diluted to 1.5% with PBS. Images of the coronal sections of the cerebrum thus stained were taken using a digital camera.
12-2 Results A region exhibiting TTC-unstained tissues that underwent cell death, i.e., the volume of the cerebral infarction site, was shown to be decreased in the brains of the MCA occlusion mouse models given the compounds #4 and 35 compared with the volume of the cerebral infarction site in the MCA occlusion mouse model given DMSO (FIG. 13). These results indicate that the compounds #4 and 35 have an effect of improving cerebral ischemic injury such as cerebral infarction.

EXAMPLE 13

13. Confirmation that the Compound of the Present Invention has Renal Protective Effect In kidney damages such as chronic kidney disease, ischemic nephropathy, and diabetic nephropathy, the kidney is known to be in an ischemic state. As mentioned above, the compound of the present invention was confirmed to have the effect of improving cerebral ischemic injury. Accordingly, the compound of the present invention was subsequently studied for its renal protective effect. Specifically, the compound of the present invention was studied for its effect of canceling cytotoxicity to a human kidney-derived cell line (HK-2) cultured in the presence of cisplatin.
13-1 Method The HK-2 cells were seeded at $5\times10^3$ cells/well to a 96-well cell culture plate and then cultured overnight. Cisplatin and compound #4 were mixed at 30 μM and each concentration (30, 10, 3, 1, 0.3, 0.1, 0.03, 0.01, and 0.003 μM), respectively, into DMEM/F12 common medium. After further culture for 24 hours, conversion to formazan dye by mitochondrial dehydrogenase in live cells was detected by the measurement of absorbance at OD 450 mm using a kit (Cell counting kit-8, manufactured by Dojindo Laboratories)

to analyze the ratio of live cells. HK-2 cells cultured in the absence of cisplatin ("Cisplatin-" of FIG. 14) and HK-2 cells cultured in the presence of cisplatin (30 µM) and in the absence of the compound #4 ("Cisplatin+" of FIG. 14) were used as controls.

13-2 Results

The compound #4 at least at a concentration of 1 to 300 µM significantly suppressed HK-2 cell death by cisplatin. Particularly, the compound #4 used at a concentration around 30 µM was shown to be able to efficiently suppress cell death (FIG. 14). These results indicate that the compound #4 has an effect of canceling the nephrotoxicity of a drug such as cisplatin, i.e., a renal protective effect against such a drug.

Study was further conducted on whether cell death could be effectively suppressed by the preincubation of HK-2 cells in the presence of the compound of the present invention. The cells were cultured in advance for 1 hour with the compound #4 of the present invention having a concentration of 3 µM and then analyzed according to the method described in Example 12. As a result, the HK-2 cell death by cisplatin was shown to be further suppressed by the preincubation ("Pretreatment+" of FIG. 15) as compared with no preincubation ("Pretreatment-" of FIG. 15) (FIG. 15). These results suggest the possibility that the compound #4 administered at a plurality of doses can more effectively exert its effect of canceling the nephrotoxicity of a drug such as cisplatin, i.e., its renal protective effect against such a drug.

EXAMPLE 14

14. Confirmation that the Compound of the Present Invention has Effect of Promoting Insulin Secretion In order to study the compound of the present invention for its effect of promoting insulin secretion, the amount of ATP produced was analyzed using an islet of Langerhans-derived cell line (ISN-1e).

14-1 Method

The ISN-1e cells were seeded at $2 \times 10^3$ cells/well to a 96-well cell culture plate and then cultured overnight. Compound #4 was mixed at each concentration (10, 3, 1, 0.3, 0.1, and 0.03 µM) into RPMI1640 common medium 2. After further culture for 3 hours, the concentration of ATP produced in the medium was measured using ATP Assay Reagent "of Cells" (manufactured by Toyo B-Net Co., Ltd.) and GloMa 96 Microplate Luminometer (manufactured by Promega K.K.). ISN-1e cells cultured in the absence of the compound (DMSO added [1%]) ("control" of FIG. 16) and ISN-1e cells cultured in the presence of an HIF activator (FG-4592 [10, 3, 1, 0.3, and 0.1 µM]) were used as controls.

14-2 Results

The compound #4 at least at a concentration of 0.03 to 10 µM was shown to significantly (two or more times relative to the control) elevate the ATP concentration in the ISN-1e cells (FIG. 16). In the islet of Langerhans, elevated intracellular ATP concentration is known to promote insulin secretion. This indicates that the compound #4 has an effect of stimulating insulin secretion in the cells of the islet of Langerhans and suggests the possibility that the compound #4 can improve diabetes mellitus by such an effect.

EXAMPLE 15

15. Confirmation that Compounds #2, 4, 5, 21, and 35 have Effect of Suppressing Cell Death Caused by Oxidative Stress in Leigh Cell The compound of the present invention was shown to have the effect of canceling the pathway of negatively regulating erythropoietin production by a cytokine (TNFα) under hypoxia conditions (see Example 2) and to have the effect of improving cerebral ischemic injury (see Example 12). From these results, it was hypothesized that the compound of the present invention has an effect of attenuating (suppressing) oxidative stress by improving an ischemic or hypoxic state. Accordingly, in order to study the compound for its effect of suppressing cell death caused by oxidative stress in Leigh cells, Leigh cells treated with a glutathione synthesis inhibitor BSO were cultured in the presence of compounds #2, 4, 5, 21 and 35, and the cell survival rate was measured.

15-1 Method

The Leigh cells were seeded at $4 \times 10^4$ cells/well to a 24-well cell culture plate and then cultured for 24 hours. The glutathione synthesis inhibitor BSO (L-buthionine sulphoximine) (manufactured by Sigma-Aldrich Corp.) was mixed at 500 µl into a medium. After culture for 24 hours in the presence of BSO, each of 5 types of compounds (compounds #2, 4, 5, 21, and 35) was mixed at 10 µM into the medium. After culture for 4 days in the presence of these 5 types of compounds, the number of live cells was measured using Cell Counting Kit-8 (manufactured by Dojindo Laboratories) to calculate the survival rate of the cells ("BSO+#2", "BSO+#4", "BSO+#5", "BSO+#21", and "BSO+#35" of FIG. 17). Leigh cells cultured in the absence of the compound and BSO ("cell only" of FIG. 17), Leigh cells cultured in the absence of the compound ("BSO" of FIG. 17), Leigh cells cultured in the presence of an HIF activator (FG-4592 [10 µM]) ("BSO+FG4592" of FIG. 17), Leigh cells cultured in the presence of an ATP production promoter (coenzyme Q10 [1 µM]) ("BSO+CoQ10" of FIG. 17), and Leigh cells cultured in the presence of an antioxidant (α-lipoic acid [1 µM]) ("BSO+αLA" of FIG. 17) were used as controls.

15-2 Results

The 5 types of compounds (compounds #2, 4, 5, 21, and 35) were shown to be able to efficiently suppress the cell death of the Leigh cells by BSO (FIG. 17). These results indicate that the 5 types of compounds (compounds #2, 4, 5, 21, and 35) can suppress cell death caused by oxidative stress in patients with a mitochondrial disease such as Leigh syndrome and suggests that the compound of the present invention can treat the mitochondrial disease such as Leigh syndrome.

INDUSTRIAL APPLICABILITY

The present invention can cancel the suppression of erythropoietin production or promote erythropoietin production and can treat or prevent anemia associated with a disease caused by reduced erythropoietin production or reduced erythropoietin reactivity. In addition, the present invention can also delay the progression of such a disease or improve symptoms of the disease and as such, is useful in the field of therapeutic drugs for the disease.

The invention claimed is:

1. A compound represented by the following formula (I-1'), (I-1''), (I-2), (I-2''), (I-2'''), (I-3), (I-3'), (II-2), (III), or (IV-1) or a pharmaceutically acceptable salt thereof:

Formula (I-1'):

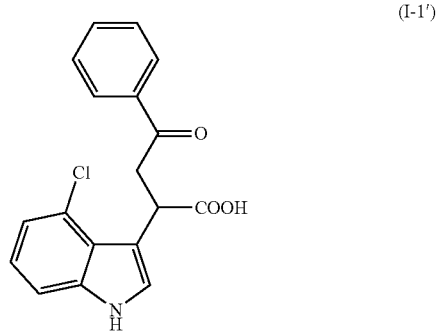

(I-1')

Formula (I-1″):

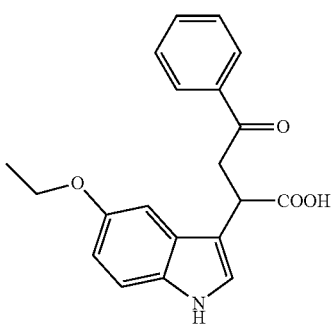

(I-1″)

Formula (I-2):

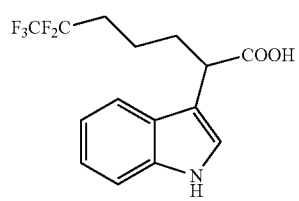

(I-2)

Formula (I-2″):

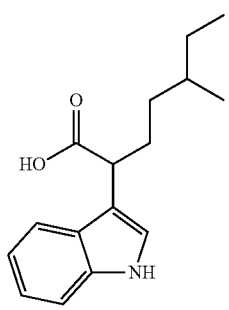

(I-2″)

Formula (I-2‴):

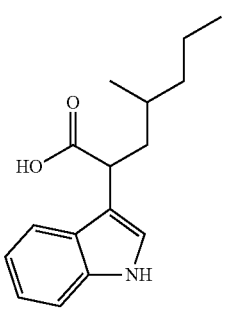

(I-2‴)

Formula (I-3)

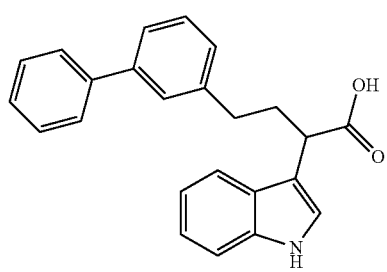

(I-3)

Formula (I-3′):

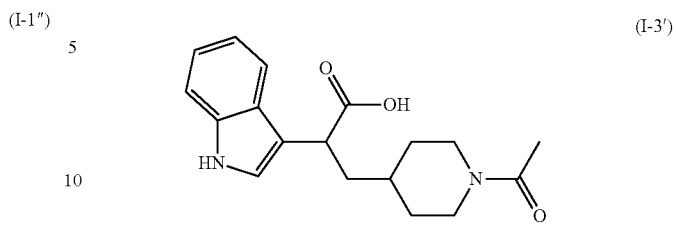

(I-3′)

Formula (II-2):

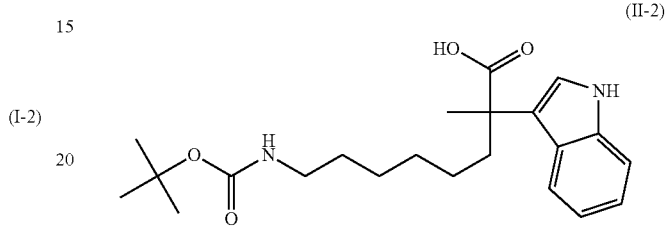

(II-2)

Formula (III):

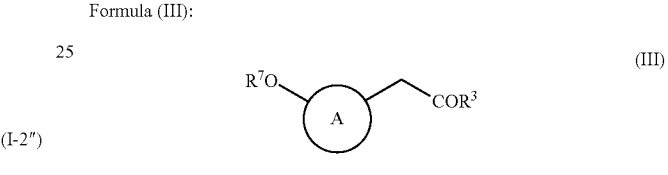

(III)

wherein A represents indole, and positions 3 and 5 of the indole are each substituted by an acetic acid group and $R^7O$, $R^7$ represents an alkyl group having 1 to 5 carbon atoms or a benzyl group, wherein when $R^7$ represents an alkyl group, $R^3$ represents any one group selected from $OR^4$, $NHR^4$ and $NR^4R^5$, and $R^4$ and $R^5$ are the same or different and each represents an unsubstituted alkyl group having 1 to 4 carbon atoms, and wherein when $R^7$ represents a benzyl group, the benzene ring of the benzyl group is substituted by one or more alkyl groups having 1 to 3 carbon atoms or alkoxyl groups having 1 to 3 carbon atoms, $R^3$ represents any one group selected from OH, $OR^4$, $NHR^4$, and $NR^4R^5$, and $R^4$ and $R^5$ are the same or different and each represents a substituted or unsubstituted alkyl group having 1 to 4 carbon atoms, Formula (IV-1)

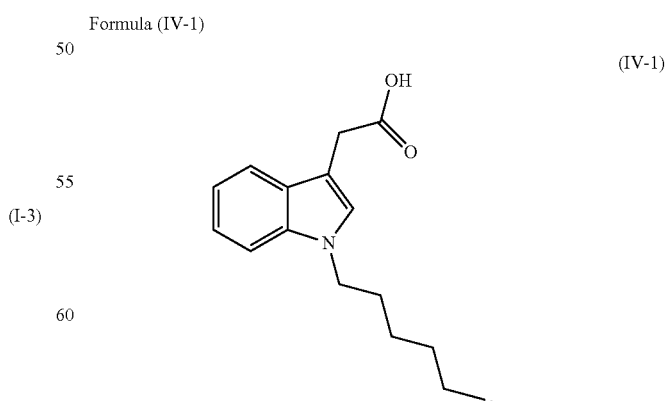

(IV-1)

2. The compound according to claim 1, which is represented by the following formula (III-1):

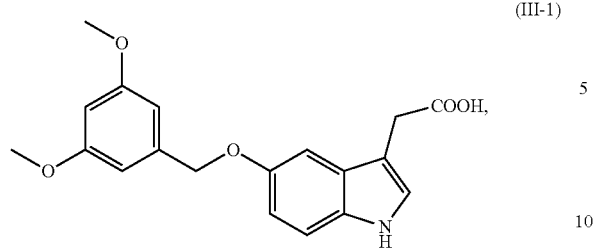
(III-1)
or a pharmaceutically acceptable salt thereof.
* * * * *